(12) United States Patent
Jeanpetit et al.

(10) Patent No.: US 6,344,457 B1
(45) Date of Patent: Feb. 5, 2002

(54) AMINO ACID DERIVATIVES INHIBITING EXTRACELLULAR MATRIX METALLOPROTEINASE AND TNF ALPHA RELEASE

(75) Inventors: Christian Jeanpetit, Bougival; Didier Prigent, Bures sur Yvette; Pierre-André Settembre, Houilles; Marie-Michèle Trancart, Voisins le Bretonneux, all of (FR)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 09/403,037

(22) PCT Filed: Apr. 21, 1998

(86) PCT No.: PCT/FR98/00801

§ 371 Date: Dec. 17, 1999

§ 102(e) Date: Dec. 17, 1999

(87) PCT Pub. No.: WO98/47863

PCT Pub. Date: Oct. 29, 1998

(30) Foreign Application Priority Data

Apr. 22, 1997 (FR) ............................................. 97 04971

(51) Int. Cl.⁷ ...................... A61K 31/535; A61K 31/19; C07D 265/30; C07C 255/00; C07C 259/04
(52) U.S. Cl. .................... 514/238.2; 514/575; 544/162; 544/168; 558/445; 562/621; 562/623
(58) Field of Search ................................. 562/621, 623; 544/162, 168; 514/238.2, 575; 558/445

(56) References Cited

FOREIGN PATENT DOCUMENTS

EP          0 613 883 A1  *  2/1997
WO          97/03966      *  2/1997

OTHER PUBLICATIONS

Bailey et al, Bioorganic & Medicinal Chemistry Letters, 8, pp. 23–28, 1998.*
Broughton et al., J. Chem. Soc., Perkins Trans. 1, pp. 857–860, 1975.*
Robinson et al., Bioorganic & Medicinal Chemistry Letters, vol. 6, No. 14, pp. 1719–1724, 1996.*
Ghose et al., J. Am. Chem. Soc., vol. 117, pp. 4671–4682, 1998.*

* cited by examiner

*Primary Examiner*—Deborah C. Lambkin
(74) *Attorney, Agent, or Firm*—Oblon, Spivak, McClelland, Maier & Neustadt, P.C.

(57) ABSTRACT

The invention concerns compounds of general formula (X) in which Y represents in particular —CONHOH, $R_1$ represents in particular a $C_1$–$C_5$ alkyl group, AA represents an amino acid, or an amino acid sequence, and $R_3$ represents in particular a group of formula —NH—$(CH_2)_2$—$SCH_3$. The invention also concerns the pharmaceutical compositions containing them, and the methods for obtaining them.

39 Claims, No Drawings

AMINO ACID DERIVATIVES INHIBITING EXTRACELLULAR MATRIX METALLOPROTEINASE AND TNF ALPHA RELEASE

This application is a 371 of PCT/FR98/00801 filed Apr. 21, 1998.

This invention relates to new amino acid derivatives possessing an inhibiting action on metalloproteinase of the extracellular matrix, and more particularly gelatinase, a process for the production of these derivatives and pharmaceutical compositions containing them. These derivatives also possess an inhibiting action on the release of αTNF (Tumor Necrosis Factor) as well as on the production of αTGF (Tumor Growth Factor).

The breakdown of the extracellular matrix is due principally to the enzymatic action of metalloproteinase (MMP).

The enzymatic activity of this metalloproteinase is regulated physiologically by natural inhibitors such as TIMP (Tissue Inhibitor of Metalloproteinase) or alpha-2-macroglobulin. An imbalance in the production of the enzymes and their inhibitors leads to a high protein activity observed in pathologies involving a process of breakdown of the extracellular matrix.

Compounds having the property of inhibiting the action of the metalloproteinase involved in the breakdown of the extracellular matrix, such as collagenase, gelatinase and stromelysine therefore may be used in the treatment of pathologies in which metalloproteinase is involved, such as rheumatoid arthritis, osteoarthritis, osteoporosis, corneal ulceration, periodontitis, gingivitis or tumorous invasion and metastatic proliferation, atherosclerosis, AIDS, chronic inflammatory diseases of the intestine, these examples not being restrictive.

αTNF is a pro-inflammatory cytokin which is produced initially in the form of an inactive 28 kDa precursor. The cleavage of this precursor leads to the release of an active form of 17 kDa involved in numerous inflammatory, immunological, infectious or malignant pathologies. Compounds inhibiting the release of αTNF therefore may be used in the treatment of numerous pathologies in which αTNF is involved, such as rheumatoid arthritis, Crohn's disease, plaque sclerosis, septic shock, cancer or cachexia associated with an immunodeficiency, these examples not being restrictive.

αTGF is a growth factor forming part of the EGF (Epidermal Growth Factor) family. It is produced by the embryonic tissues, keratinocytes, macrophages, eosinophiles, epitheliums (mammary gland and cornea), pancreas, gastric mucous membrane, pituitary and brain.

αTGF interacts with the EGF receptor; a cascade of reactions, resulting in mitosis, ensues. αTGF also is mitogenic for tumorous cells.

αTGF induces the transformation and growth of cells in vitro.

An overproduction of αTGF is observed in tumors as well as in cell stock derived from mammary tumors. αTGF also is involved in angiogenesis. It likewise stimulates hypercalcemia and inhibits gastric acid secretion. Finally, it is involved in inflammatory reactions.

Compounds inhibiting the production of αTGF therefore may be used in the treatment of pathologies in which αTGF is involved, such as cancer, psoriasis, eczema, the formation of keloids, diabetic retinopathy, atherosclerosis, inflammatory diseases, these examples not being restrictive.

Numerous inhibitors of MMP and/or of TNF release already are known, the most active being the derivatives of hydroxamic acid with the general formula I:

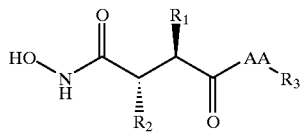

wherein $R_1$ represents an alkyl chain, generally isobutyl, and AA an amino acid or an amino acid chain. Such compounds are described, for example, in patent applications EP 0214639, WO 93/20047, WO 94/02447, WO 94/21625, WO 94/10990, WO 95/06031. MMP inhibitors inhibiting the production of αTGF are described in international application WO 96/25156.

Other compounds have been described as inhibitors of matrix metalloproteinase in which the hydroxamic function has been replaced by a thiol (general formula II) or phosphinic (general formula III) function.

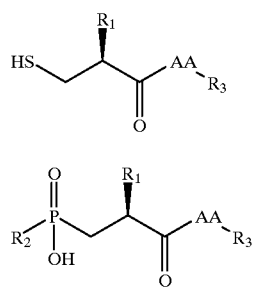

Finally, derivatives of N-carboxymethyl peptides also have been claimed (general formula IV).

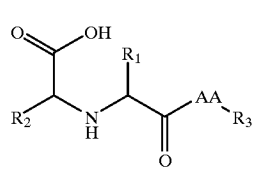

In these different families, the $R_1$ residue interacts with the subsite $S'_1$ of the various enzymes. The stereochemistry of the carbon bearing this residue is essential for activity and must be of precise configuration, R, in the case of hydroxamic (J. Enzyme Inhibition, (1987), 2, 1–22) and phosphinic derivatives. None of the existing patents describing the MMP inhibitors makes reference to disubstitution on the $R_1$-bearing carbon.

The substitution of this carbon therefore is of extreme importance for activity, and it has been shown in particular that substitution of the hydrogen in this carbon with a methyl remainder brings about a loss of activity of a factor of 300 between compound V and compound VI (J. Am. Chem. Soc. (1995), 117, 4671–4682).

V

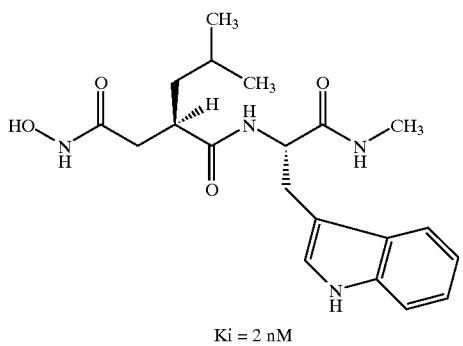

Ki = 2 nM

VI

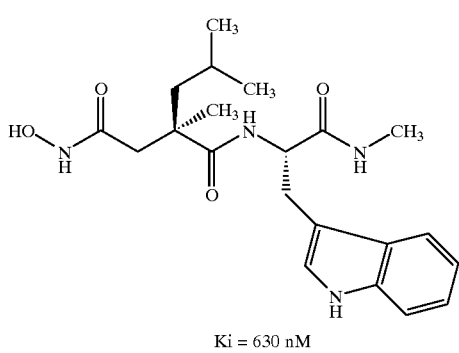

Ki = 630 nM

R. P. ROBINSON et al. (Bioorg. Med. Chem. Letters (1996), 6, 1719–1724) also have studied the substitution of this carbon. The gem disubstitution leads systematically to a significant loss of activity (compound VII versus compounds VIII and IX).

VII

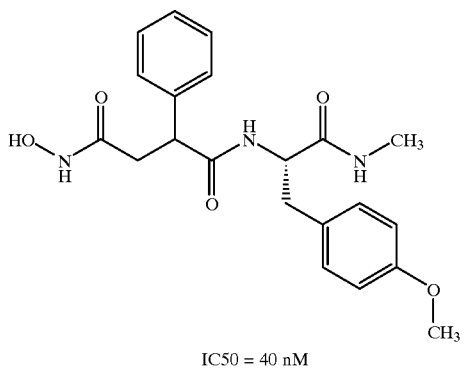

IC50 = 40 nM

VIII

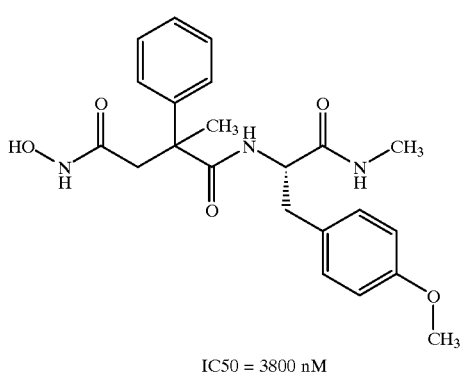

IC50 = 3800 nM

IX

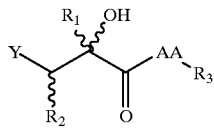

IC50 > 30000 nM

This invention is derived from the discovery made by the Inventors that, in a completely unexpected manner considering the state of the art set forth above, the compounds of the following general formula X:

X

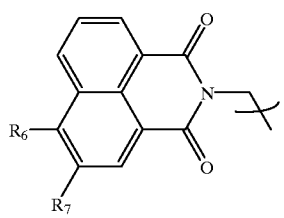

characterized by a gem disubstitution of this carbon with an $R_1$ residue and an alcohol function are powerful inhibitors of metalloproteinase of the extracellular matrix, and more particularly of gelatinase (inhibiting concentration at 50%: C150<200 nM). These compounds also inhibit the release of αTNF from macrophages in mice stimulated by LPS (lipopolysaccharides) (C150: 10 to 0.01 μM) as well as the production of αTGF.

This invention has as its purpose to provide new compounds inhibiting metalloproteinase, and/or the release of αTNF and/or the production of αTGF, the different inhibition activities of $R_6$ represents —H, or a $C_1$ to $C_6$ alkoxy group, or a benzyloxy group, $R_7$ represents —H, or a halogen atom such as —Cl or —Br, $R_1$ represents:
  a $C_3$ to $C_{16}$ linear or branched, or $C_3$ to $C_6$ cyclized alkyl chain, said chain comprising, as the case may be, a heteroatom such as O, S or N,
  a phenoxyalkyl or phenylalkyl group, substituted or unsubstituted, or a heteroarylalkyl group, the alkyl group being $C_2$ to $C_5$, $R_2$ represents:
  a hydrogen atom, or,
  a $C_1$ to $C_5$ alkyl or $C_2$ to $C_5$ alkylidene group, or a hydroxyl, a $C_1$ to $C_6$ alkoxy or a benzyloxy, provided that Y represents —CONHOH when $R_2$ represents a hydroxyl, or a hydroxymethyl, or $C_1$ to $C_6$ alkoxymethyl group, or an arylalkyl group in which the alkyl portion is $C_1$ to $C_6$, an aryloxymethyl group, an arylthiomethyl group, a heteroarylthiomethyl group, in which aryl designates a phenyl remainder, possibly substituted, in particular by —OH, —OCH$_3$, a linear or branched $C_1$ to $C_3$ alkyl group, a halogen such as —Cl or —Br, an amine group such as —NH$_2$, —NHCOCH$_3$, —NHCOOR$_{10}$, $R_{10}$ representing a linear or branched $C_1$ to $C_3$ alkyl group, or A phthalimide alkyl group in which the alkyl portion is $C_1$ to $C_6$, or an alkoxycarbonylmethyl group (alkoxy designating methoxy, ethoxy), a benzyloxycarbonylmethyl, an acetylmethyl, provided that Y represents —SH in these three cases.

AA represents an amino acid, or an amino acid chain, these amino acids being natural or otherwise, and advantageously with an absolute S configuration, in particular an amino acid with the formula these compounds being comparable or even superior to those of compounds of the state of the art described above.

This invention further has as its purpose to provide new medicines containing the aforementioned new compounds as active principle, and offering the advantage of possessing a better bioavailability than the compounds of the state of the art described above.

This invention likewise has as its purpose the use of the aforementioned new compounds for the preparation of new medicines described above, capable of being used in the context of treatment of pathologies in which the metalloproteinase of the extracellular matrix and/or αTNF are involved, as well as pathologies in which an overproduction of αTGF is involved.

This invention has as its subject compounds of the following general formula (X):

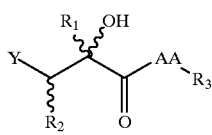

in which:

Y represents:
—CONHOH, or
—SH, or
a group with the formula

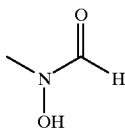

or a group with the formula

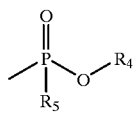

in which:
$R_4$ represents —H, or a $C_1$ to $C_6$ alkyl group, or a phenylalkyl group in which the alkyl group is $C_1$ to $C_6$,
$R_5$ represents a group with the formula

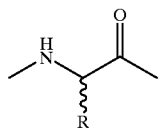

in which R represents:
a $C_1$ to $C_4$ linear or branched alkyl chain,
a —CH$_2$—Y group in which Y represents a ring of 4 to 6 carbon atoms in the ring comprising, as the case may be, one or several heteroatoms such as O, S or N, said ring being aromatic or nonaromatic, substituted as the case may be, in particular by one or several —OCH$_3$, —NO$_2$, —NH$_2$ groups, or by one or several halogen atoms chosen in particular from among —Cl, —Br, —F and —I,
a group with the formula

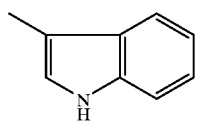

$R_3$ represents a group with the formula —NH—$(R_8)_n$—$R_9$ in which:
n represents 0 or 1,
$R_8$ represents a linear or branched alkyl chain, with 1 to 8 carbon atoms comprising, as the case may be, one or several heteroatoms such as O or S,
$R_9$ represents a hydrogen atom or a methyl, nitrile, morpholino, phenyl, methoxy, hydroxyl, thiomethyl group, or a group with the formula —CH(NH$_2$)=N—OH, or a —N(CH$_3$)$_2$ group.

More particularly, the invention has as its subject the compounds characterized by the following general formula (Xa):

(Xa)

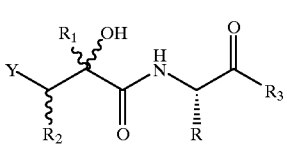

in which:
Y represents —CONHOH,
$R_1$ represents:
—CH(CH$_3$)$_2$,

More particularly, the invention has as its subject, by way of preferred compounds, those a corresponding to the above-noted formulas X or Xa, in which R represents a group with the formula

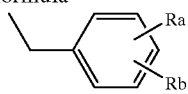

in which $R_a$ and $R_b$ represent a halogen atom, in particular a chlorine atom.

More particularly the invention also has as its subject, by way of preferred compounds, those corresponding to the above-noted formulas X or Xa, in which $R_3$ represents a group with the formula

The invention further has as its subject any mixture comprising, on the one hand, compounds with the following formula (XI.1):

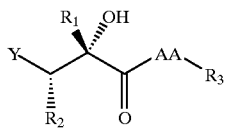

(XI.1)

in which Y, $R_1$ and $R_2$, AA and $R_3$ are such as defined above and, on the other, compounds with the following formula (XI.2):

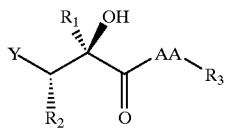

(XI.2)

in which Y, $R_1$ $R_2$, AA and $R_3$ have the meaning indicated hereinabove, the proportion of the compounds (XI.1) and XI.2) in the mixture advantageously being approximately 50% to approximately 99% for the compound of formula (XI.1) and approximately 50% to approximately 1% for the compound of formula (XI.2).

—$CH_2$—$CH(CH_3)_2$,

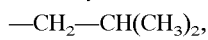

$R_2$ represents:
- an alkyl group with 1 to 5 carbon atoms, in particular a methyl or propyl group,
- a hydroxyl, or
- an alkoxy group with 1 to 5 carbon atoms, in particular a methoxy group, R represents:
- —$C(CH_3)_3$,
- —$CH_2$—$CH(CH_3)_2$,

 group aromatic or nonaromatic, in which $R_a$ and $R_b$, independently of one another, represent —H, —Cl, —Br, —I, —F, —$OCH_3$, —$NO_2$, —$NH_2$, a group with the formula

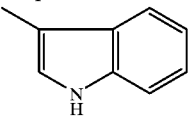

$R_3$ represents a —NH—$(CH_2)_{n1}$—$R_9$ group in which:
$n_1$ represents 0, 1 or 2,
$R_9$ represents —$CH_3$, —C≡N, —$COOCH_3$, —$SCH_3$, —O—$(CH_2)_2OH$, —O—$(CH_2)_2$—$OCH_3$, —$CH(NH_2)$ =N—OH,

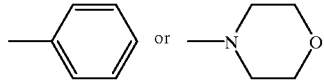

Compounds particularly preferred in the context of this invention are those possessing a stereochemistry such that the $R_1$ and $R_2$ substituents are positioned in anti in relation to the succinic remainder in accordance with the following formula (XI.1):

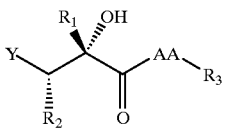

(XI.1)

Compounds particularly preferred in the context of this invention are those corresponding to the following formulas:

Example 13

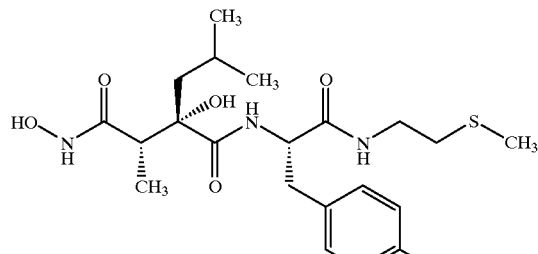

Example 15

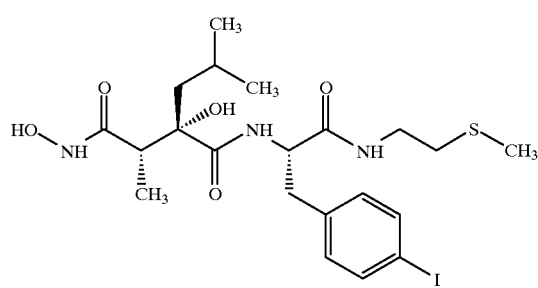

Example 18

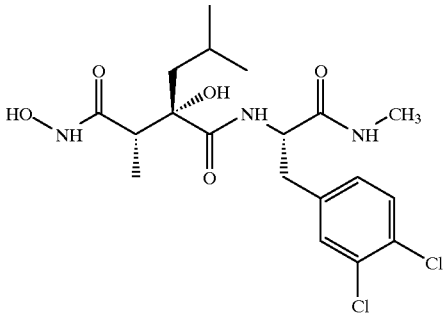

Example 19

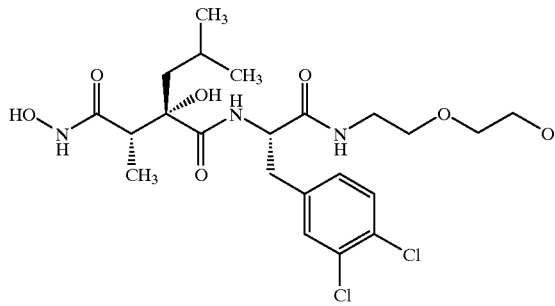

Example 21

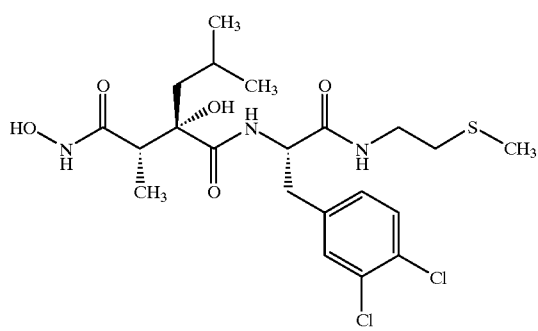

Example 23

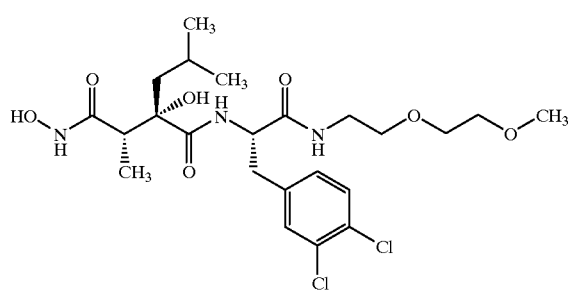

Example 26

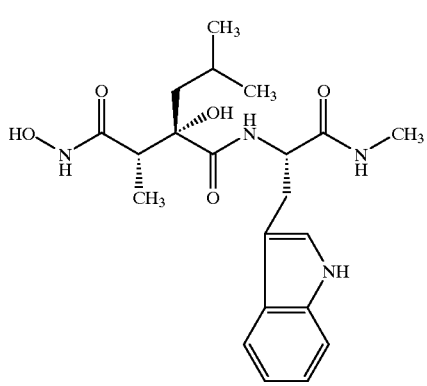

Example 33

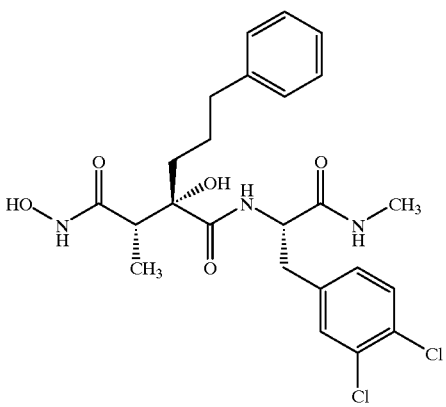

The invention likewise has as its subject any pharmaceutical composition comprising, as an active principle, a compound or compounds and/or a mixture or mixtures such as described hereinabove, in combination with an acceptable pharmaceutical vehicle.

The pharmaceutical compositions according to the invention advantageously are presented in a form which may be administered orally, parenterally or rectally.

The pharmaceutical compositions according to the invention preferably are characterized in that the dosage of active principle is approximately 0.1 to approximately 500 mg/kg/day, preferably from 1 to 300 mg/kg/day orally and rectally, and approximately 0.1 µg/kg/day to 1 mg/kg/day parenterally.

Preferred pharmaceutical compositions according to the invention are presented in a form which may be administered orally, in a unit dosage of 1 mg to 250 mg of active principle per dose, and preferably from 10 mg to 250 mg of active principle per dose, at the rate of 1 to 4 doses per day.

Pharmaceutical compositions also preferred according to the invention are presented in a form which may be administered parenterally, in a unit dosage of 1 µg to 50 mg of active principle per injection, at the rate of 1 to 2 injections per day.

The invention likewise has as its subject the use of a compound or compounds and/or a mixture or mixtures such as described hereinabove, for the preparation of a medicine intended for the treatment of human or animal pathologies in which metalloproteinase, and/or αTNF and/or αTGF are involved.

More particularly, the invention has as its subject the use of a compound or compounds and/or a mixture or mixtures such as described hereinabove, for the preparation of a medicine having the property of inhibiting the action of metalloproteinase involved in the breakdown of the extracellular matrix, such as the collagenase, gelatinase and stromelysine, this medicine being intended for the treatment of human or animal pathologies linked to this action of metalloproteinase, in particular for the treatment of:

rheumatoid arthritis,
osteoarthritis, osteoporosis,
corneal ulceration,
periodontitis,
gingivitis,
tumorous invasions,
metastatic proliferation,
atherosclerosis,
AIDS,
chronic inflammatory diseases of the intestine,
neurodegenerative diseases such as Alzheimer's disease and plaque sclerosis.

More particularly the invention has as its subject the use of a compound or compounds and/or a mixture or mixtures such as described hereinabove, for the preparation of a medicine having the property of inhibiting the release of αTNF from its inactive precursor, this medicine being intended for the treatment of human or animal pathologies in which αTNF is involved, in particular for the treatment of inflammatory, immunological, infectious or malignant pathologies, such as:

rheumatoid arthritis,
Crohn's disease,
plaque sclerosis,
septic shock,
cancer,
cachexia associated with an immunodeficiency.

More particularly the invention has as its subject the use of a compound or compounds and/or a mixture or mixtures such as described hereinabove, for the preparation of a medicine having the property of inhibiting the production of αTGF, this medicine being intended for the treatment of human or animal pathologies in which αTGF is involved, such as:

cancer,
psoriasis,
eczema,
formation of keloids,
diabetic retinopathy,
atherosclerosis,
inflammatory diseases.

Generally speaking, the various pathologies capable of being treated in the context of this invention may be classified in the following manner:

I. Systemic inflammatory response syndrome, including:
  septicemias, in particular Gram positive bacterium, Gram negative bacterium, fungal, or meningococcemia,
  traumatisms and hemorrhages,
  burns,
  exposures to ionizer radiation,
  acute pancreatitis,
  respiratory distress syndrome in adults.
II. Reperfusion injuries, such as reperfusion ischemia.
III. Cardiovascular diseases, such as:
  myocardial infarction,
  congestive heart failure.
IV. Infectious diseases, including:
  AIDS,
  meningitis,
  hepatitis,
  arthritis,
  periarthritis,
  pneumonia,
  epiglottitis,
  0157:H7 E. Coli infection,
  hemolytic uremic syndrome,
  thrombolytic thrombocytopenic purpura,
  malaria,
  hemorrhagic dengue,
  leishmaniasis,
  leprosy,
  septic shock,
  streptococcal myositis,
  gas gangrene,
  tuberculosis,
  orchitis,
  legionnaires' disease,
  lyme disease,
  influenza,
  infectious mononucleosis in Burkitt's lymphoma,
  cancer of the rhinopharynx,
  viral encephalitis.
V. In obstetrics, gynecology, including:
  premature labor,
  miscarriage,
  sterility.
VI. Autoimmune inflammatory diseases, including:
  rheumatoid arthritis and the seronegative arthropathies,
  osteoarthritis,
  Crohn's disease, ulcerative colitis,
  lupus erythematosus,
  iridocyclitis, uveitis and inflammation of the optic nerve,
  idiopathic pulmonary fibrosis,
  systemic vascularitis and Wegener's granulomatosis,
  sarcoidosis,
  orchitis.
VII. Allergic and atopic diseases, including:
  asthma,
  allergic rhinitis
  eczema,
  allergic contact dermatitis,
  allergic conjunctivitis,
  hypersensitivity pneumonitis.
VIII. Malignant diseases, including:
  acute lymphoblastic leukemia,
  acute monocytic leukemia,
  chronic myeloid leukemia,
  chronic lymphocytic leukemia,
  Hodgkin's disease,
  myeloid splenomegaly,
  Kaposi's sarcoma,
  colorectal carcinoma,
  malignant histiocytosis,
  paraneoplastic syndrome and hypercalcemia in malignant diseases,
IX. Transplants, including:
  graft rejection
  reaction of the graft against the host
X. Cachexia
XI. Congenital diseases, including:
  mucoviscidosis,
  familial lymphohistiocytosis,
  sickle-cell anemia
XII. Dermatological diseases, including:
  psoriasis,
  alopecia.

XIII. Neurological diseases, including:
   plaque sclerosis
   headaches.
XIV. Kidney diseases, including:
   nephritic syndrome,
   hemodialysis,
   uremia.
XV. Toxic treatments, including:
   OKT3 therapy,
   anti-CD3 therapy,
   cytokine therapy,
   chemotherapy,
   radiotherapy,
   chronic salicylate poisoning.
XVI. Idiopathic, metabolic diseases, including:
   Wilson's disease,
   hemochromatosis,
   α1-antitrypsin deficiency,
   diabetes,
   Hashimoto's thyroiditis,
   osteoporosis.

The invention also has as its subject the processes for preparation of the compounds or mixtures described hereinabove, and forming the subject of the description which follows.

The abbreviations used in the description of the preparation processes of the invention and the detailed description of the experimental portion hereinafter, are the following:

| | |
|---|---|
| AcOEt | Ethyl acetate |
| α AD-mix | Asymmetric dihydroxylation α mixture |
| β AD-mix | Asymmetric dihydroxylation β mixture |
| Ar | Aromatic |
| Buli | Butyl lithium |
| $CH_2Cl_2$ | Dichloromethane |
| DCC | Dicyclohexyl carbodiimide |
| DIPEA | Diisopropyl ethylamine |
| DMF | Dimethylformamide |
| $Et_2O$ | Diethyl ether |
| HMPT | Hexamethylphosphoretriamide |
| HOBT | Hydroxybenzotriazole |
| LDA | Lithium diisopropyl amidide |
| LHMSA | Lithium hexamethyldisyl amidide |
| MeOH | Methanol |
| $Na_2SO_4$ | Sodium sulfate |
| $NEt_3$ | Triethylamine |
| PyBop | Tris pyrrolidino benzotriazolyl oxyphosphonium, hexaflurophosphate |
| tBuOH | Tert-butanol |
| THF | Tetrahydrofuran |
| THP | Tetrahydropyran |
| TMSCl | Trimethylsilyl chloride |
| Tos | Paratoluenesulfonate |
| WSC | Water-soluble carbodiimide |

The compounds according to the invention in which Y is a CONHOH group (also designated hereinafter as compounds of formula XV) may be obtained according to the following Diagram I:

Diagram 1

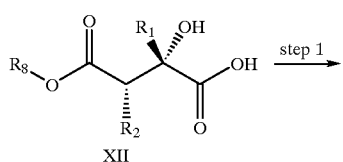

XII

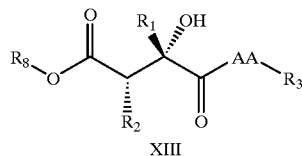

XIII

|step 2

XIV

|step 3

XV in which:

step 1 consists in condensing α-hydroxysuccinic acid XII (where $R_8$ is a protective group compatible with the various elements of the molecule such as t-butyl or benzyl) with an $AA-R_3$ remainder where AA and $R_3$ are such as defined previously, by a method of coupling used in peptide synthesis and preferably PyBop at room temperature for 1 to 24 hours (in the case where $R_2$=OH, the alcohols may be protected beforehand with, for example, a silyl derivative).

step 2 consists in hydrolyzing the ester XIII obtained in the preceding step into carboxylic acid XIV with trifluoroacetic acid, in particular at room temperature in a solvent such as $CH_2Cl_2$ for 1 to 10 hours when $R_8$ is t-butyl, or in hydrogenolyzing the ester XIII into acid XIV with, for example, $H_2$ Pd/C when $R_8$ is benzyl (in particular under atmospheric pressure in a polar solvent such as ethanol for 30 minutes to 10 hours), in step 3, hydroxamic acid XV is formed by reaction of hydroxylamine, protected O hydroxylamine or diprotected N,O hydroxylamine, preferentially with O—THP hydroxylamine or O-benzyl hydroxylamine (when $R_2$ is other than alkylidene, aryloxymethyl and heteroarylthiomethyl) in the presence of a coupling reagent such as DCC/HOBT or WSC/HOBT at room temperature in a solvent such as THF, $CH_2Cl_2$, or DMF for 1 to 24 hours (when $R_2$=OH, the alcohols are protected beforehand with, for example, TMSCl); the (di)protected O or N—O hydroxylamines then are deprotected according to the nature of the protective group, for example in an acid medium for O—THP hydroxylamine (in particular at room temperature in a THF—$H_2O$ mixture for 1 to 24 hours) or $H_2$ Pd/C for O-benzyl hydroxylamine (in particular under atmospheric pressure in a polar solvent such as ethanol for 30 minutes to 10 h.).

The compounds XIV and XV also may be obtained when $R_2$ is other than heteroarylthiomethyl and $R_1$ other than heteroarylalkyl through the reactions of the following Diagram 2:

Diagram 2

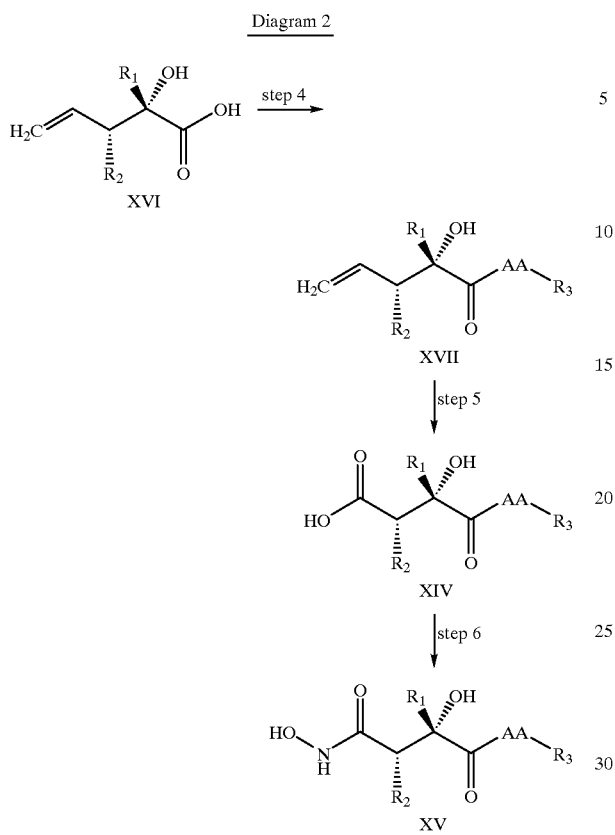

in which:

steps 4 and 6 are performed as in steps 1 and 3 of diagram 1 respectively, and starting from compounds XVI and XIV, which leads to the compounds of formula XVII and XV respectively, step 5 consists in oxidizing the double ethylene bond of the compound of formula XVII into acid, in particular by ozonolysis (for example at −60° C. in $CH_2Cl_2$ until obtaining a steady blue color), then oxidation (in particular at room temperature with $NaClO_2$ and $NaH_2PO_4$ in tBuOH—$H_2O$ for 15 hours) or directly by $KMnO_4$/$NaIO_4$ (in particular at room temperature in a tBuOH—$H_2O$ mixture for 1 to 10 hours), which leads to the compound of formula XIV.

The compounds XIV and XV also may be prepared according to the sequence of reactions (except $R_2$=OH, alkoxy or benzyloxy) of the following Diagram 3:

Diagram 3

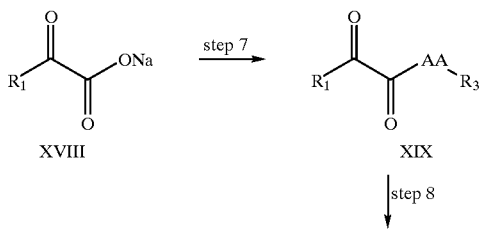

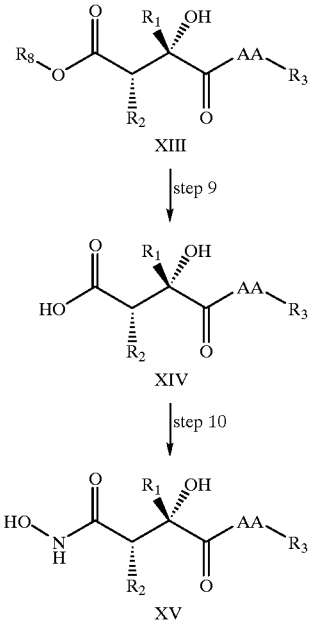

in which:

steps 9 and 10 are identical to steps 2 and 3 of Diagram 1 and are performed starting from compounds XIII and XIV respectively, which leads to compounds XIV and XV respectively, step 7 consists in reacting the sodium salt of a ketoacid XVIII with AA-$R_3$ by means of a coupling agent, for example oxalyl chloride with DMF at room temperature for 1 to 10 hours.

step 8 consists in a Reformatsky reaction (Rathke, Org. Reac. 22, 423–460, 1975) between compound XIX and a bromo-ester with the formula:

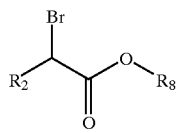

(in which $R_2$ and $R_8$ are the very same as before) in the presence of zinc (in particular in a benzene-diethyl ether mixture, at 80° C. for 1 hour 30 minutes); this reaction leads to a mixture of stereoisomers which may be separated, for example, by a chromatographic method to produce compounds XIII.

The succinic acids XII may be prepared by Reformatsky reaction performed as previously according to the following Diagram 4 between, on the one hand, a compound with the formula $R_2$—CHBr—CO—$OR_8$ in which $R_2$ is such as defined above (except $R_2$=OH, alkoxy, benzyloxy) and $R_8$ is such as defined hereinbelow and, on the other, a compound of formula XX in which $R_1$ is such as defined hereinabove, and $R_9$ is such as defined hereinbelow:

Diagram 4

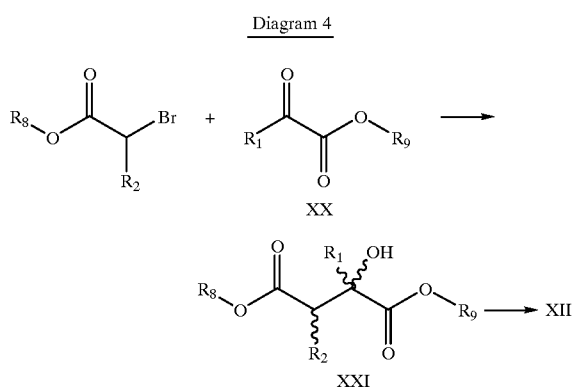

in which $R_8$ and $R_9$ are carboxylic acid protective groups which may be cleaved selectively: $R_9$ may be, for example, a benzyl remainder sensitive to catalytic hydrogenolysis and $R_8$ a saponifiable ethyl or t-butyl group sensitive to acid hydrolysis.

Under these conditions, the reaction produces a mixture of the four diastereoisomers of formula XXI which may be separated, for example, by a chromatographic method to produce compounds XII).

The compounds XII also may be obtained through Evans oxazolidinones (J. Am. Chem. Soc. 104, 1737–1739, 1982; J. Am. Chem. Soc. 112, 8215–8216, 1990) according to the sequence of reactions (except $R_2$=OH, alkoxy or benzyloxy) of the following Diagram 5:

Diagram 5

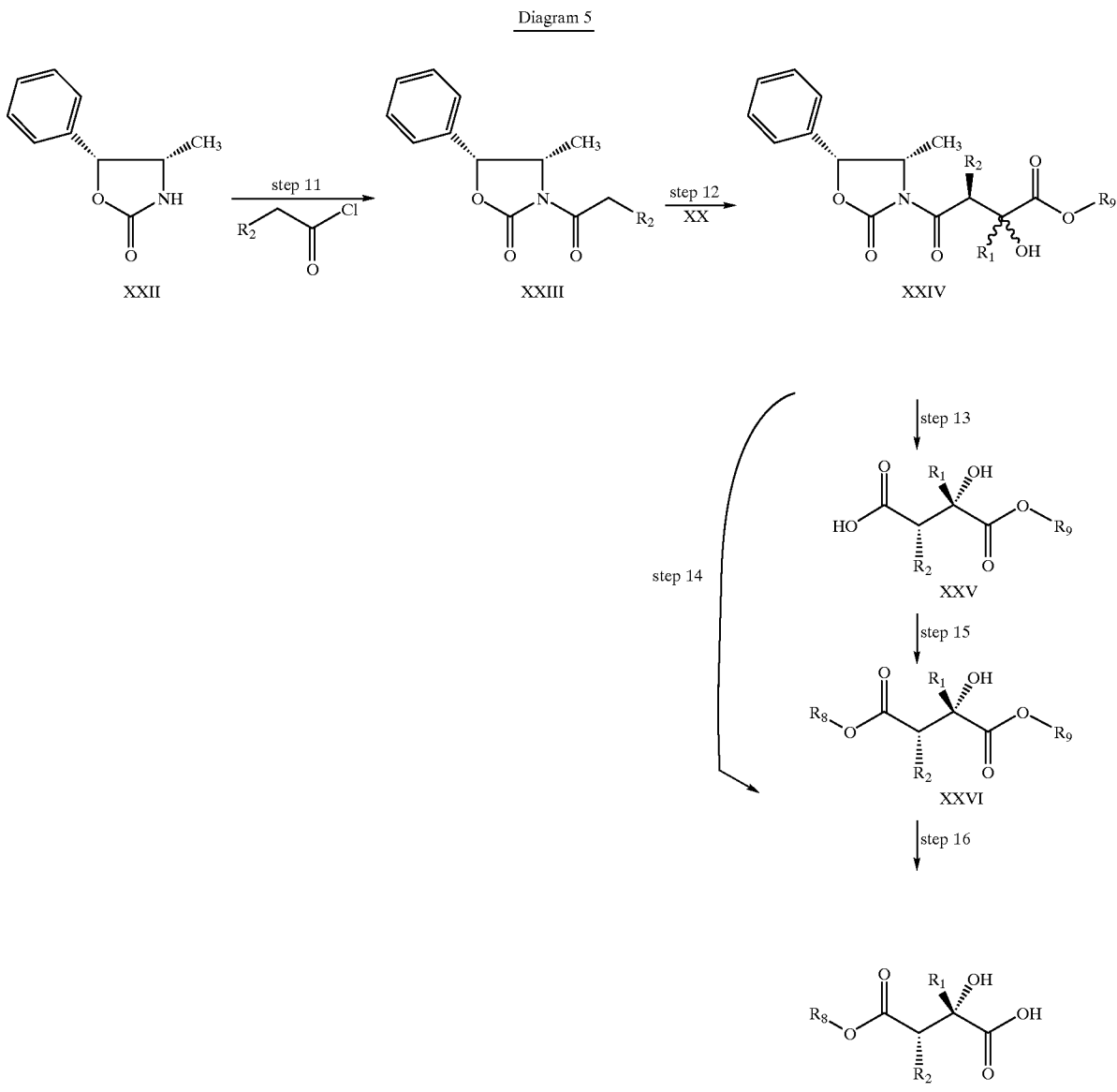

in which:

step 11 consists in acylating the oxazolidinone XXII previously treated with BuLi (in particular at −70° C. in THF) or with NaH (in particular at 0° C. in THF) with an acid chloride

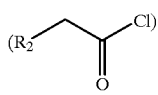

(in particular at room temperature for 15 hours), in which $R_2$ is such as defined above, step 12 consists in condensing the enolate of the derivative XXII (prepared through the action of a base, for example LDA, LHMSA at −60° C. in THF for 30 minutes or a Lewis acid, for example $TiCl_4$ at 0° C. in $CH_2Cl_2$ for 1 hour) with a ketoester XX, in particular at −60° C. in THF or $CH_2Cl_2$ for 2 hours, $R_9$ being a carboxylic acid protective group (chiral or otherwise) compatible with the following step; under these conditions, the reaction leads to a mixture of stereoisomers which may be separated, for example, by a chromatographic method, step 13 consists in cleaving the chiral copula of the compound XXIV with an aqueous base, for example aqueous KOH (2N) compatible with $R_9$ or with LiOOH (prepared from $LiOH+H_2O_2$) so as to obtain carboxylic acid XXV, in particular in a THF—$H_2O$ mixture at room temperature for 1 hour 30 minutes.

step 14 consists in cleaving the copula of compound XXIV with an organic base, for example MeOMgBr, LiOBr, in particular in THF at 0° C. for 1 hour 30 minutes, compatible with $R_9$ so as to obtain the ester directly, step 15 consists in protecting the carboxylic acid of compound XXV with an $R_8$ protective group; $R_8$ and $R_9$ must be able to be cleaved selectively, for example $R_8$=t-butyl (isobutene in $CH_2Cl_2$ in the presence of a catalytic quantity of acid such as sulfuric acid at room temperature in a closed receptacle for 1 to 24 hours) and $R_9$=benzyl ($K_2CO_3$ in acetonitrile in the presence of a benzyl halogenide at 80° C. for 1 to 10 hours).

step 16 consists in hydrolyzing the $R_9$ protective group of the compound XXVI either in a basic medium, for example aqueous NaOH or in an acid medium, for example trifluroacetic acid, or in hydrogenolyzing, for example $H_2$ Pd/C, depending on the $R_9$ structure, so as to obtain succinic acids in the same manner as before.

A method for obtaining the compounds of structure XVI consists in performing an aldolization reaction from a ketoester XXVII and an alkene XXVIII (in particular in the presence of a Lewis acid such as $SnCl_4$ at −80° C. in a solvent such as $CH_2Cl_2$ for 5 minutes to 2 hours), or from a keto-acid (in the form of sodium salt or triethylamine) XXX and an alkene XXXI (in particular at room temperature between 1 and 10 hours in a THF—$H_2O$ mixture) according to the following Diagram 6:

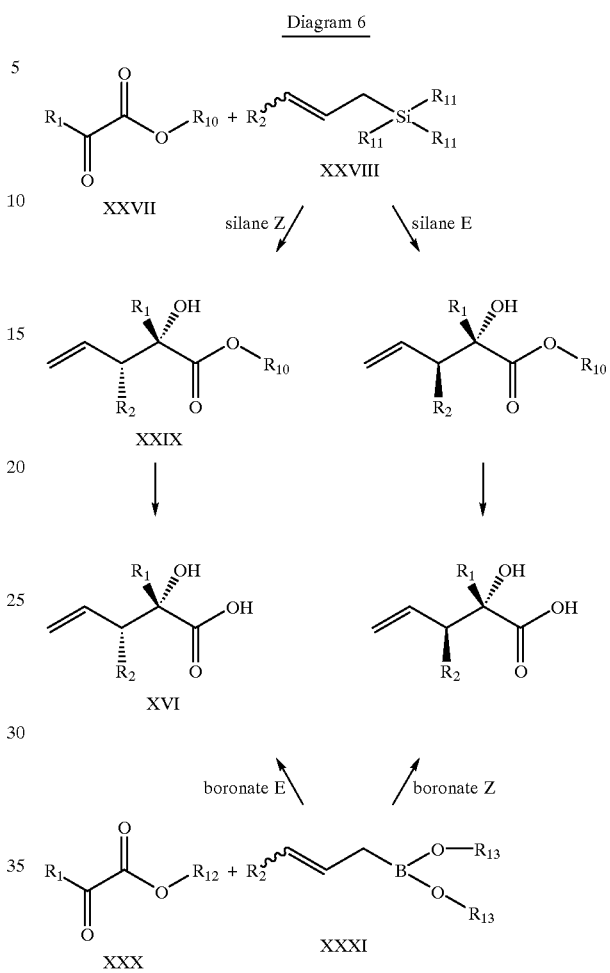

in which:

$R_1$ and $R_2$ have the same meaning as in Diagram 2, $R_{10}$ is a possibly branched $C_1$–$C_{12}$ alkyl, a benzyl or an optically pure compound such as mandelic acid esterified with a linear or branched $C_1$–$C_3$ alkyl, or a benzyl, $R_{11}$ is a linear or branched $C_1$–$C_3$ alkyl, or a chlorine, $R_{12}$ is sodium or triethylamine, $R_{13}$ is hydrogen, a linear or branched $C_1$–$C_3$ alkyl; $R_{13}$ also may represent a chain forming a ring with the boron atom such as, for example, di-isopropyltartrate, the reactions are diastereoselective and lead to stereochemistry derivatives XVI if the double bond is of Z geometry for the compounds XXVIII and E geometry for the compounds XXXI.

A more particularly preferred method consists in adopting as an $R_{10}$ substituent an optically pure compound such as ethyl ester mandelic acid, which makes it possible to obtain optically pure compounds XVI.

The compounds XXIX and XVI also can make it possible to obtain acid XII according to the following reaction Diagram 7:

Diagram 7

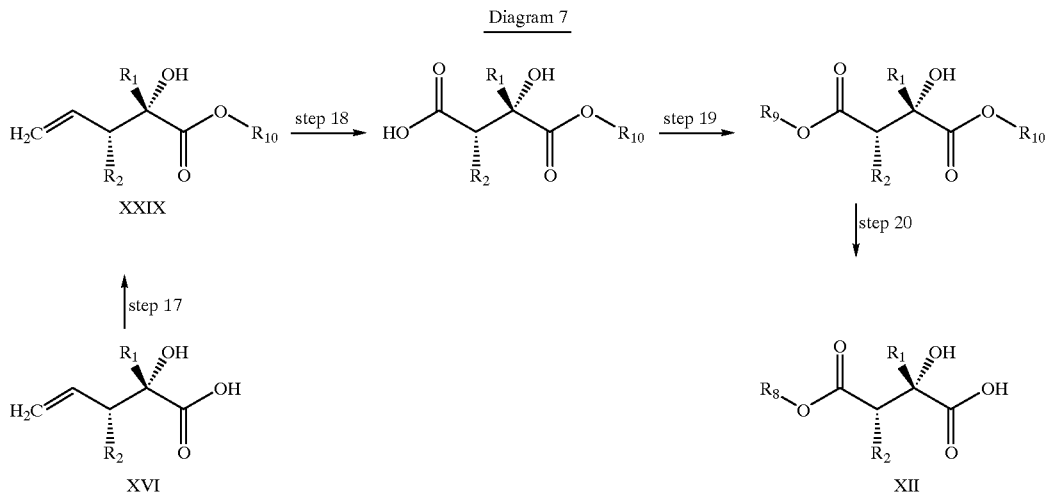

in which:

step 17 consists in esterifying the compound XVI so as to obtain one of the compounds XXIX, for example a benzyl or mandelic ester with PyBop, step 18 consists in oxidizing the double bond of the compound XXIX in a manner identical to step 5 of Diagram 2, step 19 consists in protecting the carboxylic acid with an $R_9$ group compatible with the deprotection of the $R_{10}$ group, for example $R_9$ is t-butyl when $R_{10}$ is ethyl mandelate, step 20 consists in deprotecting the acid bearing $R_{10}$ in a manner identical to step 16 of Diagram 5, which leads to the obtaining of the compound of formula XII.

The keto-acids or esters XX, XXVII, XXX, when they are not commercially available, may be prepared through the following reaction Diagram 8:

Diagram 8

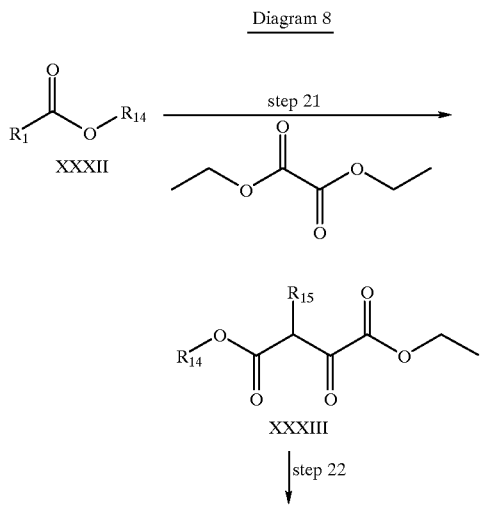

-continued

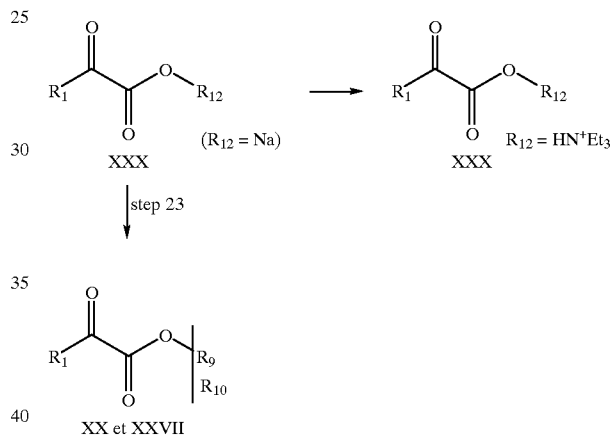

$R_{14}$ is a linear or branched $C_1$–$C_3$ alkyl, $R_{15}$ is $R_1$ less one carbon, $R_9$, $R_{10}$ and $R_{12}$ are as before, step 21 consists in reacting the corresponding ester in the presence of a base, for example tBuOK, diethyl oxalate (addition of diethyl oxalate to tBuOK, in diethyl ether, at t<10° C., then addition of the ester at room temperature and stirring at this temperature for 15 hours), step 22 consists in hydrolyzing the esters in heated condition in an acid medium, for example sulfuric acid 5N, then neutralizing with a base, for example soda, to obtain the product XXX ($R_{12}$=Na$^+$), the compound XXX ($R_2$=HN$^+$Et$_3$) is easily obtained through treatment of the sodium salt with triethylamine hydrochlorate, step 23 consists in esterifying the compound XXX ($R_{12}$= Na$^+$) through the conventional methods of esterification, for example oxalyl chloride, DMF.

The silyl derivatives XXVIII with Z geometry may be obtained according to the following Diagram 9:

Diagram 9

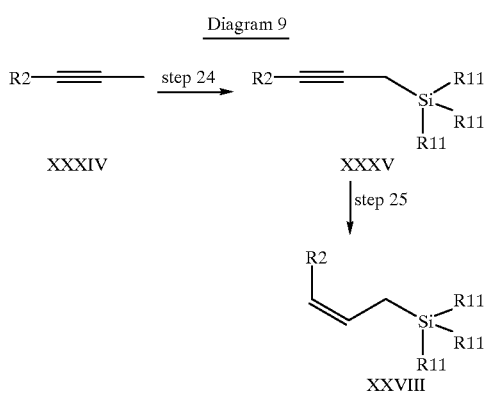

in which:
- $R_2$ is such as described in Diagram 2,
- $R_{11}$ is such as described above,
- step 24 consists in performing an alkylation of an alkyne by means of a base, for example t-Buli (in particular in diethyl ether at −70° C.), with $ClSi(R_{11})_3$ (in particular at −70° C. in diethyl ether, then at room temperature between 5 and 45 minutes),
- step 25 consists in reducing the triple bond to a double bond through a reducing agent such as hydrogen in the presence of a catalyst such as Nickel acetate/NaBH4 in ethanol at atmospheric pressure for 2 hours.

Another method for obtaining the XXVIII derivative ($R_2=CH_3$) is described hereinbelow in Diagram 10:

Diagram 9

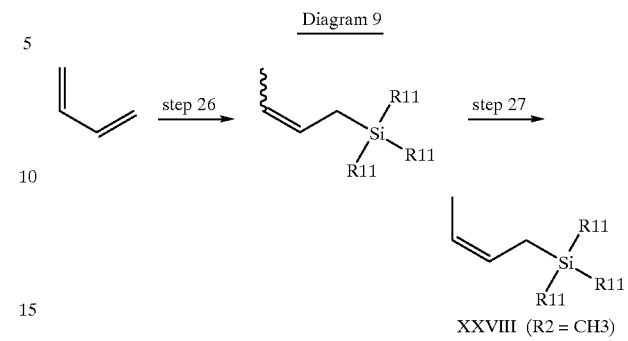

in which:
- $R_{11}$ is such as described before,
- step 26 consists in reacting an alkylsilane with butadiene in the presence of triethylaluminum and Ni acetylacetonate in a closed receptacle, in particular at 60° C. for 5 to 20 hours,
- the compound obtained is an E+Z mixture,
- step 27 consists in isomerizing the double bond by heating then distilling the product.

The hydroxamic acids for which $R_2=OH$ or alkoxy or benzyloxy may be obtained according to the following Diagram 11:

Diagram 11

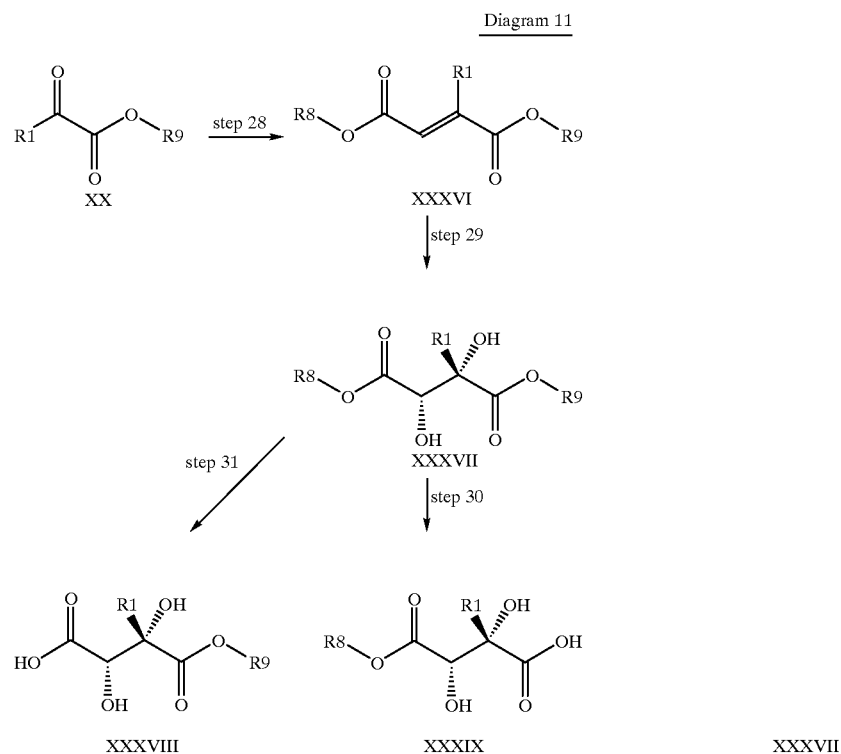

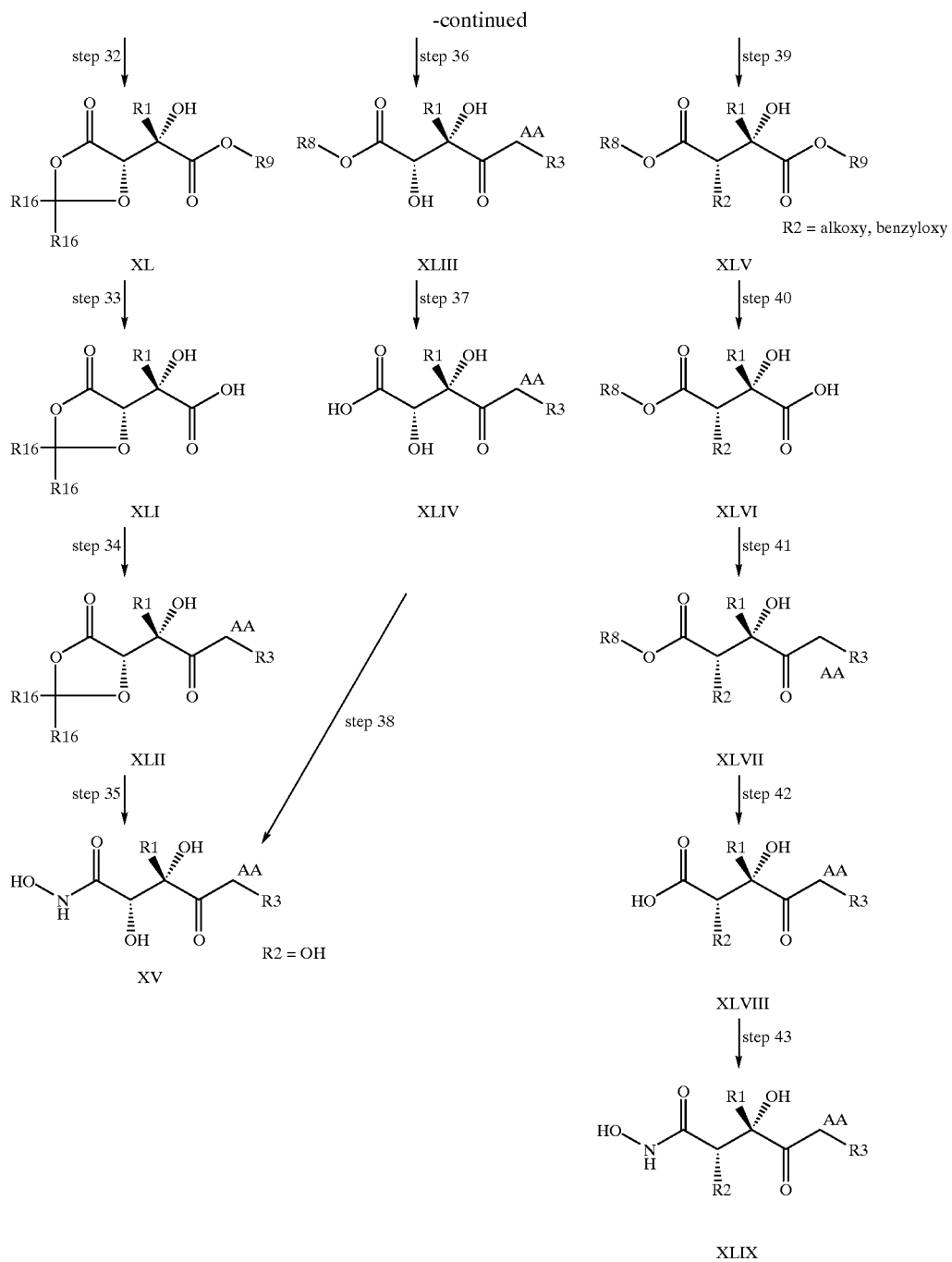
in which:
- $R_1$, $R_8$, $R_9$ are such as described in Diagram 4 except when $R_2$=benzyloxy, $R_8$ and $R_9$ cannot be cleaved by hydrogenolysis;
- $R_{16}$ is linear or branched $C_1$–$C_5$ alkyls or represents a chain and forms a ring with the two oxygen atoms,
- step 28 consists in performing a Wittig reaction between the compounds XX and a phosphonium salt with the structure:
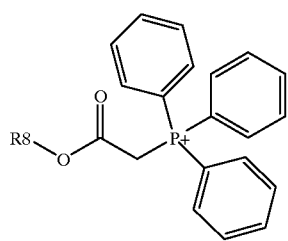

(X being a halogen) in DMF at room temperature for 1 to 10 hours or a phosphonate with the structure

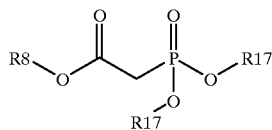

$R_{17}$ being a linear or branched $C_1$–$C_3$ alkyl, this reaction making it possible to lead to a mixture of E and Z alkenes which must be separated, for example by a chromatographic method, so as to obtain a compound XXXVI of E geometry, step 29 consists in performing a Sharpless asymmetric hydroxylation (Chem. Rev. 2483–2547, 1994) in the presence of βAD-mix and methanesulfonamide, in particular in a tBuOH—H$_2$O mixture at room temperature for 1 to 10 hours; this reaction leads to an optically pure product; the use of α or βAD-mix on alkene Z leads to two other diastereoisomers, step 30 is identical to step 16 of Diagram 5, step 31 consists in hydrolyzing the ester into carboxylic acid in a basic or acid medium depending on the structure of $R_8$, step 32 consists in protecting the α-hydroxyacid in the form of dioxolane by reacting it with an acetal, for example 2,2-dimethoxypropane in DMF at 50° C., 15 hours, step 33 consists in deprotecting the ester by hydrogenolysis; the $R_9$ in this case is exclusively of benzyl type to be compatible with the dioxolane which does not tolerate the aqueous basic or acid medium, step 34 consists in coupling the AA-R$_3$ amino acid by a method compatible with dioxolane, for example PyBop as before;

step 35 consists in substituting hydroxylamine for the dioxolane in an MeOH—H$_2$O mixture at −20° C. for 1 to 15 minutes, steps 36, 37 and 38 are identical to steps 1, 2 and 3 of Diagram 1, step 39 consists in alkylating the secondary alcohol by reacting it with a base, for example NaH, then an electrophile, for example an alkyl or benzyl halogenide, in particular in THF at room temperature for 1 to 10 hours, step 40 is identical to step 16 of Diagram 5, steps 41, 42 and 43 are identical to steps 1, 2 and 3 of Diagram 1.

The compounds according to the invention in which Y=SH,

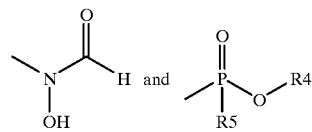

may be obtained according to the following Diagram 12:

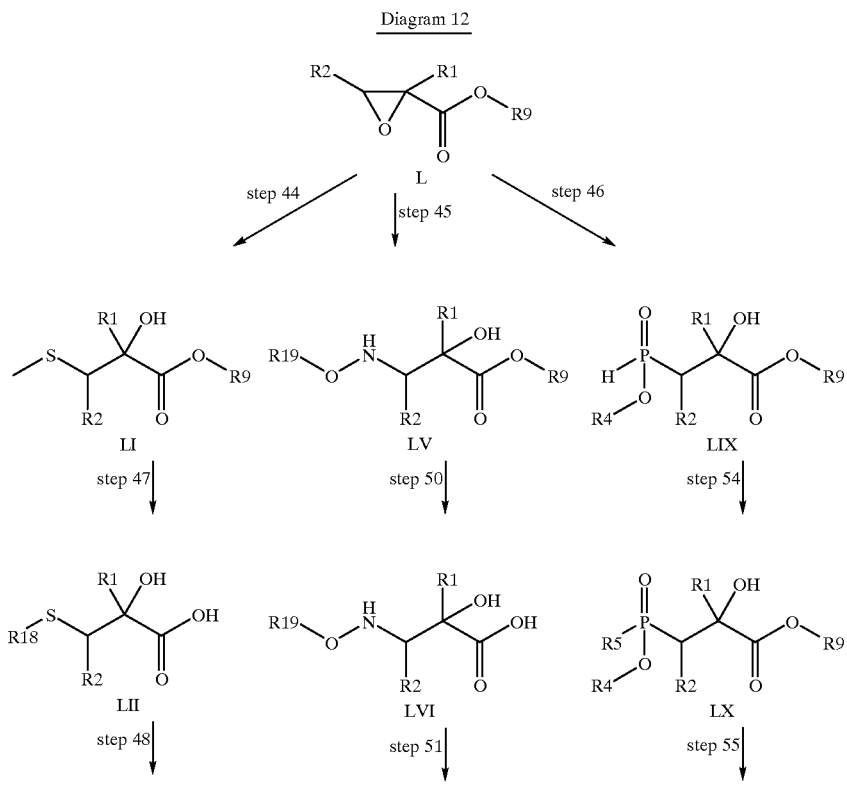

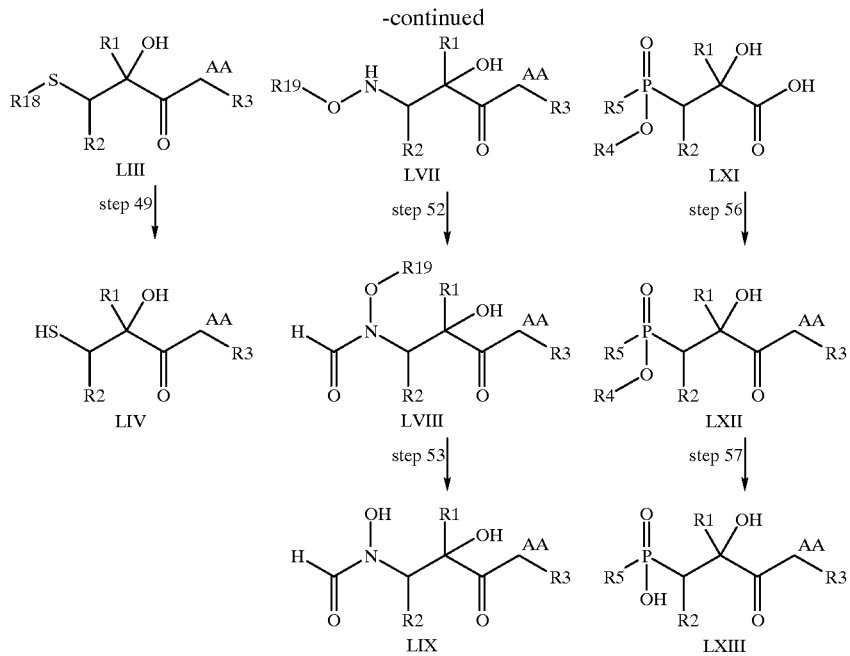

in which:

step 44 consists in opening an epoxide of formula L in which $R_1$ and $R_2$ are such as defined hereinabove, and $R_9$ is a carboxylic acid protective group, in particular a benzyl remainder sensitive to catalytic hydrogenolysis, this opening of the epoxide L being accomplished with a nucleophile, for example a thiol protected by an $R_{18}$ group compatible with $R_9$, for example a benzyl in methanol for 1 hour at 60° C., step 47 consists in deprotecting the ester LI, for example with trifluroacetic acid as before, step 48 is identical to step 1 of Diagram 1, and performed starting from compound LII obtained in the preceding step, step 49 consists in deprotecting the sulfur, for example with sodium in liquid ammonia, in particular at −60° C. for 5 to 15 minutes, step 45 consists in opening the epoxide L with protected hydroxylamine such as defined previously, for example $R_{19}$=benzyl or THP as previously, step 50 consists in deprotecting the LV ester by a method compatible with $R_{19}$.

step 51 is identical to step 48 and performed starting from the compound LVI obtained in the preceding step, step 52 consists in reacting the hydroxylamine LVII with formic acid and acetic anhydride, in particular at a temperature of at least 100° C. for 1 to 15 hours, step 53 consists in cleaving $R_{19}$ on the compound LVIII with, for example, $H_2$ Pd/C or HCl 1N depending on the structure of $R_{19}$ as before, step 46 consists in opening an epoxide L with hypophosphorous acid with the formula $H_3PO_2$, then esterification with a coupling agent such as DCC and an $R_4OH$ group in which $R_4$ is such as defined hereinabove, in the presence, for example, of trimethylorthoformate and tetramethylguanidine at room temperature for 5 hours, step 54 consists in treating the compound LIX with a compound with the formula:

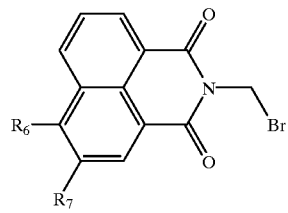

(prepared according to the methods described in the literature) in which $R_6$ and $R_7$ are such as defined hereinabove, in particular in $CH_2Cl_2$ in the presence of bis trimethylsilyl acetamide at room temperature for 5 hours, which leads to the obtaining of the compound of formula LX in which $R_5$ represents:

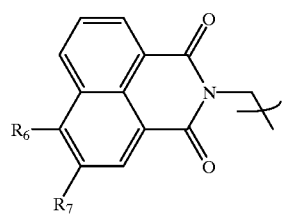

step 55 consists in cleaving the $R_9$ ester by a method compatible with $R_4$ as previously, step 56 is identical to step 48, and performed starting from the compound LXI obtained in the preceding step, step 57 consists in cleaving the $R_4$ group of the compound LXII obtained in the preceding step, for example with the aid of NaI in acetone under reflux for 15 hours.

The compounds of Diagram 12 are mixtures of diastereoisomers or optically pure, depending on the original compound L. The mixtures of diastereoisomers may be separated, for example, by a chromatographic method.

Preparation of the compounds L in a racemic manner according to the following Diagram 13:

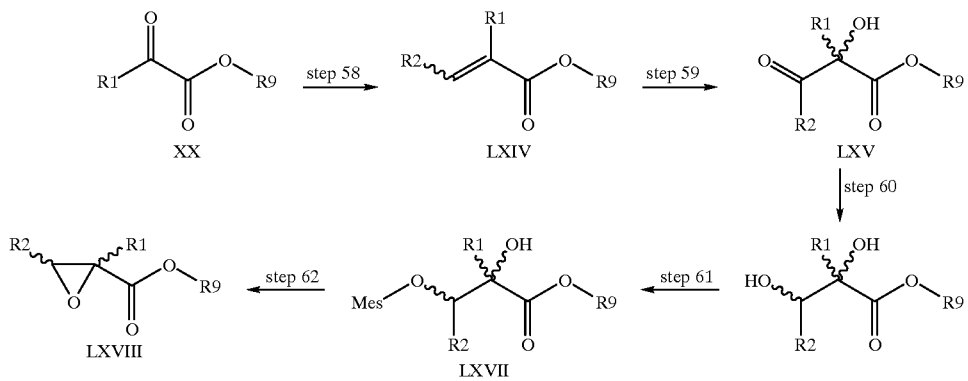

in which:
R₁, R₂, R₉ are such as described previously,
step 58 consists in performing a Wittig reaction between a phosphonium salt

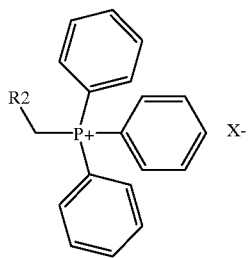

($R_2$ and $X^-$ are the very same as before) and the compound XX in the presence of a base, for example BuLi in THF at a temperature ranging between 0° C. and 60° C. for 1 hour; the olefin LXIV obtained is an E and Z mixture which may be separated, for example, by a chromatographic method.

step 59 consists in oxidizing the double bond with, for example, $KMnO_4$-acetic acid in acetone at a temperature of −10° C. for 1 hour 30 minutes.

step 60 consists in reducing the carbonyl with a reducing agent, for example $NaBH_4$ in ethanol at 0° C. for 15 minutes, step 61 consists in transforming the secondary alcohol into a starter group by reacting it with, for example, methane-sulfonic acid in the presence of a base, for example $NEt_3$ in diethyl ether at 0° C. for 1 hour, step 62 consists in treating the compound LXVIII with a base, for example NAH, to form epoxide in DMF at room temperature for 1 to 3 hours.

The olefin LXIV with E geometry also may be obtained through reactions of the following Diagram 14:

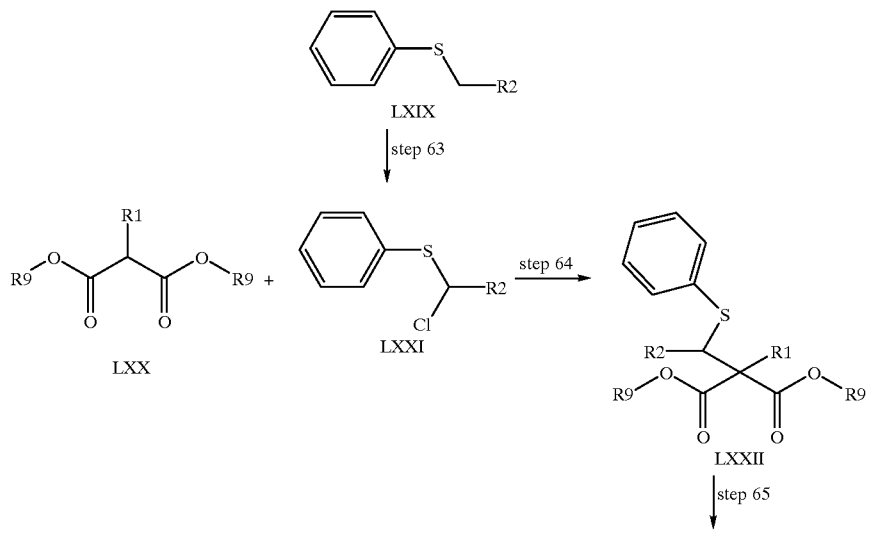

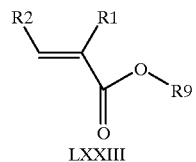

LXXIII in which:

step 63 consists in performing a chloration of the compound LXIX with, for example, sulfuryl chloride in dichloromethane at 35° C. for 30 minutes.

step 64 consists in performing an alkylation in the presence of a base, for example NaH in a THF—HMPT mixture at room temperature for 15 hours, step 65 consists in carrying out a dealcoxycarbonylation followed by an elimination with, for example, LiCl by heating in a solvent such as DMF, DMSO or HMPT. The product obtained under these conditions has E geometry.

Preparation of optically pure epoxide according to the following diagram 15:

Diagram 15

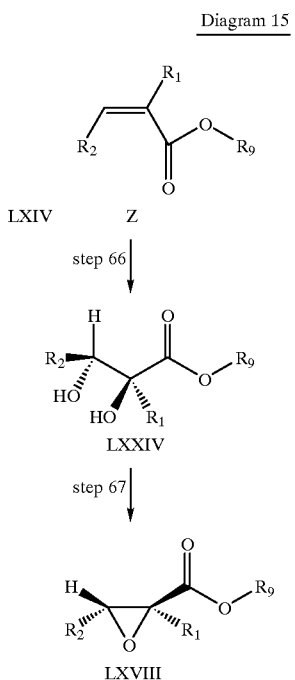

in which:

step 64 consists in performing an asymmetric dihydroxylation as before with the aid of βAD-mix to lead to the compound LXXIV; the enantiomer may be obtained by αAD-mix and the other two diastereoisomers starting from E olefin and β or αAD-mix.

step 67 is identical to steps 61 and 62 of Diagram 13.

Experimental Portion

Intermediary 1: 2(S*) hydroxy-2 (S*)-(3-methylpropyl) 3 (R*) methyl pent-4-enoic acid

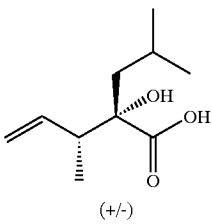

(+/-)

Method A a) (E)-but-2-enyl boronic bis (methyl-2-propyl ester) acid

To 23.8 g (212 mmoles) of tBuOK in 175 ml of dry THF cooled to −78° C., add 21 ml (230 mmoles) of trans-2-butene. Then add in 1 hour 30 minutes, 98 ml (212 mmoles) of nBuli (2.45 M in hexane). At the end of addition, stir for ½ hour at −50° C. Cool to −78° C. and add 49 ml (212 mmoles) of triisopropyl borate, stir for ½ hour.

Add 200 ml of N HCl saturate with NaCl. Extract with 4 times 200 ml of ethyl ether. Collect the ethereal phases, dry over sodium sulfate.

Add 35.8 ml (467 mmoles) of isopropyl alcohol, 66 g of anhydrous sodium sulfate and stir for 1 night at room temperature.

Decant the inorganic, evaporate the ether at 30° C. in the rotary evaporator (under vacuum). Recover 17.95 g of oil or 45%. To be preserved under nitrogen: Eb: 30° C./0.3 mmHg.

RMN (CDCl$_3$): δ5.5 (m, 2H, C$\underline{H}$+C$\underline{H}$); 4.4 (m, 2H, OC$\underline{H}$—(Me)$_2$); 1.7 (m, 5H, C$\underline{H}_3$—CH═ and ═CH—C$\underline{H}_2$—B; 1.3 (m, 12H, O—CH—(C$\underline{H}_3$)$_2$).

b) 2(S*)hydroxy-2(S*) 3-methylpropyl 3 (R*) methyl pent-4-enoic acid

Disperse 3.77 g (24.8 mmoles) of 4-methyl-2-oxo-sodium pentanoate in 30 ml of CH$_2$Cl$_2$. Add 30 ml of HCl N saturated with NaCl. Extract 3×15 ml of CH$_2$Cl$_2$. Collect and dry the organic phases over Na$_2$SO$_4$. Filter and introduce this solution into a 250-ml three-necked flask.

Cool at −25° C., add 3.48 ml (24.8 mmoles) of triethlamine, then add 4.57 g (24.8 mmoles) of product a) and stir for one night at room temperature. Pour over HCl 6N, extract with CH$_2$Cl$_2$, dry over Na$_2$So$_4$. Filter. Evaporate.

Purify by flash chromatography on 200 g of silica (eluant: CH$_2$Cl$_2$:MeOH; 95:5).

Recover 2.73 g of white solid (yield 60%).

P.F.: 86° C.

IR (CDCl$_3$): ν CO: 1706 cm$^{-1}$; ν C═C: 1639 cm$^{-1}$

RMN (CDCl$_3$): δ5.8 (m,1H, CH$_2$═C$\underline{H}$); 5.15 (m, 2H, C$\underline{H}_2$═CH—); 2.5 (m, 1H, ═CH—C$\underline{H}$(CH$_3$)—); 1.75 (m, 3H, C$\underline{H}_2$—C$\underline{H}$—(CH$_3$)$_2$); 1 (3d, 9H, C$\underline{H}_3$).

Method B

To 4.8 g (42.7 mmoles) of tBuOK in 35 ml of THF at −78° C., add 4.2 ml (45.2 mmoles) of trans-2-butene. Without exceeding −65° C., add 21.35 ml (42.7 mmoles) of nBuli 2 M in hexane in 1 hour. At the end of addition, stir for ½ hour at −50°C., then cool again to −78° C. and add 9.85 ml (42.7 mmoles) of triisopropyl borate and stir for 30 minutes at −78° C.

Solubilize 6.49 g (42.7 mmoles) of 4-methyl-2-sodium oxovalerate in 15 ml of water. Add this solution to the reaction medium and stir for one night at room temperature.

Acidify with HCl 6N and extract with 3 times 50 ml of ethyl acetate.

Purify by flash chromatography on 600 g of silica (eluant: Ch$_2$Cl$_2$:MeOH:AcOH, 97:3:0.3). Recover 6.05 g of product b) or 77%. RMN identical to b) of method A.

Intermediary 2: (Z) but-2-enyl triethylsilane

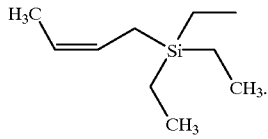

In a mini-autoclave cooled to −20° C., introduce:
9.8 ml (113 mmoles) of butadiene
18 ml (113 mmoles) of triethylsilane
60 mg (0.22 mmoles) of nickel acetylacetonate
0.32 ml (2.3 mmoles) of triethylaluminum.

Stir for 24 hours at 60° C. Distill at 50–53° C. under 7 mmHg. Recover 12.7 g (67%) of product Z. RMN (CDCl$_3$): δ5.4 (2H, m,—C$\underline{H}$=C$\underline{H}$); 1.6 (3H, m, C$\underline{H}_3$—CH=); 1.55 (2H, m, HC=CH—C$\underline{H}_2$); 1 (9H, m, 3C$\underline{H}_3$); 0.5 (6H, m, 3C$\underline{H}_2$Si).

Intermediary 3: 1(Z) hex-2-enyl triethylsilane

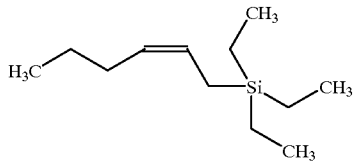

a) 1(hex-3-ynyl) triethylsilane

Under nitrogen atmosphere, introduce 8.8. ml (13 mmoles) of tBuli 1.45 M in pentane. Add Et$_2$O (12 ml), 1.84 ml (12 mmoles) of TMEDA, 1.37 ml (12 mmoles) of 2-hexane and allow to return to 0° C.

Stir for 1 hour at 0° C., then cool again to −78° C. and introduce 2.45 ml (15 mmoles) of chlorotriethylsilane. Allow to return to +20° C. in approximately 45 minutes.

Add 20 ml of water. Extract with diethyl ether. Dry. Evaporate. Distill at 75% under 0.4 mmHg in the ball kiln. Recover 2.76 g (or 100%) of product.

RMN (CDCl$_3$): δ2.15 (2H, m,—C$\underline{H}_2$—C≡); 1.5 (4H, m, C$\underline{H}_2$—CH$_2$—C≡CH—C$\underline{H}_2$—Si); 1 (12H, m, Si(CH$_2$—C$\underline{H}_3$)$_3$ and C$\underline{H}_3$—CH$_2$—CH$_2$); 0.65 (6H, m, Si(C$\underline{H}_2$—CH$_3$)$_3$).

b) 1-(Z)hex-2-enyl triethylsilane

To 9.5 ml of absolute ethanol containing 0.5 ml of soda 2N, add 400 mg of NaBH$_4$. Stir for 10 minutes. Filter in 15 ml of absolute ethanol containing 370 mg (1.5 mmoles) of Nickel acetate, add 1.5 ml (1.5 mmoles) of the filtered solution. Place under hydrogen atmosphere. Add 2.35 g (12 mmoles) of product a) and stir for 2 hours at room temperature. Filter on celite. Concentrate. Distill at 125° C./22 mmHg. Recover 1.64 g or 68%.

RMN (CDCl$_3$): δ5.4 and 5.25 (2 m, 2H, C$\underline{H}$=C$\underline{H}$); 2 (2H, m, C$\underline{H}_2$—CH=); 1.55 (2H, d, =CH—C$\underline{H}_2$—Si); 1.4 (m, 2H, CH$_3$—C$\underline{H}_2$—CH$_2$—CH=); 1 (12H, m, C$\underline{H}_3$—CH$_2$—CH$_2$ and Si(CH$_2$—C$\underline{H}_3$)$_3$); 0.55 (6H, m, Si(C$\underline{H}_2$—CH$_3$)$_3$).

Intermediary 4: 2(S)[1(S) (1,1 dimethyl) ethoxycarbonyl) ethyl]2(S) hydroxy-4-methyl pentanoic acid

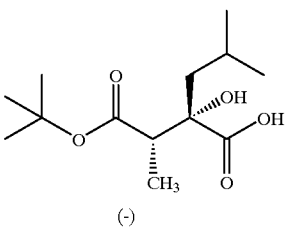

(-)

a) 4-Methyl-2-sodium oxopentanoate

In a 20-l reactor, introduce 771.8 g (6 moles) of tBuOK and 6 l of ethyl ether. Purge with nitrogen. Cool to +8° C. Add in 1 hour 846 ml (6 moles) of ethyl oxalate. Return to +20° C. and add in 20 minutes 900 ml (6 moles) of ethyl isovalerate and stir at room temperature for one night. Freeze at 0° C. and add 6 l of HCl N. Extract with ethyl ether. Dry (Na$_2$SO$_4$) and evaporate the organic phases.

Take up the oil obtained with 3 l of dioxane and 3 l of H$_2$SO$_4$ 5N and heat for 4 days at 100° C. Freeze and neutralize with 2.2 l of NaOH 10N (pH 7). Wash 2 times with AcOEt. Evaporate the aqueous phase to dryness. Dry the solid obtained in the vane pump. Take up with 7 l of methanol. Mix, filter, concentrate. Recrystallize the 1,020 g obtained in 6.4 l of absolute ethanol. Recover 454 g (50%) of pure product.

RMN (CD$_3$OD): δ2.6 (2H, d, CH—C$\underline{H}_2$COCOONa); 2.15 (1H, m, (CH$_3$)$_2$—C$\underline{H}$—CH$_2$); 0.95 (6H, d, (C$\underline{H}_3$)$_2$ CH).

b) (S) ethyl mandelate

In 20 ml of dry CH$_2$Cl$_2$, add 1.52 g (10 mmoles) of mandelic acid S, εDMAP, 1.70 ml (21 mmoles) of pyridine and εDMF. Add 2.7 ml (21 mmoles) of TMSCl and stir for 2 hours at room temperature. Add 0.91 ml (10.5 mmoles) of oxalyl chloride and stir for 2 hours at room temperature. Add 20 ml of ethanol and stir for ½ hour at room temperature. Wash with 2×20 ml of HCl N then NaHCO$_3$. Dry (Na$_2$SO$_4$), evaporate to dryness. Recover 1.73 g (96%).

[α]$_D$=127.7° at t=21° C. (c=3, CHCl$_3$).

RMN (CDCl$_3$): δ7.4 (5H, m, CH(A$\underline{r}$)); 5,2 (1H, s, Ar—C$\underline{H}$—OH); 4.2 (2H, m, OC$\underline{H}_2$); 1.25 (3H, t, OCH$_2$C$\underline{H}_3$).

c) 4-methyl-2-oxo pentanoic 1 (S) ethoxycarbonyl phenyl methyl ester acid

Disperse 50 g (0,329 mole) of methyl-4-oxo-2 sodium pentanoate in 900 ml of CH$_2$Cl$_2$ containing εDMF. Add dropwise 28.7 ml (0.329 mole) of oxalyl chloride. At the end of addition, stir for 30 minutes at room temperature. Cool to +10° C. and add 56.4 g (0.313 M) of compound b) solubilized in 300 ml of CH$_2$Cl$_2$. Then add 57.3 ml (0.411 mole) of triethylamine diluted in 200 ml of CH$_2$Cl$_2$. Stir for one night at room temperature. Wash with HCl N, then NaHCO$_3$. Dry, evaporate. Purify by flash chromatography on 800 g of silica (eluant: heptane:AcOEt; 95:5). Recover 71 g of oil (78%).

RMN (CDCl$_3$): δ7.5 (5H, m, H(Ar); 6 (1H, s,—O—CH—CO$_2$Et); 4.2 (2H, m, OCH$_2$—Ch$_3$); 2.8 (2H, d, —CH$_2$—COCO); 2.3 (1H, m, CH—(CH$_3$)$_2$); 1.25 (3H, t, OCH$_2$—CH$_3$); 1 (6H, d, (CH$_3$)$_2$CH).

d) -2(S) hydroxy-2(S)[(2-methyl)propyl] 3(R) methyl pent-4-enoic 1 (S) ethoxy carbonyl phenylmethyl ester acid Solubilize 10 g (34.2 mmoles) of compound c) in 200 ml of dry CH$_2$Cl$_2$. Cool to −78° C. and add 3.94 ml (34.2 mmoles) of SnCl$_4$. Stir for 30 minutes at −78° C. and add 5.83 g (34.2 mmoles) of intermediary 2 diluted in 50 ml of CH$_2$Cl$_2$. Stir for 1 hour 30 minutes at −78° C. and add HCl N. Extract with CH$_2$Cl$_2$, dry (Na$_2$SO$_4$), evaporate. Eliminate the triethylsilanol in the rotary evaporator (70° C. under 1 mmHg). Recover 11.6 g of oil (97%).

RMN (CDCl$_3$): δ7.45 (5H, m, H(Ar)); 5.95 1H, s, OCHAr); 5.85 (1H, m, CH$_2$=CH); 5.1 (2H, m, CH$_2$=); 4.25 (2H, m, OCH$_2$—CH$_3$); 3.1 (1H, broad s, OH); 2.6 (1H, m, =CH—CH(CH$_3$)—); 1.65 (3H, m, CH$_2$—CH—(CH$_3$)$_2$); 1.3 (3H, t, OCH$_2$—CH$_3$); 1.25 (3H, d, =CH—CH(CH$_3$)—); 0.95 (3H, d) and 0.7 (3H, d, —CH(CH$_3$)$_2$)

e) 2 (S)[-1(-1(S) hydroxycarbonylethyl]-2 (S) hydroxy 4-methyl pentanoic (S) (ethoxycarbonyl) (phenyl)methyl ester acid 54.7 g (157 mmoles) of product d) are dispersed in 550 ml of dry CH$_2$Cl$_2$. Cool to −60° C. and ozonolyze to steady blue color. Purge with nitrogen and add 20.4 g (314 mmoles) of Zn and 18.3 ml (314 mmoles) of acetic acid. Stir for 1 hour at room temperature. Filter and evaporate. Take up the residue obtained in 550 ml of tBuOH. Add 50 ml (471 mmoles) of 2-methyl-2-butene. Then add an aqueous solution containing 48.9 g (314 mmoles) of NaH$_2$PO$_4$, 2H$_2$O, 35.9 g (361 mmoles) of NaClO$_2$, H$_2$O 215 ml.

Stir for one night at room temperature. Add a saturated NaHCO$_3$ solution. Wash with pentane and extract with ethyl ether. Dry. Evaporate. Recover 46.1 g of white oil (or 80%).

[α]$_D$: +60.2° at t=20° C. (c=1, CHCl$_3$).

RMN (CDCl$_3$): δ7.45 (5H, s, HAr); 6 (1H, s, O—CH(CO)—Ar); 4.25 (2H, m OCH$_2$CH$_3$); 3.1 (1H, q, HO$_2$C—CH(CH$_3$)); 1.8 (3H, m, CH$_2$—CH(CH$_3$)$_2$); 1.4 (3H, d, CH(CH$_3$)—COOH); 1.3 (3H, t, OCH$_2$—CH$_3$); 0.95 and 0.75 (6H, 2d, CH—CH$_3$)$_2$)

f) 2-(S) [1(S) (1,1 dimethyl ethoxycarbonyl)ethyl]-2 (S) hydroxy-4-methyl pentanoic (S) ethoxy carbonyl phenylmethyl ester acid 34.5 g (94.1 mmoles) of compound e) are solubilized in 330 ml of dry CH$_2$Cl$_2$. Cool the autoclave to −20° C., add 300 ml of isobutene, 0.4 ml of concentrated sulfuric acid. Close the autoclave and stir for one night at room temperature. Pour over a saturated NaHCO$_3$ solution. Dry the organic phase, filter, evaporate to dryness. Recover 31.9 g of pure product (80%).

[α]$_D$=+70.2° at t=20° C. (c=1, MeOH)

RMN (CDCl$_3$): δ7.45 (5H, m, HAr); 6 (1H, s, O—CH Ar); 4.2 (2H, m, OCH$_2$CH$_3$); 3.75 (1H, broad s, OH); 2.9 (1H, q, tBuOCOCH); 1.7 (3H, m, CH$_2$CH(CH$_3$)$_2$); 1.5 (9H, s, (CH$_3$)$_3$—C); 1.4 (3H, d, CH—CH$_3$); 1.25 (3H, t, OCH$_2$CH$_3$); 0.95 and 0.7 (6H, 2d, CH—CH$_3$)$_2$).

g) 2-(S) [1 (S)((1,1 dimethyl) ethoxycarbonyl) ethyl] 2 (S) hydroxy 4-methyl pentanoic acid Solubilize 31.7 g (75 mmoles) of product f) in 320 ml of absolute ethanol. Under nitrogen, add 3.2 g of 10% Pd/C. Stir for 2 hours at 20° C. under hydrogen atmosphere. Filter the catalyst, rinse it in ethanol. Evaporate to dryness. Take up with ethyl ether, extract with 75 ml of soda N.

Wash the aqueous phase, then acidify with 75 ml of HCl N. Extract with ethyl ether, dry, evaporate. Recover 18.7 g of white solid (95%).

M.P.: 67° C.

[α]$_D$=−9.9° C. at t=20° C. (c=1, CHCl$_3$)

RMN (CDCl$_3$): δ8.9 and 4.6 (2H very broad, OH and COOH); 2.75 (1H, q, tBuOCOCHCH$_3$); 1.85 (2H, m, CH$_2$—CH); 1.55 (1H, m, CH$_2$—CH); 1.5 (9H, s, (CH$_3$)$_3$C); 1.2 (3H, d, COCHCH$_{30}$; 1 and 0.9 (6H, 2d, CH(CH$_3$)$_2$).

Intermediate 5: 2-(S), 3(S)dihydroxy-3(S)-hydroxycarbonyl-5 methyl hexanoic, 1,1-dimethyl ester acid

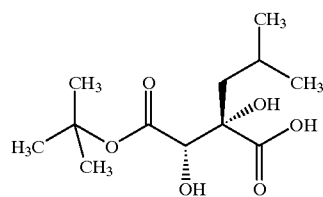

a) 4-methyl-2-oxo pentanoic phenylmethyl ester acid

Disperse 78.7 g (0.51 mole) of compound a) of intermediary 4 in 500 ml of dry CH$_2$Cl$_2$. Add 39.2 ml (0.51 mole) of DMF. Cool to −20° C. and add 45 ml (0.51 mole) of oxalyl chloride. Stir for 2 hours at room temperature.

At 0° C., add the mixture of 50 ml of CH$_2$Cl$_2$, 44 ml (0.425 mole) of benzyl alcohol, 143.4 ml of triethylamine. Stir for 18 hours at room temperature. Wash with HCl N, then NaHCO$_3$ (saturated solution). Dry over Na$_2$SO$_4$. Filter, evaporate to dryness. Distill at 114° C. under 3 mmHg. Recover 70.85 g (63%).

RMN (CDCl$_3$); δ7.45 (5H, m, H (Ar)); 5.3 (2H, s, OCH$_2$Ar); 2.7 (2H, d, CH$_2$CO); 2.15 (1H, m, CH—(CH$_3$)$_2$); 0.95 (6H, d, CH(CH$_3$)$_2$).

b) 5-methyl-3(phenylmethoxycarbonyl)(E) hex-2-enoic, dimethyl 1-1 ethyl ester acid In a flask, introduce 46 g (0.10 mole) of tert-butoxycarbonyl methyl triphenyl phosphonium bromide. Add 12.8 g (0.1 05 mole) of tBuOK and stir for 30 minutes at room temperature. Add 20 g (0.091 mole) of compound a) diluted with 60 ml of DMF. Stir for one night at 20° C.

Evaporate to dryness.

Mix in isopropyl ether, filter, evaporate.

Purify by flash chromatography on 600 g of silica (eluant heptane:AcOEt; 95:5).

Recover 19.9 g (69%) of product E.

RMN (CDCl$_3$): δ7.4 (5H, s, HAr); 6.75 (1H, s, COCH=); 5.2 (2H, s, OCH$_2$Ar); 2.75 (2H, d, CH$_2$—C=); 1.9 (1H, m, CH—(CH$_3$)$_2$); 1.55 (9H, s, C(CH$_3$)); 0.95 (6H, d, CH(CH$_3$)$_2$).

c) 2(S), 3(S) dihydroxy-5 methyl-3(S) phenylmethoxycarbonyl hexanoic, dimethyl 1,1 ethyl ester acid Introduce into a flask 11.5 g of βAD-mix, 0.78 g (8.1 mmoles) of methyl sulfonamide, 83 ml of a 1/1 mixture of tBuOH and $H_2O$. Stir for 2 minutes at +20° C., then cool to 0° C.

Add 2.6 g (8.1 mmoles) of compound b). Stir for 4 hours at 0° C., then 2 hours at room temperature.

Add another 3 g of βAd-mix and stir for 1 night at 20° C. At 0° C., add 16.4 g of sodium sulfite, stir for 1 hour at room temperature.

Extract with $CH_2Cl_2$ Wash with water, then with KOH 2N. Dry, filter, evaporate to dryness. Recover 3.2 g of oil (100%).

RMN ($CDCl_3$); δ7.4 (5H, s, $\underline{H}$Ar); 5.25 (2H, s, $OC\underline{H}_2Ar$); 4.2 (1H, d, $O\underline{H}$); 3.55 (1H, s, $O\underline{H}$); 3.4 (1H, d, —$C\underline{H}$—OH); 1.75 (3H, m, $C\underline{H}_2$—$C\underline{H}(CH_3)_2$); 1.55 (9H, s, $OC(C\underline{H}_3)_3$); 1 and 0.85 (6H, 2d, CH—$(C\underline{H}_3)_2$).

d) 2(S)[(S) 4'dimethylethoxycarbonyl-S-hydroxymethyl] 2S hydroxy 4 methyl pentanoic acid Solubilize 2 g of compound c) (5.66 mmoles) in 20 ml of methanol under nitrogen. Add 200 mg of 10% Pd/c. Purge with hydrogen and stir for 3 hours at 20° C. Filter the catalyst on celite, evapaorate to dryness.

Recover 1.1 g (95%) of yellow solid.

MP: 110° C.

RMN ($CDCl_3$): δ5.9 (1H, very broad s, OH); 4.25 (1H, s, $C\underline{H}OH$); 1.9 (2H, d, $C\underline{H}_2$—CH); 1.8 (1H, m, $C\underline{H}$—$(CH_3)_2$); 1.55 (9H, s, $(C\underline{H}_3)_3C$); 1 and 0.9 (6H, 2d, $(C\underline{H}_3)_2$ CH).

Intermediary 6: 3 (S) hydroxy-3 (S) hydroxycarbonyl-2(S) methoxy 5-methylhexanoic, 1,1-dimethylethyl ester acid

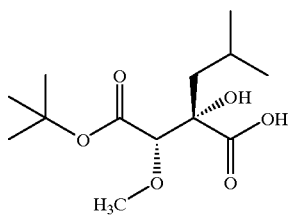

a) 3(S)-hydroxy-2(S) methoxy-5 methyl 3(S) phenylmethoxycarbonyl hexanoic, dimethyl 1.1 ethyl ester acid To a suspension of 85 mg (3.4 mmoles) of NaH in 10 ml of dry THF, add at 0° C. 1 g (2.8 mmoles) of compound c) of intermediary 5. Stir for 30 minutes at 20° C.

At 0° C., add 0.9 ml (14 mmoles) of $CH_3I$. Stir for one night at room temperature.

Add HCl N. Extract with $CH_2Cl_2$ Dry, evaporate. Purify by flash chromatography (eluant heptane:AcOEt; 95:5).

Recover 380 mg (38%) of pure product.

RMN ($CDCl_3$): δ7.4 (5H, m, $\underline{H}$Ar); 5.25 (2H, dd, $OC\underline{H}_2Ar$); 3.85 (1H, s, $C\underline{H}OCH_3$); 3.4 (1H, s, $O\underline{H}$); 3.25 (3H, s, $OC\underline{H}_3$); 1.8 (2H, d, $C\underline{H}_2CH$); 1.7 (1H, m, $CH_2$—$C\underline{H}$—$(CH_3)_2$); 1.55 (9H, s, $C(CH_3)_3$); 1 and 0.85 (6H, 2d, $CH(C\underline{H}_3)_2$).

b) 3(S) hydroxy hydroxycarbonyl-2(S) methoxy-5 methyl hexanoic, dimethyl 1.1 ethyl ester acid To a suspension of 40 mg of 10% Pd/c in 5 ml of methanol, add 380 ml (1 mmole) of the preceding compound. Stir for 2 hours at 20° C. under hydrogen atmosphere. Filter on celite. Rinse with methanol. Evaporate to dryness. Recover 270 mg (93%).

RMN ($CDCl_3$): δ3.9 (1H, s, $C\underline{H}(OCH_3)$); 3.45 (3H, s, $OC\underline{H}_3$); 1.75 (2H, m, $C\underline{H}_2C\underline{H}(CH_3)_2$); 1.6 (10 H, m, C(C$\underline{H}_3)_3$+$C\underline{H}_2CH$); 1 (6H, dd, $(CH(C\underline{H}_3)_2)$.

Intermediary 7: 2(S)[-2(S)-but-3-enyl]-2(S) hydroxy 4-methyl pentanoic acid

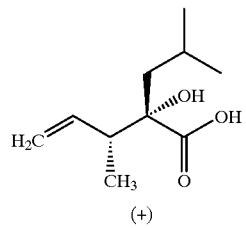

(+)

To 930 mg (2.67 mmoles) of compound d) of intermediary 4 in 8 ml of ethanol, add 8 ml of soda N (8 mmoles) and heat for one night under reflux.

Cool at 20° C., wash with ethyl ether. Acidify with HCl N and extract with dichloromethane. Dry over $Na_2SO_4$, filter, evaporate.

Purify the 810 mg of oil obtained by flash chromatography on 37 g of silica (eluant: $CH_2Cl_2$:MeOH:AcOH; 95:5:0.5).

Recover 410 mg of pure product (82%).

$[\alpha]_{365}$=+24.1° at t=20° C. (c=1.25, MeOH).

RMN (DMSO): δ5.7 (1H, m, $CH_2$=$C\underline{H}$—); 5.05 (1H, d, $C\underline{H}_2$=); 5 (1H, s, $C\underline{H}_2$=); 2.35 (1H, m, $CH_2$=CH—C$\underline{H}$—$CH_3$); 1.65 (1H, m, $C\underline{H}$—$(CH_3)_2$); 1.5 (2H, d, C$\underline{H}_2$—$CH(CH_3)_2$); 0.85 and 0.8 (9H, 3d, $C\underline{H}_3$).

Intermediary 8: 2-oxo-5-phenylpentanoic (S) ethoxycarbonyl (S) phenylmethyl ester acid

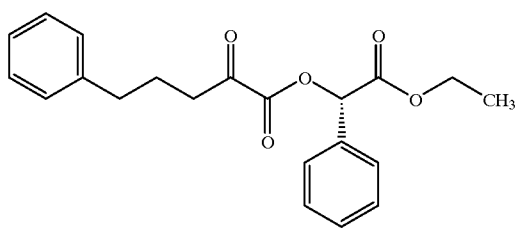

Synthesized in the same manner as for intermediary 4.

a) 2-oxo-5 phenyl pentanoic, sodium salt acid

RMN (DMSO): 7.2 (5H, m, $\underline{H}$(Ar)); 2.5 (4H, m, $COCH_2CH_2C\underline{H}_2$); 1.55 (2H, m, $COCH_2C\underline{H}_2$).

IR: ν ketone: 1706 $cm^{-1}$ ν COONa: 1625 $cm^{-1}$ b) 2-oxo-5 phenyl pentanoic (S) ethoxycarbonyl (S) phenyl methyl ester acid RMN ($CDCl_3$): δ7.4 (10H, m, $\underline{H}$(Ar); 6 (1H, s, $OC\underline{H}Ar$); 4.25 (2H, m, $OC\underline{H}_2$); 2.95 (2H, m, $ArC\underline{H}_2$); 2.8 (2H, t, $COCH_2$); 2.05 (2H, m, $COCH_2C\underline{H}_2$); 1.25 (3H, t, $CH_2C\underline{H}_3$).

Intermediary 9: 2(S) hydroxy-3(R)methyl 2(S)-(2-propyl) pent-4-enoic acid

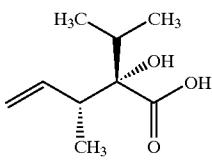

a) 2-oxo-3-methyl butyric (S) ethoxycarbonyl (S) phenylmethyl ester acid

Synethesized in the same manner as intermediary 4c.

RMN (CDCl$_3$): δ7.4 and 7.5 (5H, 2m, H(Ar)); 6.05 (1H, s, OCHAr); 4.2 (2H, m, OCH$_2$CH$_3$); 3.3 (1H, m, CH(CH$_3$)$_2$); 1.25 (9H, m, OCH$_2$CH$_3$ and CH(CH$_3$)$_2$).

b) 2(S)hydroxy-3(R) methyl-2(S)-(2-propyl) pent-4-enoic(S) ethoxycarbonyl(S) phenyl methyl ester acid This product was synthesized in the same manner as compound 4d.

RMN (CDCl$_3$): δ7.45 (5H, m, H(Ar)); 6 (1H, s, OCHAr); 5.85 (1H, m, CH$_2$=CH—); 5.75 (2H, m, CH$_2$=CH; 4.25 (2H, m, OCH$_2$CH$_3$); 3.1 (1H, broad s, OH); 2.6 (1H, m, CH$_2$=CH—CH—CH$_3$); 2.15 (1H, m, CH(CH$_3$)$_2$); 1.3 (6H, 2d, CH$_2$=CH—CH$_3$ and OCH$_2$CH$_3$); 0.9 (6H, 2d, CH(CH$_3$)$_2$).

c) Intermediary 9: 2(S) hydroxy-3(R) methyl 2(S)-(2-propyl) pent-4-enoic acid This product was prepared in the same manner as intermediary 7.

RMN (CDCl$_3$); δ5.85 (1H, m, CH$_2$=CH—); 5.2 (2H, m, CH$_2$=CH—); 3 (1H, very broad s, OH); 2.75 (1H, m, CH$_2$=CH—CH—CH$_3$); 2.15 (1H, sept., CH(CH$_3$)$_2$); 1.15 (3H, d, =CHCH$_3$); 1.05 (6H, 2d, CH(CH$_3$)$_2$).

Intermediary 10: 4-chlorophenylalanine N-(2-methylthio-1-ethyl) amide

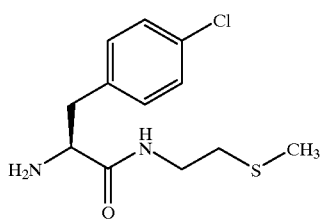

Solubilize in 5 ml of dry CH$_2$Cl$_2$ 500 mg (1.7 mmoles) of Boc 4-chlorophenylalanine. Add 160 μl (1.7 mmoles) of 2-methylthioethylamine, 415 mg (2 mmoles) of DCC and 270 mg (2 mmoles) of HOBT. Stir for one night at room temperature. Filter the DCU. Wash with HCl 1N, then NaHCO$_3$. Dry. Evaporate.

Take up with 6 ml of dry CH$_2$Cl$_2$. Add 1.5 ml of CF$_3$COOH and stir for 3 hours at room temperature. Evaporate to dryness. Take up with AcOEt. Extract the product with HCl N. Neutralize the aqueous phase with NaHCO$_3$ and extract with CH$_2$Cl$_2$. Dry. Evaporate. Recover 300 mg (or 74%) of pure product.

MP: 70° C.

RMN (CDCl$_3$): δ7.6 (1H, broad s, CONH); 7.3 and 7.5 (4H, 2d, H(Ar); 3.6 (1H, m, NH$_2$CH); 3.55 (2H, q, CONHCH$_2$); 3.25 (1H, 2d, CH$_2$Ar); 2.75 (1H, m, CH$_2$Ar); 2.65 (2H, t, CH$_2$SCH$_3$); 2.15 (3H, s, SCH$_3$); 1.3 (2H, s, NH$_2$).

The intermediaries 11 to 17 were synthesized in the same manner.

Intermediary 11: 4-chlorophenylalanine N-(2-(4-morpholino)-1-ethyl) amide

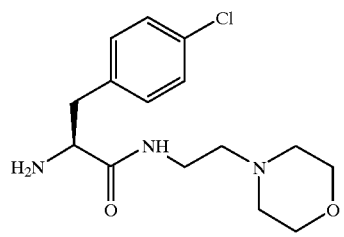

RMN (CDCl$_3$): δ7.35 (1H, broad s, CONH); 7.3 and 7.2 (4H, 2d, H(Ar)); 3.7 (4H, m, —(CH$_2$)$_2$O); 3.6 (1H, m, H$_2$N—CH—CO); 3.35 (2H, q, CONHCH$_2$—); 3.15 (1H, dd, CH$_2$Ar); 2.75 (1H, dd, CH$_2$Ar); 2.4 (6H, m, —CH$_2$—N—(CH$_2$)$_2$—); 1.7 (2H, broad s, NH$_2$).

Intermediary 12: 4-iodophenylalanine N-(2-methylthio-1-ethyl) amide

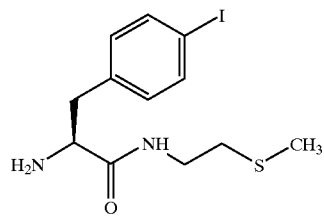

RMN (CDCl$_3$): δ7.65 (2H, d, H(Ar)); 7.5 (1H, broad s, CONH); 6.95 (2H, d, H(Ar)); 3.6 (1H, m, H$_2$NCHCO); 3.45 (2H, m, CONHCH$_2$); 3.15 (1H, 2d, CH$_2$Ar); 2.7 (1H, 2d, CH$_2$Ar); 2.6 (2H, m, —CH$_2$SCH$_3$); 2.1 (3H, s, SCH$_3$); 1.7 (2H, broad s, H$_2$N).

Intermediary 13: 3-4-dichlorophenylalanine N-(2-methylthio-1-ethyl) amide

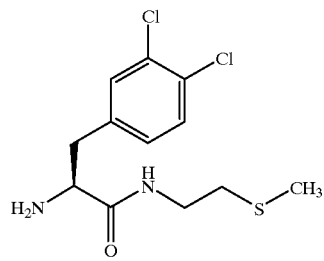

RMN (CDCl$_3$): δ7.55 (1H, broad s, CONH); 7.3 (2H, m, H(Ar)); 7.05 (1H, m, H(Ar)); 3.6 (1H, m, H$_2$NCHCO); 3.5 (2H, m, CONHCH$_2$); 3.2 (1H, dd, CH$_2$Ar); 2.75 (1H, dd, CH$_2$Ar); 2.6 (2H, m, CH$_2$S); 2.15 (3H, s, SCH$_3$); 1.3 (2H, very broad s, H$_2$N).

Intermediary 14: 4-chlorophenylalanine N-(2-cyano-1-ethyl) amide

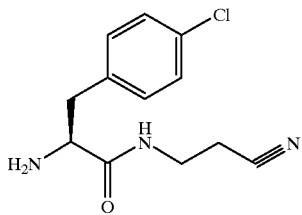

RMN (CDCl$_3$): δ7.8 (1H, broad s, CON$\underline{H}$); 7.3 (2H, d, H(Ar)); 7.15 (2H, d, $\underline{H}$(Ar)); 3.65 (1H, m, H$_2$NC$\underline{H}$CO); 3.55 (2H, m, CONHC$\underline{H}_2$—); 3.25 (1H, dd, C$\underline{H}_2$Ar); 2.75 (1H, dd, C$\underline{H}_2$Ar); 2.65 (2H, t, C$\underline{H}_2$CN); 1.45 (2H, very broad s, N$\underline{H}_2$).

Intermediary 15: 3,4-dichlorophenylalanine N-[2-(2 hydroxyethyl)oxy ethyl] amide

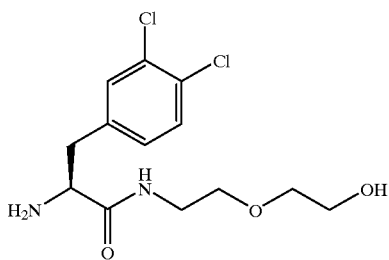

RMN (CDCl$_3$): δ7.5 (1H, broad s, CON$\underline{H}$); 7.3 (2H, m, H(Ar)); 7.1 (1H, m, H(Ar)); 3.75 (2H, m, C$\underline{H}_2$OH; from 3.65 to 3.45 (9H, m, H$_2$N—CH—CONHC$\underline{H}_2$—CH$_2$O—C$\underline{H}_2$); 3.2 (1H, 2d, C$\underline{H}_2$Ar); 2.7 (1H, 2d, C$\underline{H}_2$Ar).

Intermediary 16: 3,4-dichlorophenylalanine N-[2-(2-methoxyethoxy) 1-ethyl]amide

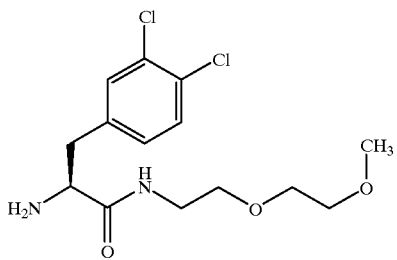

RMN (CDCl$_3$): δ7.5 (1H, broad s, CON$\underline{H}$); 7.35 (2H, m, H(Ar)); 7.1 (1H, m, H(Ar)); from 3.45 to 3.7 (9H, m, H$_2$NC$\underline{H}$CONH—CH$_2$—CH$_2$—O—CH$_2$CH$_2$—OCH$_3$); 3.4 (3H, s, OC$\underline{H}_3$); 3.15 (1H, dd, C$\underline{H}_2$Ar); 2.9 (1H, dd, C$\underline{H}_2$Ar); 2 (2H, very broad s, N$\underline{H}_2$).

Intermediary 17: L β cyclohexylalanine N-(2-phenyl-1-ethyl)amide

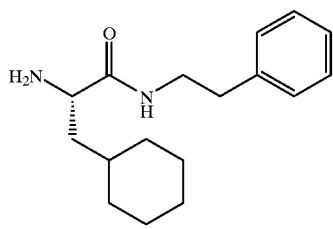

RMN (CDCl$_3$); δ from 7.2 to 7.4 (6H, m, CON$\underline{H}$CH$_2$ and H(Ar)); 3.55 (2H, m, H$_2$NC$\underline{H}$CONHC$\underline{H}_2$); 3.4 (1H, dd, CONHC$\underline{H}_2$—); 2.85 (2H, m, C$\underline{H}_2$Ar); from 0.9 to 1.9 (16H, 3 m, $\underline{H}_2$NCH—C$\underline{H}_2$-cyclohex.

Intermediary 18: D,L 2,4-dichlorophenylalanine N-methylamide

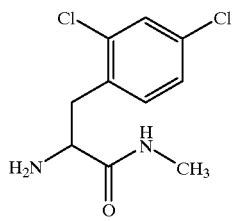

The racemic amino acids were synthesized by the methods known in the state of the art.

Solubilize 1 g (4.27 mmoles) of D,L 2,4-dichlorophenylalanine in 35 ml of MeOH. Add 3.25 ml (25.6 mmoles) of TMSCl and heat for one night under reflux.

Evapaorate to dryness. Take up with 20 ml of MeOH. Freeze at −20° C. Add 15 ml of methylamine and stir for 3 hours at +20° C. Evaporate to dryness. Take up with water. Neutralize with NaHCO$_3$ and extract with chloroform. Dry. Evaporate. Recover 900 mg (or 85%) of oil.

RMN (CDCl$_3$): δ7.4 (1H, s, H(Ar)); 7.2 (2H, s, H(Ar)); 7.15 (1H, m, CON$\underline{H}$); 3.7 (1H, m, NH$_2$C$\underline{H}$CO); 3.45 (1H, dd, C$\underline{H}_2$Ar); 2.9 (1H, dd, C$\underline{H}_2$Ar); 2.85 (3H, d, NHC$\underline{H}_3$); 1.55 (2H, broad s, NH$_2$).

The intermediaries 19 to 21 were synthesized in the same manner:

Intermediary 19: D,L 2,6-dichlorophenylalanine N-methylamide

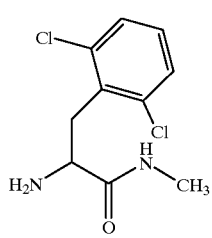

RMN (CDCl$_3$): δ7.3 (2H, d, H(Ar)); 7.15 (1H, t, $\underline{H}$(Ar)); 3.75 (1H, m, NH$_2$C$\underline{H}$CO); 3.65 (1H, dd, C$\underline{H}_2$Ar); 3.15 (1H, dd, C$\underline{H}_2$Ar); 2.85 (3H, d, NHC$\underline{H}_3$).

Intermediary 20: D,L 3-chlorophenylalanine N-methylamide

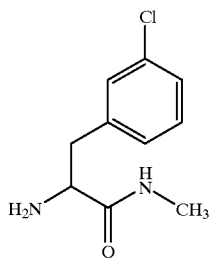

RMN (DMSO): δ8.1 (1H, q, CONHCH₃); 7.25 (3H, m, H(Ar)); 7.15 (1H, d, H(Ar)); 3.55 (1H, m, CHCONHCH₃); 2.95 (1H, dd, CH₂Ar); 2.75 (1H, dd, CH₂Ar); 2.55 (3H, d, NHCH₃).

Intermediary 21: D,L 2,5 dichlorophenylalanine N-methylamide

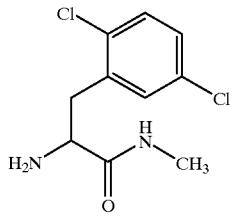

RMN (CDCl₃); δ from 7.15 to 7.35 (4H, m, H(Ar), CONH); 3.7 (1H, dd, H₂NCHCO); 3.5 (1H, dd, CH₂Ar); 2.9 (4H, m, CH₂Ar and NHCH₃); 1.4 (2H, very broad s, NH₂).

Intermediary 22: 2 (R)[1(S*)(4-(methoxy)-benzylmercapto)ethyl] 2(R*)-hydroxy 4-methylpentanoic acid

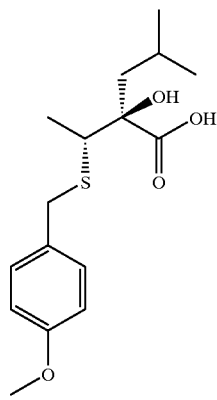

a) (E)-2[2(methyl)propyl]but-2-enoic ethyl ester acid

To 183.54 g (0.494 moles) of ethyltriphenylphosphonium bromide in 940 ml of THF, at room temperature, add 593 ml (0.593 mole) of bis-trimethylsilyl sodium amide (1 M in THF), then 147 ml of HMPA dropwise.

Stir at room temperature for 45 minutes, then add 62.57 g (0.395 mole) of 4-methyl-2-oxopentanoic ethyl ester acid in solution in 60 ml of THF in 1 hour at room temperature. Stir for 1 hour at room temperature and pour the reaction medium over 900 ml of water and ice.

Extract with 3 times 800 ml of ethyl ether and dry over sodium sulfate, then evaporate under vacuum at 30° C.

Purify by flash chromatography (eluant: heptane:Et₂O; 99:1 then pentane: Et₂O; 97:3.

Recover 43.71 g of a yellow oil (65%).

RMN (CDCl₃): δ6.9 (q, 1H, CH=); 4.2 (q, 2H, OCH₂CH₃); 2.2 (d, 2H, CH₂CH); 1.8 (d, 3H and m, 1H, CH₃CH= and CH₂CHCH₃); 1.3 (t, 3H, OCH₂CH₃); 0.9 (d, 6H, CH(CH₃)₂);

IR (CHCl₃); νCO: 1701 cm⁻¹; νC=C: 1644 cm⁻¹.

b) 2 (S)[1 (oxoethyl)] 2-hydroxy 4-methylpentanoic ethyl ester acid

To 13.82 g (81.2 mmoles) of product a) in 1.12 l of acetone, 335 ml of water and 28.35 ml of acetic acid at −10° C., add with spatulas 22.32 g (141.2 mmoles) of KMnO₄.

Stir for 1 hour 30 minutes, then filter.

Evaporate the acetone from the filtrate, then extract with CH₂Cl₂ and dry over Na₂SO₄.

Evaporate under vacuum and purify by flash chromatography (eluant: heptane:CH₂Cl₂:AcOEt; 88:10:2).

Recover 3.53 g of a colorless liquid (21%).

RMN (CDCl₃): δ4.3 (q, 2H, OCH₂CH₃); 4.2 (s, 1H, OH); 2.3 (s, 3H, CH₃CO); 2,1 (dd, 1H, CH₂CH); 1.8 (m, 2H, CH₂CH); 1.3 (t, 3H, OCH₂CH₃); 0.9 (dd, 6H, CH(CH₃)₂).

IR (CHCl₃): νOH: 3510 cm⁻¹; νCO (ketone and ester): 1717 cm⁻¹.

c) 2 (S)[1(S*)-hydroxyethyl] 2(S*)-hydroxy 4-methylpentanoic ethyl ester acid To 3.31 g (16.4 mmoles) of product b) in 33 ml of ethanol at 0° C., add 0.62 g (16.4 mmoles) of sodium borohydride in 15 minutes. Stir for 5 minutes, then evaporate the ethanol.

The residue is taken up in HCl 2N and extracted twice with Et₂O. The ethereal phases are dried over sodium sulfate, then evaporated. Purify by flash chromatography (eluant: heptane: Et₂O: CH₂Cl₂; 70:20:10).

Recover 0.81 g of the least polar diastereoisomer (25%).

RMN (CDCl₃): δ4.3 (q, 2H, OCH₂CH₃); 3.8 (m, 1H, CH—OH); 3.5 (s, 1H, OH); 2.3 (d, 1H, OH); 1.9 (dd, 1H, CH₂—CH); 1.8–1.7 (m, 2H, CH₂CH, CH(CH₃)₂); 1.4 (t, 3H, OCH₂CH₃); 1.15 (d, 3H, CH—CH₃); 1 (d, 3H, CH(CH₃)₂); 0.85 (d, 3H, CH(CH₃)₂).

IR (CHCl₃): νOH: 3528 cm⁻¹; νCO: 1721 cm⁻¹.

d) 2 (S)[1-(S*)-ethylmethanesulfonate] 2-(S*)-hydroxy 4-methylpentanoic ethyl ester acid To 0.48 g (2.35 mmoles) of product c) dissolved in 10 ml of ethyl ether at 0° C., add 0.36 ml (2.58 mmoles) of triethylamine, then 0.2 ml (2.58 mmoles) of methanesulfonic acid chloride. Stir for 1 night at room temperature.

The medium next is washed with H₂O, then soda 0.5 N, then water.

Dry over sodium sulfate and evaporate.

Recover 0.57 g of a viscous oil (86%).

RMN (CDCl₃): δ4.8 (q, 1H, CH—OSO₂CH₃); 4.3 (m, 2H, OCH₂CH₃); 3.6 (s, 1H, OH); 2.2 (dd, 1H, CH₂CH); 1.9 (m, CH(CH₃)₂); 1.7 (dd, 1H, CH₂CH); 1.5 (d, 3H, CH—CH₃); 1.4 (m, 3H, OCH₂CH₃); 1 (dd, 6H, CH(CH₃)₂).

IR (CHCl$_3$): νOH: 3518 cm$^{-1}$; νCO: 1728 cm$^{-1}$.

e) 2 (R)[1(S*)-(4-(methoxy)-benzylmercapto)ethyl]-2-(R*)-hydroxy 4-methylpentanoic ethyl ester acid To 0.33 g (2.12 mmoles) of 4-(methoxy)-benzylsulfide in 1.3 ml ethanol, add 0.97 ml (2.12 mmoles) of sodium ethylate (2.2 M in ethanol). Stir for 5 minutes and add this solution to 0,54 g (1.91 mmoles) of product d) in 8.8 ml of ethanol. Stir for 4 hours at 70° C. then 1 night at room temperature.

Evaporate the ethanol and take up the residue in AcOEt. Wash with H$_2$O, NaOH 1N, then water.

Dry over sodium sulfate and evaporate.

Purify by flash chromatography (eluant: heptane:Et$_2$O; 98:2 then 97:3).

Recover 0.23 g (35%).

RMN (CDCl$_3$): δ7.2 (d, 2H, CHAr); 6.8 (d, 2H, CHAr): 4.3 (q, 2H, OCH$_2$CH$_3$); 3.8 (s, 3H, OCH$_3$ and dd, 2H, CH$_2$S); 3.4 (s, 1H, OH); 2.8 (q, 1H, CHS); 2 (dd, 1H, CH$_2$CH); 1.7–1.5 (m, 2H, CHCH$_2$); 1.3 (t, 3H, OCH$_2$CH$_3$); 1.25 (d, 3H, CH$_3$CH); 1 (d, 3H, CH(CH$_3$)$_2$), 0.9 (d, 3H, CH(CH$_{32}$).

IR (CHCl$_3$): νOH: 3526 cm$^{-1}$; νCO: 1723 cm$^{-1}$.

f) 2 (R) [1(S*) (4-methoxy) benzylmercapto)ethyl] 2 (R*) -hydroxy 4-methylpentanoic acid To 0.31 g (0.91 mmole) of product d) in 6 ml of ethanol, add 3.18 ml (3.18 mmoles) of soda 1N. Stir for 1 night at 80° C. Dilute with H$_2$O and extract with AcOEt. Acidify the aqueous phase with HCl 1N and extract with CH$_2$Cl$_2$. Dry over sodium sulfate and evaporate. Crystallize by adding petroleum ether and a few drops of ethyl ether to the residue. Recover after filtration 0.123 g (43%).

RMN (CDCl$_3$): δ7.3 (d, 2H, CHAr); 6.8 (d, 2H, CHAr); 3.7 (s, 3H, OCH$_3$ and dd, 2H, CH$_2$S); 3,3 (s, 1H, OH); 2.9 (q, 1H, CHCH$_3$); 2 (dd, 1H, CH$_2$CH); 1.8 (m, 1H, CH$_2$CH); 1.7 (dd, 1H, CH$_2$CH); 1.3 (d, 3H, CH$_3$CH); 1 (d, 3H, CH(CH$_3$)$_2$), 0.9 (d, 3H, CH(CH$_3$)$_2$).

Intermediary 23: 2(S) [1(S*) (o-benzylhydroxylamino)ethyl]2(S)-hydroxy4-methylpentanoic acid

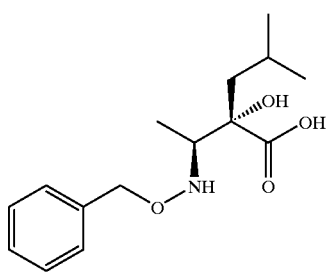

a) 2 (S)[(1-(R)-hydroxyethyl)] 2-(S)-hydroxy 4-methyl pentanoic ethyl ester acid To 21.84 g of βAD-mix in 70 ml of tert-butanol and 70 ml of water stirred for 20 minutes, add 1.16 g (12 mmoles) of methane sulfonamide.

Cool to 0° C., then add 2.08 g (12 mmoles) of product a) of intermediary 22.

Stir for 2 days at room temperature. Add 18 g of sodium sulfite and stir for 2 hours.

Extract with AcOEt and wash the organic phase twice with KOH 2N.

Dry over sodium sulfate and evaporate.

Purify by flash chromatography (eluant: CH$_2$Cl$_2$:AcOEt:MeOH; 95:4:1).

Recover 1.88 g (77%).

RMN (CDCl$_3$): δ4.3 (q, 2H, OCH$_2$CH$_3$); 3.9 (m, 1H, CHOH; 3.4 (s, 1H, OH); 2.05 (d, 1H, OH); 1.7–1.5 (m, 3H, CH$_2$CH); 1.3 (t, 3H, OCH$_2$CH$_3$); 1.25 (d, 3H, CH$_3$CH); 1 (d, 3H, CH(CH$_3$)$_2$); 0.9 (d, 3H, CH(CH$_3$)$_2$).

IR (CHCl$_3$): νOH: 3518 cm$^{-1}$; νCO: 1724 cm$^{-1}$.

b) 2 (S)[1(oxoethyl)]2(S)-hydroxy-4-methylpentanoic ethyl ester acid

To 6.76 g (33.1 mmoles) of product a) in 200 ml of CH$_2$Cl$_2$ at 0° C., add 9.4 ml (132 mmoles) of DMSO, then 18.7 g (132 mmoles) of P$_2$O$_5$.

Stir for 30 minutes at room temperature, then add another 9.38 g of P$_2$O$_5$.

Stir for 16 hours at room temperature, then add 32.3 ml (231.7 mmoles) of triethylamine in 15 minutes.

Stir for 1 hour at room temperature, then add 200 ml of HCl 1N at 0° C.

Decant, wash the organic phase twice with HCl 1N. Purify by flash chromatography (eluant: heptane:AcOET; 95:5).

Recover 3.25 g of oil (48%).

RMN (CDCl$_3$): δ4.3 (q, 2H, OCH$_2$CH$_3$); 4.2 (s, 1H, OH); 2.3 (s, 3H, CH$_3$CO); 2.1 (dd, 1H, CH$_2$CH); 1.9 (dd, 1H, CH$_2$CH); 1.8 (m, 1H, CH$_2$CH); 1.3 (t, 3H, OCH$_2$CH$_3$); 0.95 (dd, 6H, CH(CH$_3$)$_2$).

IR (CHCl$_3$): νOH: 3504 cm$^{-1}$; νCO (ester+ketone): 1716 cm$^{-1}$.

c) 2 (S) [1(o-benzylhydroxylimino)ethyl] 2-(S)-hydroxy 4-methylpentanoic ethyl ester acid To 0.674 g (3.33 mmoles) of product b) in 10 ml of ethanol, add 0.585 g (3.66 mmoles) of o-benzylhydroxylamine hydrochlorate and 0.27 ml (3.33 mmoles) of pyridine.

Stir at 95° C. for 3 hours.

Evaporate the ethanol and take up the residue with H$_2$O.

Extract with 3×50 ml of AcOEt.

Dry the organic phase and evaporate under vacuum.

Recover 1 g of a colorless oil (98%).

RMN (CDCl$_3$): δ7.3 (m, 5H, CHAr); 5.15 (s, 2H, CH$_2$Ar); 4.2 (q, 2H, OCH$_2$CH$_3$); 3.9 (s, 1H, OH); 1.9 (m, 5H, CH$_3$C=N and CH$_2$CH); 1.8 (m, 1H, CH$_2$CH); 1.3 (t, 3H, OCH$_2$CH$_3$); 0.95 (dd, 6H, CH(CH$_3$)$_2$).

IR (CHCl$_3$): νOH: 3514 cm$^{-1}$; νCO: 1726 cm$^{-1}$.

d) 2 (S) [1(o-benzylhydroxyamino) ethyl] 2 (S)-hydroxy 4-methylpentanoic ethyl ester acid To 0.737 g (2.4 mmoles) of product c) in 20 ml of methanol, add 1.35 g (21.6 mmoles) of sodium cyanohydroboride, then 5.13 ml of hydrochloric methanol dropwise.

Stir for 1 night and evaporate under vacuum.

The residue is taken up with HCl 1N and extracted three times with AcOEt.

Wash the organic phase wtih NaOH 1N, then H$_2$O.

Purify by flash chromatography (eluant: heptane:AcOEt; 9:1).

Recover 0.625 g of a colorless oil (84%).

RMN (DMSO): δ7.3 (m, 5H, HAr); 6.2 (d, 0.4H, NH); 6 (d, 0.6H, NH); 4.5 (dd, 2H, CH$_2$Ar); 4 m, 2H, OCH$_2$CH$_3$); 3.25 (m, 0.6H, CHNH); 3 (m, 0.4H, CHNH); 1.7–1.4 (m, 3H, CH$_2$CH); 1.2 (t, 3H, OCH$_2$CH$_3$); 1.05 (dd, 2H, CH$_3$CH); 0.9 (dd, 3H, CH(CH$_3$)$_2$); 0.8 (dd, 3H, CH(CH$_3$)$_2$).

IR (CHCl$_3$): νOH: 3514 cm$^{-1}$; νCO: 1723 cm$^{-1}$.

e) 2 (S) [1(o-benzylhydroxylamino) ethyl]2-(S) hydroxy 4-methylpentanoic acid To 0.6 g (1.95 mmoles) of product d) in 10 ml of ethanol, add 3.9 ml of soda 1N.

Stir at 100° C. for 6 hours. Evaporate the ethanol and take up the residue with H$_2$O. Neutralize to pH 6 with H$_2$SO$_4$ 1 M.

Evaporate to dryness and take up the residue with methanol. Filter, evaporate.

Recover 0.55 g of a white foam (100%).

RMN (DMSO): δ7.3 (m, 5H, HAr); 6.6 (d, 0.4H, NH); 6.4 (d, 0.6H, NH); 4.9 (s, 0.4H, OH); 4.8 (s, 0.6H, OH); 4.55 (m, 2H, CH$_2$Ar); 2.9 (m, 1H, CHNH); 1.8–1.4 (m, 3H, CH$_2$CH); 1 (dd, 3H, CH$_3$CH); 0.9–0.8 (m, 6H, CH(CH$_3$)$_2$).

IR (CHCl$_3$): νOH: 3416 cm$^{-1}$; νCO: 1724 cm$^{-1}$.

EXAMPLE 1

N-2(S)[1-hydroxycarbamoyl)-1-ethyl]2-(S) hydroxy-4 methylpentanoyl O-methyltyrosine N methylamide

A) N(1)[-2(S*) hydroxy-2(S*)(3 methyl) propyl 3 (R*) methyl pent-4-enoyl] O-methyltyrosine N-methylamide Solubilize 4.83 g (25.9 mmoles) of intermediary 1 in 100 ml of dry CH$_2$Cl$_2$. Add 5.40 g (25.9 mmoles) of o-methyltyrosine N-methylamide, 13.5 g (25.9 mmoles) of PyBop and 11.3 ml (64.8 mmoles) of diisopropylethylamine and stir for 3 hours at room temperature. Wash with HCl N then NaHCO$_3$. Dry, evaporate.

Purify by flash chromatography on 800 g of silica (eluant: heptane:AcOEt; 50:50).

Recover 8.31 g (or 85%) mixture of diastereoisomers.

RMN (CDCl$_3$): δ7.3 (1H, m, CONH—); 7.15 (2H, d, CH(Ar)); 6.85 (2H, d, CHAr); 6.1 (1H, d, —CONH); 5.75 (1H, m, CH=); 5.1 (2H, m, CH$_2$=); 4.6 (1H, m, CH-α(Tyr)); 3.8 (3H, s, OCH$_3$); 3.05 (2H, m, CH$_2$Ar); 2.75 (3H, 2d, CONHCH$_3$); 2.5 (1H, m, C=C—CH—CH$_3$); 1.6 (3H, m, CH$_2$—CH(CH$_3$)$_2$); 0.8 (9H, m, CH$_3$).

b) N-2(S*)[1(hydroxycarbonyl)-1 ethyl]-2(S*) hydroxy-4-methyl pentanoyl O-methyltyrosine N-methylamide Solubilize 8.05 g (21.4 mmoles) of product a) in 200 ml of tBuOH. Solubilize 45.7 g (214 mmoles) of NaIO$_4$ in 845 ml of water. Add 0.68 g (4.3 mmoles) of KMnO$_4$, 3.25 g (23.5 mmoles) of K$_2$CO$_3$. Stir for ½ hour, then add 200 ml of tBuOH, then add the solution of product a) and stir for 4 hours at room temperature.

Add HCl N and extract with 3 times 500 ml of AcOEt. Collect the organic phases and wash them with a thiosulfate acid solution. Dry over Na$_2$SO$_4$, evaporate to dryness.

Take up with NaOHN. Wash with ethyl ether. Acidify with HCl 6N and extract with AcOEt. Dry, evaporate. Recover 5,5 g (or 65%) (mixture of diastereoisomers).

RMN (DMSO): δ7.9 (1H, m, CONH); 7.6 (1H, m, CONH); 7.1 (2H, m, CH(Ar)); 6.8 (2H, m, CH(Ar)); 4.95 (1H, d, OH); 4.45 (1H, m, CH α(Tyr)); 3.7 (3H, s, OCH$_3$); 2.9 (2H, m, CH$_2$—Ar); 2.55 (4H, m, CONHCH$_3$ and CHCOOH); from 1.7 to 1 (3H, m, CH$_2$—CH—(CH$_3$)$_2$); from 1 to 0.5 (9H, 3CH$_3$).

c) N[2(S)[1(-phenylmethoxycarbamoyl)-1 ethyl]-2 (S) hydroxy-4methylpentanoyl]O-methyl-L-tyrosine N-methylamide Place 5.5 g (13.9 mmoles) of compound b) in 200 ml of dry THF. Add 3.16 g (15.3 mmoles) of DCC, 2.07 g (15.3 mmoles) of HOBT, 4.45 g (27.9 mmoles) of O benzylhydroxylamine hydrochlorate, 3.91 ml (27.9 mmoles) of Et$_3$N and stir for one night at room temperature.

Filter the DCU and evaporate to dryness. Take up with CH$_2$Cl$_2$. Wash with HCl N, then saturated NaHCO$_3$. Dry, evaporate. Purify by flash chromatography on 300 g of silica (inject with: CH$_2$Cl$_2$; elute with: CH$_2$Cl$_2$:MeOH:NH4; 95:5:0.5).

Recover 3.34 g of the least polar pure diastereoisomer (50%).

RMN (CDCl$_3$):

the least polar diastereoisomer:

δ9.1 (1H, s, CONHO); 7.5 (1H, d, CONH); 7.4 (5H, s, Ar—CH$_2$—O); 7.2 (2H, d, CH(Ar)); 6.8 (2H, d, CH(Ar)); 5.9 (1H, q, CONHCH$_3$); 4.9 (2H, s, ArCHO); 4.8 (1H, s, OH); 4.4 (1H, m, CHH-α(Tyr)); 3.8 (3H, s, OCH$_3$); 3.2–2.95 (2H, m, CH$_2$Ar); 2.7 (3H, d, CONHCH$_3$); 2.3 (1H, q, ONHCOCHCH$_3$); from 1.2 to 1.4 (3H, m, CH$_2$CH(CH$_3$)$_2$); 0.95–0.8–0.7 (9H, 3d, 3CH$_3$).

the most polar diastereoisomer:

N(2R)[1(R) phenylmethoxycarbamoyl)ethyl] 2(R) hydroxy 4-methyl L-tyrosine N-methylamide RMN (CDCl$_3$): δ10 (1H, broad s, CONHOH); 7.7 (1H, d, CONH); 7.35 (5H, m, ArCH$_2$O); 7.1 (2H, d, H(Ar)); 6.8 (2H, d, H(Ar)); 6.2 (1H, broad q, CONHCH$_3$); 4.9 (3H, s+m, Ar—CH$_2$—O+OH); 4.45 (1H, m, CH-α(Tyr)); 3.8 (3H, s, OCH$_3$); 3 (2H, m, CH$_2$Ar); 2.8 (3H, d, NHCH$_3$); 2.5 (1H, q, CHCH$_3$); 1.6 and 1.3 (3H, 2 m, CH$_2$CH); 1–0.85 and 0.7 (9H, 3d, 3CH$_3$).

d) N-2-(S)[1(S) hydroxycarbamoyl)-1 ethyl]-2(S) hydroxy-4-methyl pentanoyl O methyl L-tyrosine N-methylamide 3.28 g (6.8 mmoles) of the least polar diastereoisomer c) are solubilized in 40 ml of absolute ethanol under nitrogen. Add 300 mg of 10% Pd/c. Place under hydrogen atmosphere and stir for 2 hours at room temperature.

Filter the catalyst, rinse it with ethanol, evaporate to dryness.

Purify by flash chromatography on 200 g of silica (eluant: CH$_2$Cl$_2$:MeOH; 95:5).

Recover 1.81 g (or 65%) of product.

$[\alpha]_D$=+20.9° C. at t=20° C. (c=1, MEOH).

RMN (CDCl$_3$): δ10.75 (1H, s, HONHCO); 9.05 (1H, s, HONHCO); 7.9 (1H, q, CONHCH$_3$); 7.55 (1H, d, CONH); 7.05 (2H, d, CH(Ar)); 6.75 (2H, d, CH(Ar)); 5.42 (1H, s, OH); 4.5 (1H, m, CHα(Tyr)); 3.7 (3H, s, OCH$_3$); 2.6 (3H, d, CONHCH$_3$); 2.3 (1H, q, HONHCOCH—CH$_3$); 1.55 (2H, m, CH$_2$CH(CH$_3$)$_2$); 1.22 (1H, m, CH$_2$—CH(CH$_3$)$_2$); 0.85–0.7–0.6 (9H, 3d, 3CH$_3$).

EXAMKPLE 2

N-2-(S)[1(S)(hydroxycarbamoyl) ethyl]-2(S) hydroxy-4-methylpentanoyl 3-methyl-(S) valine N-methylamide a) N-[2(S)[1(S)((1,1 dimethyl) ethoxycarbonyl) ethyl]-2 (S) hydroxy 4-methylpentanoyl] 3 methyl (S) valine N-methylamide Solubilize 500 mg (1.9 mmoles) of intermediary 4 in 25 ml of dry $CH_2Cl_2$. Add 277 mg (1.9 mmoles) of (S) methyl 3-valine N-methylamide, 1.05 g of PyBop and 744 μl (4 mmoles) of diisopropylethylamine. Stir for one night at room temperature. Wash with HCl N, then saturated $NaHCO_3$. Dry, evaporate. Take up with AcOEt.

Filter on a silica gel. Evaporate.

Recover 598 mg (80%) of product.

RMN ($CDCl_3$): δ7.6 (1H, q, CON$\underline{H}$CH$_3$); 6.1 (1H, broad d, CON$\underline{H}$); 4.2 (1H, s, OH); 4.15 (1H, d, NH—C$\underline{H}$—tBu); 2.75 (4H, m, NHC$\underline{H}_3$ and tBuOCOC$\underline{H}$); 1.85 (1H, m, C$\underline{H}_2$CH); 1.7 (1H, m, CH$_2$C$\underline{H}$(CH$_3$)$_2$); 1.5 (9H, s, (C$\underline{H}_3$)$_3$CO); 1.4 (1H, m, C$\underline{H}_2$—CH); 1.15 (3H, d, COCHC$\underline{H}_3$); 1.1 (9H, s, CH—C(C$\underline{H}_3$)$_3$); 0.95 and 0.8 (6H, 2d, CH—(C$\underline{H}_3$)$_2$).

b) N 2(S) [1(S) (hydroxycarbonyl)ethyl)-2(S) hydroxy-4 methylpentanoyl] 3 methyl (S) valine N-methylamide Solubilize 580 mg of compound a) in 6 ml of dry $CH_2Cl_2$. Add 6 ml of trifluoroacetic acid. Stir for 5 hours at room temperature. Evaporate to dryness.

Take up 3 times with 10 ml of $CH_2Cl_2$ and 10 ml of heptane and evaporate to dryness.

Recover 480 mg of pure product (100%).

RMN (DMSO): δ8.05 (1H, q, CON$\underline{H}$CH$_3$); 7.05 (1H, d, CON$\underline{H}$); 5.2 (1H, very broad s, COO$\underline{H}$); 4.1 (1H, d, NHC$\underline{H}$CO); 2.7 (1H, q, HO$_2$CCHC$\underline{H}_3$); 2.55 (3H, d, NHC$\underline{H}_3$); 1.6 (2H, m, C$\underline{H}_2$—CH); 1.45 (1H, m, C$\underline{H}_2$—CH); 1 (3H, d, CO—CH—C$\underline{H}_3$); 0.9 (9H, s, C—(C$\underline{H}_3$)$_3$); 0.8 and 0.65 (6H, 2d, CH—(C$\underline{H}_3$)$_2$).

c) N-2-(S) [1(S) (hydroxycarbamoyl ethyl]-2 (S) hydroxy-4-methyl pentanoyl 3 methyl-(S) valine N-methylamide Solubilize 430 mg (1.3 mmoles) of compound b) in 9 ml of DMF. Add 204 mg (1.74 mmoles) of O-THP hydroxylamine, 195 mig (1.45 mmoles) of HOBT, 160 μl (1.45 mmoles) of N-methylmorpholine, 284 mg (1/48 mmoles) of WSC, HCl and stir for one night at room temperature.

Evaporate to dryness.

Take up with 10 ml of THF and 10 ml of HCl N and stir for 1 hour at room temperature.

Extract with AcOEt. Dry, evaporate.

Crystallize in ethyl ether. Recover 205 mg (or 45%).

RMN (DMSO): δ10.8 (1H, broad s, $\underline{H}$ONHCO); 9.1 (1H, broad s, HON$\underline{H}$CO); 8.05 (1H, q, CON$\underline{H}$CH$_3$); 7.45 (1H, d, CON$\underline{H}$); 5,5 (1H, s, O$\underline{H}$); 4.15 (1H, d, NHC$\underline{H}$CO); 2.6 (3H, d, NHC$\underline{H}_3$); 2.5 (1H, q, COC$\underline{H}$CH$_3$); 1.6 (2H, m, C$\underline{H}_2$C$\underline{H}$(CH$_3$)$_2$); 1.3 (1H, m, C$\underline{H}_2$CH(CH$_3$)$_2$); 1 (3H, d, C$\underline{H}_3$CHCO); 0.9 (9H, s, C(C$\underline{H}_3$)$_3$); 0.85 and 0.65 (6H, 2d, —CH—(C$\underline{H}_3$)$_2$).

EXAMPLE 3

N-2 (S) [(S) hydroxy (S) hydroxycarbamoyl methyl] 2(S) hydroxy 4-methyl pentanoyl L-4-chlorophenylalanine N-methylamide a) N-2-(S) [(S) 1,1 dimethylethoxycarbonyl (S) hydroxymethyl] 2(S) hydroxy 4-methyl pentanoyl L-4 chlorophenylalanine N-methylamide To 495 mg (1.9 mmoles) of intermediary 5 in 5 ml of dry dichloromethane, add a catalytic quantity of DMAP, 1 ml (5.8 mmoles) of DIPEA, then 0.74 ml (5.8 mmoles) of TMSCl. Stir for 30 minutes at 20° C., then add 255 mg (1.9 mmoles) of HOBT, 1 g (2 mmoles) of PyBop, 400 mg (2 mmoles) of 4-chlorophenylalanine N-methylamide and 1 ml (5.8 mmoles) of DIPEA. Stir for one night at 20° C. under nitrogen.

Add 385 mg (2 mmoles) of citric acid solubilized in 35 ml of methanol and stir for 30 minutes at 20° C.

Evaporate to dryness. Take up with AcOEt. Wash with HCl N, then $NaHCO_3$. Dry, evaporate.

Purify by flash chromatography (eluant: heptane:AcOEt; 40:60).

Recover 500 mg (58%) of pure product. MP: 168° C.

RMN ($CDCl_3$): δ7.3 (2H, d, H(Ar)); 7.2 (2H, d, H(Ar)); 6.9 (1H, d, N$\underline{H}$CO); 6.4 (1H, q, CON$\underline{H}$CH$_3$); 4.6 (1H, m, NHC$\underline{H}$CO); 4.1 (1H, d, C$\underline{H}$OH); 4(1H, s, O$\underline{H}$); 3.65 (1H, d, O$\underline{H}$; 3.15 (2H, m, C$\underline{H}_2$Ar); 2.75 (3H, d, NHC$\underline{H}_3$); 1.65 (3H, m, C$\underline{H}_2$C$\underline{H}$); 1.55 (9H, s, (C$\underline{H}_3$)$_3$C); 1 and 0.85 (6H, 2d, (C$\underline{H}_3$)$_2$CH).

b) N-2-(S)[(S)hydroxy (S) hydroxycarbonyl methyl] 2(S) hydroxy 4-methylpentanoyl L-4-chlorophenylalanine N-methylamide Solubilize 500 mg of compound a) in 5 ml of dry $CH_2Cl_2$. Add 1.25 ml of trifluoroacetic acid and stir for one night at 20° C. Evaporate to dryness.

Take up with a $CH_2Cl_2$ 50/heptane: 50 mixture and evaporate to dryness. Recover 440 mg or 100%.

RMN ($CDCl_3$): δ7.9 (1H, d, CON$\underline{H}$CH); 7.3 (2H, d, CH(Ar)); 7.15 (2H, d, C$\underline{H}$(Ar)); 5.65 (1H, q, CON$\underline{H}$CH$_3$); 4.55 (1H, m, NHC$\underline{H}$CO); 4 (1H, s, C$\underline{H}$OH); 3.1 (2H, m, C$\underline{H}_2$Ar); 2.8 (3H, d, NHC$\underline{H}_3$); 1.75 (1H, m, C$\underline{H}$(CH$_3$)$_2$); 1.65 (2H, m, C$\underline{H}_2$CH); 1 and 0.8 (6H, 2d, CH(C$\underline{H}_3$)$_2$);

c) N-2-(S)[(S) hydroxy (S) hydroxycarbamoyl methyl] 2(S) hydroxy 4-methyl pentanoyl L-4 chlorophenylalanine N-methylamide Solubilize 440 mg (1.1 mmoles) of compound b) in 8 ml of dry DMF. Add at 0° C. 180 mg (1.5 mmoles) of hydroxylamine OTHP, 180 mg (1.3 mmoles) of HOBT, 150 μl (1.3 mmoles) of N-methylmorpholine, 250 mg (1.3 mmoles) of WSC. Stir for one night at 20° C. Evaporate to dryness. Take up with 4 ml of THF and 4 ml of HCl N and stir for 4 hours at 20° C.

Concentrate to dryness. Purify by flash chromatography (eluant: $CH_2Cl_2$: MeOH:AcOEt; 90:10:1).

Recover 160 mg (35%) of pure product. MP: 185° C.

RMN (DMSO): δ10.7 (1H, broad s, $\underline{H}$ONHCO); 9 (1H, broad s, HON$\underline{H}$CO); 8.15 (1H, q, CON$\underline{H}$CH$_3$); 7.65 (1H, d, CON$\underline{H}$); 7.25 (2H, d, $\underline{H}$(Ar)); 7.20 (2H, d, $\underline{H}$(Ar)); 6 and 5 (2H, 2 very broad s, O$\underline{H}$); 4.45 (1H, m, COC$\underline{H}$NH); 3.85 (1H, s, C$\underline{H}$OH); 3.05 (1H, dd, C$\underline{H}_2$Ar), 2.95 (1H, dd, C$\underline{H}_2$Ar); 2.5 (3H, d, NHC$\underline{H}_3$); 1.55 (1H, dd, C$\underline{H}_2$—CH); 1.4 (1H, m, CH$_2$C$\underline{H}$); 1.25 (1H, dd, C$\underline{H}_2$CH); 0.8 and 0.6 (6H, 2d, CH(C$\underline{H}_3$)$_2$).

Examples 4 to 28 were synthesized in the same manner as example 2, witht the exception of example 7, synthesized in the same manner as example 1.

EXAMPLE 4

N-2(S)[1(S)(hydroxycarbamoyl)ethyl] 2(S) hydroxy4-methyl pentanoyl L-phenyl alanine N-methylamide M.P.: 174.2° (dec)

RMN (DMSO): δ10.75 (1H, broad s, $\underline{H}$ONHCO); 9.05 (1H, broad s, HON$\underline{H}$CO); 7.95 (1H, q, CON$\underline{H}$CH$_3$); 7.60

(1H, d, CONH); 7.20 (5H, m, H(Ar)); 5.40 (1H, broad s, COH); 4.45 (1H, m, NHCHCO); 2.95 (2H, dd, CH$_2$Ar); 2.60 (3H, d, NHCH$_3$); 2.30 (1H, q, COCHCH$_3$); 1.60 (1H, ddd, CH(CH$_3$)); 1.55 (1H, dd, CH$_2$CH); 1.20 (1H, m, CH$_2$CH); 0.85 (3H, d, CH$_3$CH); 0.70 and 0.50 (6H, 2d, CH(CH$_3$)$_2$).

EXAMPLE 5

N-2(S)[-1-(S)(hydroxycarbamoyl)-ethyl]-2(S) hydroxy-4-methyl 2entanol O methyl-L-tyrosine phenylmethylamide RMN (DMSO): δ10.75 (1H, broad s, HONHCO); 9.05 (1H, broad s, HONHCO); 8.5 (1H, t, NHCH$_2$Ar); 7.65 (1H, d, CONH); 7.25 (2H, m, CH(Ar)); 7.1 (5H, m, CH(Ar)); 6.8 (2H, d, CH(Ar)); 5.4(1H, s, OH); 4.6 (1H, m, NHCHCO); 4.25 (2H, m, NHCH$_2$Ar); 3.7 (3H, s, OCH$_3$); 2.9 (2H, m, CHCH$_2$Ar); 2.3 (1H, q, COCHCH$_3$); 1.55 (2H, m, CH$_2$CH); 1.2 (1H, dddd, CH(CH$_3$)$_2$); 0.85–0.7 and 0.55 (9H, 3d, CH$_3$CH and CH(CH$_3$)$_2$).

EXAMPLE 6

N-2(S)[-1(S) (hydroxycarbamoyl) 1(S) ethyl]-2(S) hydroxy 4-methyl pentanoyl leucinyl glycine methyl ester RMN (DMSO): δ10.8 (1H, broad s, HONHCO); 9.1 (1H, broad s, HONHCO); 8.5 (1H, t, CONH); 7.55 (1H, d, CONH); 5.45 (1H, s, OH); 4.45 (1H, m, CHCO); 3.85 (2H, d, NHCH$_2$CO); 3.60 (3H, s, OCH$_3$); 2.45 (1H, q, COCH—CH$_3$); from 1.8 to 1.35 (4H, m, CH$_2$—CH(CH$_3$)$_2$ and CH$_2$CH); from 1 to 0.6 (12H, m, —CH(CH$_3$)$_2$ twice); 0.6 (3H, d, COCHCH$_3$).

EXAMPLE 7

N-2(S) [-1-(S) hydroxycarbamoyl 1(S) ethyl] 2(S) hydroxy-3 methyl butanoyl O-methyltyrosine N-methylamide Synthesizd with intermediary 9.

RMN (DMSO): δ10.83 (1H, broad s, OHNHCO); 9.05 (1H, broad s, HONHCO); 7.9 (1H, q, NHCH$_3$); 7.4 (1H, d, NHCH); 7.1 (2H, d, H(Ar)); 6.8 (2H, d, H(Ar)); 5.60 (1H, s, OH); 4.48 (1H, m, NHCHCO); 3.7 (3H, s, OCH$_3$); 2.85 (2H, 2dd, CH$_2$Ar); 2.6 (1H, q, CHCH$_3$); 2.58 (3H, d, NHCH$_3$); 1.75 (1H, m, CH(CH$_3$)$_2$); 0.85 and 0.8 (6H, 2d, CH(CH$_3$)$_2$); 0.65 (3H, d, CHCH$_3$).

EXAMPLE 8

N-2(S)[1(S)(hydroxycarbamoyl)-1 ethyl] 2(S) hydroxy 4-methyl pentanoyl L-4-nitrophenylalanine N-methylamide Dec.: 207° C. (dec)

[α]$_D$=+17.7° at t=20° C. (c=1, MeOH).

RMN (DMSO): δ10.7 (1H, broad s, HONHCO); 9.1 (1H, broad s, HONHCO); 8.21 (2H, d, H(Ar)); 7.95 (1H, q, CONHCH$_3$); 7.7 (1H, d, CONH); 7.5 (2H, d, H(Ar)); 5.4 (1H, s, OH); 4.65 (1H, dd, NHCHCO); 3.1 (2H, m, CH$_2$Ar); 2.6 (3H, d, NHCH$_3$); 2.25 (1H, q, COCHCH$_3$); from 1.7 to 1.4 (2H, m, CH$_2$CH); 1.2 (1H, dd, CH$_2$CH); 0.85 (3H, d, CHCH$_3$); 0.75 and 0.45 (6H, 2d, CH(CH$_3$)$_2$).

EXAMPLE 9

N-2(S)[1(S) (hydroxycarbamoyl) 1(S) ethyl]2-(S) hydroxy-4-methyl pentanoyl L-4-amino phenylalanine N-methylamide RMN (DMSO): δ7.82 (1H, q, CONHCH$_3$); 7.50 (1H, d, CONH); 6.80 (2H, d, H(Ar)); 6.40 (2H, d, H(Ar)); 4.85 (2H, broad s, NH$_2$); 4.40 (1H, dd, NHCHCO); 2.70 (2H, d, CH$_2$Ar); 2.55 (3H, d, CH$_3$NH); 2,2 (1H, q, COCHCH$_3$); from 1.7 to 1.45 (2H, m, CH$_2$CH); 1.25 (1H, m, CH$_2$CH); 0.85 (3H, d, CHCH$_3$); 0.70 (6H, d, CH(CH$_3$)$_2$).

EXAMPLE 10

N-2(S) [-1(S) (hydroxycarbamoyl)-1 ethyl]-2(S) hydroxy-4-methyl pentanoyl L4-chlorophenylalanine N-methylamide

[α]$_D$=+17.8° at t=20° C. (c=1, MeOH)

RMN (DMSO): δ10.75 (1H, broad s, HONHCO); 9.05 (1H, HONHCO); 7.9 (1H, q, CONHCH$_3$); 7.6 (1H, d, CONH); 7.25 (2H, d, 2HAr); 7.2 (2H, d, 2H(Ar)); 5.4 (1H, broad s, OH); 4.5 (1H, dd, COCHNH); 2.9 (2H, d, CH$_2$Ar); 2.55 (3H, d, NHCH$_3$); 2.25 (1H, q, CHCH$_3$); 1.55 (1H, m, CH$_2$CH); 1.5 (1H, m, CH$_2$CH); 1.2 (1H, m, CH$_2$CH); 0.85 (3H, d, CHCH$_3$); 0.65 and 0.5 (6H, 2d, CH(CH$_3$)$_2$).

EXAMPLE 11

N-2(S)[-1(S)(hydroxycarbamoyl)-1 ethyl]-2(S) hydroxy 4-methyl pentanoyl L-4-bromophenylalanine N-methylamide MP: 214° C. (dec.)

RMN (DMSO): δ10.75 (1H, broad s, OHNHCO); 9.05 (1H, broad s, HONHCO); 7.95 (1H, q, CONHCH$_3$); 7.65 (1H, d, CONH); 7.4 (2H, d, H(Ar)); 7.1 (2H, d, 2H(Ar)); 5.4 (1H, s, OH); 4.5 (1H, dd, NHCHCO); 2.9 (2H, d, CH$_2$(Ar)); 2.55 (3H, d, NHCH$_3$); 2.25 (1H, q, CHCH$_3$); 1.5 (2H, m, CH$_2$CH); 1.2 (1H, m, CH$_2$CH); 0.8 (3H, d, CHCH$_3$); 0.65 and 0.5 (6H, 2d, CH(CH$_3$)$_2$).

EXAMPLE 12a

N-2(S)[-1(S) hydroxycarbamoyl-1(S) ethyl-2(S) hydroxy-4-methyl pentanoyl L-4-chlorophenylalanine N-(2-(4-morpholino)1-ethyl)-amide MP: 179° C. (dec.)

RMN (DMSO): δ10.75 (1H, broad s, OHNHCO); 9.05 (1H, broad s, HONHCO); 7.95 (1H, broad t, CONHCH$_2$—); 7.65 (1H, d, CONH); 7.25 (4H, dd, H(Ar)); 5,4 (1H, s, OH); 4.5 (1H, m, CHCO); 3.55 (4H, m, (CH$_2$)$_2$—O); 3.15 (2H, q, CONHCH$_2$); 2.9 (2H, dd, CH$_2$Ar); 2.35 (4H, m, N(CH$_2$)$_2$); 2.3 (3H, m, CONH—CH$_2$—CH$_2$, CHCH$_3$); 1.55 (2H, m, CH$_2$CH); 1.2 (1H, dd, CH$_2$CH); 0.85 (3H, d, CHCH$_3$); 0.7 and 0.55 (6H, 2d, CH(CH$_3$)$_2$).

EXAMPLE 12b

Hydrochlorate of example 12a

RMN (DMSO): δ10.8 (s, 1H, HONH); 10.7 (broad s, 1H, (CH$_2$)$_3$N$^+$—H, Cl$^-$); 9.05 (s, 1H, HONH); 8.5 (m, 1H, CONHCH$_2$); 7.65 (d, 1H, CONH); 7.3 (m, 4H, H(Ar)); 5.4 (s, 1H, OH); 4.55 (1H, m, NHCHCO); 4–3.6 (m, 4H, (CH$_2$)$_2$—O); 3.5–2.9 (m, 10H, CONHCH$_2$ and (CH$_2$)$_3$N$^+$H, Cl$^-$ and CH$_2$Ar); 2.25 (q, 1H, CHCH$_3$); 1.6 (m, 2H, CH$_2$CH); 1.2 (m, 1H, CH$_2$CH); 0.85 (d, 3H, CHCH$_3$); 0.7 and 0.5 (2d, 6H, CH(CH$_3$)$_2$).

EXAMPLE 13

N-2(S)[-1-(S)(hydroxycarbamoyl)-1 ethyl]-2(S) hydroxy-4-methylpentanoylL-4-chlorophenylalanine N-(2 methylthio-1-ethyl) amide RMN (DMSO): δ10.7 (1H, broad s, HONHCO); 9.05 (1H, s, OHNHCO); 8.2 (1H, t, CONH); 7.6 (1H, d, CONH);

7.25 (4H, q, H(Ar)); 5.35 (1H, s, OH); 4.6 (1H, m, NHCHCO); 3.2 (2H, dd, CH₂—Ar); 2.9 (2H, m, NHCH₂); 2.45 (2H, m, CH₂S); 2.25 (1H, q, CHCH₃); 2.05 (3H, s, SCH₃); 1.55 (2H, m, CH₂CH); 1.15 (1H, m, CH₂CH); 0.85 (3H, d, CHCH₃); 0.65 and 0.5 (6H, 2d, CH(CH₃)₂).

EXAMPLE 14

N-2(S)[1(S) hydroxycarbamoyl-1 ethyl]-2(S) hydroxy 4 methyl pentanoyl L-4-iodophenylalanine N-methylamide RMN (DMSO): δ10.75 (1H, sl, OHNHCO); 9.05 (1H, broad s, HONHCO); 7.95 (1H, q, CONHCH₃); 7.63 (1H, d, CONH); 7.6 (2H, d, H(Ar)); 7 (2H, d, HAr); 5.4 (1H, s, OH); 4.55 (1H, m, COCHNH); 2.88 (2H, dd, CH₂Ar); 2.55 (3H, d, NHCH₃); 2.25 (1H, q, CHCH₃); 1.55 (2H, m, CH₂CH); 1.2 (1H, m, CH₂CH); 0.85 (3H, d, CHCH₃); 0.7 and 0.5 (6H, 2d, CH(CH₃)₂).

EXAMPLE 15

N-2(S)[1(S) hydroxycarbamoyl-1 ethyl]2(S) hydroxy 4-methylpentanoyl L-4-iodophenylalanine N-(2 methylthio-1-ethyl) amide RMN (DMSO): δ10.7 (1H, broad s, OHNHCO); 9.1 (1H, broad s, HONHCO); 8.2 (1H, dd, CONHCH₂); 7.6 (3H, d, H(Ar) and d, CONH); 7.05 (2H, d, H(Ar)); 5.3 (1H, s, OH): 4.6 (1H, m, NHCHCO); 3.3 (2H, m, CH₂NH); 2.9 (2H, m, CH₂Ar); 2.5 (3H, CH₂S and CHCH₃); 2.1 (3H, s, SCH₃); 1.6 (2H, m, CH₂C); 1.2 (1H, m, CH₂CH); 0.9 (3H, d, CH—CH₃); 0.7 and 0.5 (6H, 2d, CH(CH₃)₂).

EXAMPLE 16

N-2(S)[1(S)hydroxy carbamoyl-1 ethyl]-2(S) hydroxy 4-methylpentanoyl L-4-fluorophenylalanine N-methylamide

M.P.: 186.5° C.

RMN (DMSO): δ10.75 (1H, s, HONHCO); 9.05 (1H, broad s, HONHCO); 7.9 (1H, q, CONHCH₃); 7.65 (1H, d, CONHCH); 7.2 (2H, dd, H(Ar)); 7.05 (2H, dd, H(Ar)); 5.4 (1H, s, COH); 4.55 (1H, m, COCHNH); 2.9 (2H, d, CH₂Ar); 2.6 (3H, d, NHCH₃); 2.3 (1H, q, CHCH₃); 1.6 (2H, m, CH₂CH); 1.2 (1H, m, CH₂CH); 0.85 (3H, d, CHCH₃); 0.7 and 0.55 (6H, 2d, CH(CH₃)₂).

EXAMPLE 17

N-2(S) hydroxy 3(S) hydroxycarbamoyl 2(S) 1(2-methyl) propyl hexanoyl L-4-chlorophenylalanine N-methyl amide RMN (DMSO): δ7.9 (1H, q, CONHCH₃); 7.6 (1H, d, CONH); 7.2 (4H, m, H(Ar)); 5.3 (1H, broad s, OH); 4.5 (1H, m, NHCHCO); 2.9 (2H, d, CH₂Ar); 2.6 (3H, d, NHCH₃); 2.15 (1H, q, CHCH₃); from 1.5 to 0.8 (7H, m, CH₂CH and CHCH₂CH₂CH₃); 0.8 and 0.7 (9H, 1t and 2d, 3CH₃).

EXAMPLE 18

N-2(S)[1(S)hydroxy carbamoyl-1 ethyl]-2 (S) hydroxy 4-methylpentanoyl L-3,4-dichlorophenylalanine N-methylamide MP: 216° C. (dec)

RMN (DMSO): δ10.7 (1H, s, HONHCO); 9.05 (1H, s, HONHCO); 7.95 (1H, q, CONHCH₃); 7.7 (1H, d, CONH); 7.5 (2H, 1d and 1s, H(Ar)); 7.2 (1H, d, H(Ar)); 5.45 (1H, s, OH); 4.55 (1H, m, NHCHCO); 2.9 (2H, d, CH₂Ar); 2.6 (3H, d, CONHCH₃); 2.25 (1H, q, CHCH₃); 1.55 (2H, m, CH₂CH); 1.2 (1H, m, CH₂CH); 0.85 (3H, d, CHCH₃); 0.6 and 0.5 (6H, 2d, CH(CH₃)₂).

EXAMPLE 19

N-2(S)[1(S)hydroxy carbamoyl-1 ethyl]-2 (S) hydroxy 4-methylpentanoyl L-3,4 dichlorophenylalanine N-hydroxyethyloxyethylamide RMN (DMSO): δ8.1 (1H, t, NHCH₂); 7.7 (1H, d, CONH); 7.5 (2H, dd, H(Ar)); 7.25 (1H, dd, H(Ar)); 5.5 (1H, broad s, COH); 4.6 (1H, m, COCHNH); 3.5 (2H, t, CH₂OH, 3.4 (4H, m, CH₂—O—CH₂); 3.2 (2H, m, NHCH₂); 3 (2H, d, CH₂Ar)); 2.3 (1H, q, CHCH₃); 1.5 (2H, m, CH₂CH); 1.2 (1H, m, CH₂CH); 0.85 (3H, d, CHCH₃); 0.7 and 0.5 (6H, 2d, CH(CH₃)₂).

EXAMPLE 20

N-2(S)[1(S)hydroxy carbamoyl-1 ethyl]-2 (S) hydroxy 4-methylpentanoyl L-2,4-dichlorophenylalanine N-methylamide The diastereoisomers were separated in step a (the least polar diastereoisomer)

MP: 193.5° C.

RMN (DMSO): δ10.8 (1H, s, CONHOH); 9.1 (1H, s, CONHOH); 7.9 (1H, q, CONHCH₃); 7.7 (1H, d, CONH); 7.5 (1H, s, H(Ar)); 7.4 (2H, 2d, H(Ar)); 5.4 (1H, s, OH); 4.6 (1H, m, COCHNH); 3.1 (2H, m, CH₂(Ar)); 2.6 (3H, d, NHCH₃); 2.3 (1H, q, CHCH₃); 1.5 (2H, m, CH₂CH); 1.2 (1H, m, CH₂CH); 0.8 (3H, d, CHCH₃); 0.7 and 0.5 (6H, 2d, CH(CH₃)₂).

EXAMPLE 21

N-2(S)[1(S)hydroxycarbamoyl-1 ethyl]-2(S) hydroxy-4-methylpentanoyl L-3,4-dichlorophenylalanine N-(2-methylthio-1-ethyl) amide RMN (DMSO): δ10.75 (1H, s, HONHCO); 9.05 (1H, s, HONH); 8.15 (1H, t, CONHCH₂); 7.7 (1H, d, CONHCH); 7.5 (1H, m, H(Ar)); 7.2 (1H, m, H(Ar)); 5.4 (1H, s, OH); 4.6 (1H, m, NHCHCO); 3.25 (2H, q, CONHCH₂); 2.95 (2H, m, CH₂Ar); 2.4 (2H, m, CH₂S); 2.28 (1H, q, COCHCH₃); 2.05 (3H, s, SCH₃); 1.55 (2H, m, CH₂CH(CH₃)₂); 1.2 (1H, m, CH₂CH(CH₃)₂); 0.85 (3H, d, COCHCH₃); 0.65 and 0.5 (6H, 2d, CH(CH₃)₂).

EXAMPLE 22

N-2(S)-[1(S) hydroxycarbamoyl-1 ethyl]-2(S) hydroxy-4-methylpentanoyl L-3-chlorophenylalanine N-methylamide The diastereoisomers were separated in step a (the least polar diastereoisomer)

RMN (DMSO): δ10.75 (1H, s, HONHCO); 9.1 (1H, s, HONHCO); 7.95 (1H, q, CONHCH₃); 7.7 (1H, dd, CONHCH); from 7.3 to 7.1 (4H, m, H(Ar)); 5.4 (1H, s, COH); 4.55 (1H, q, NHCHCO); 2.9 (2H, d, CH₂Ar); 2.6 (3H, d, NHCH₃); 2,24 (1H, q, COCHCH₃); from 1.7 to 1.45 (2H, m, CH₂CH(CH₃)₂); 1.2 (1H, m, CH₂CH(CH₃)₂); 0.85 (3H, d, COCHCH₃); 0.7 from 0.5 (6H, 2d, CH(CH₃)₂).

EXAMPLE 23

N-2(S) [1(S) hydroxycarbamoyl-1 ethyl]-2(S) hydroxy 4-methyl pentanoyl L-3,4-dichlorophenylalanine N-(2-(2-methoxyethoxy)1-ethyl)amide RMN (DMSO): δ10.75 (1H, very broad s, OHNHCO); 9.05 (1H, broad s, HONHCO); 8.15 (1H, m, CONHCH$_2$); 7.72 (1H, d, CONHCH); 7.5 (1H, d, H(Ar)); 7.48 (1H, dd, H(Ar)); 7.25(1H, dd, H(Ar)); 5.45 (1H, s, COH); 4.65 (1H, q, NHCHCO); from 3.5 to 3.2 (11H, m, CONHCH$_2$CH$_2$OCH$_2$CH$_2$OCH$_3$); 2.92 (2H, d, CH$_2$Ar); 2.25 (1H, m, COCHCH$_3$); 1.55 (2H, m, CH$_2$CH(CH$_3$)$_2$); 1.2 (1H, m, CH$_2$CH(CH$_3$)$_2$); 0.85 (3H, d, COCHCH$_3$); 0.7 and 0.5 (6H, 2d, CH(CH$_3$)$_2$).

EXAMPLE 24

N-2(S)[1(S) hydroxycarbamoyl-1 ethyl]-2(S) hydroxy-4-methylpentanoyl L-2,6-dichlorophenylalanine N-methylamide The diastereoisomers were separated in step a (the least polar diastereoisomer)

RMN (DMSO): δ10.75 (1H, s, HONHCO); 9.1 (1H, s, HONHCO); 8.1 (1H, q, CONHCH$_3$); 7.65 (1H, d, CONHCH); 7.4 (2H, d, H(Ar)); 7.2 (1H, t, H(Ar)); 5.45 (1H, s, COH); 4.75 (1H, m, NHCHCO); 3.3 (1H, dd, CH$_2$Ar); 3.1 (1H, dd, CH$_2$Ar); 2.6 (3H, d, NHCH$_3$); 2.2 (1H, q, COCHCH$_3$); 1.55 (2H, m, CH$_2$CH(CH$_3$)$_2$); 1.2 (1H, m, CH$_2$CH(CH$_3$)$_2$); 0.85 (3H, d, COCHCH$_3$); 0.6 and 0.3 (6H, 2d, CH(CH$_3$)$_2$).

EXAMPLE 25

N-2(S)[1(S) hydroxycarbamoyl-1 ethyl]-2(S) hydroxy-4-methylpentanoyl L-2,5-dichlorophenylalanine N-methylamide The diastereoisomers were separated in step a (the least polar diastereoisomer)

MP: 209–212° C.

RMN (DMSO): δ10.7 (1H, s, HONHCO); 9.1 (1H, s, HONHCO); 7.8 (1H, q, CONHCH$_3$); 7.7 (1H, d, CONHCH); 7.4 (2H, m, H(Ar)); 7.3 (1H, dd, H(Ar)); 5.4 (1H, s, COH); 4.6 (1H, m, NHCHCO); 3.0 (2H, m, CH$_2$Ar); 2.6 (3H, d, NHCH$_3$); 2.3 (1H, m, COCHCH$_3$); 1.5 (2H, m, CH$_2$CH(CH$_3$)$_2$); 1.2 (1H, m, CH$_2$CH(CH$_3$)$_2$); 0.9 (3H, d, COCHCH$_3$); 0.7 and 0.5 (6H, 2d, CH(CH$_3$)$_2$).

EXAMPLE 26

N-2-(S)[1(S) hydroxycarbamoyl-1 ethyl]-2(S) hydroxy-4-methylpentanoyl L-tryptophan N-methylamide RMN (DMSO): δ10.75 (1H, s, HONHCO); 9.1 (1H, s, HONHCO); 7.95 (1H, q, NHCH$_3$); 7.65 (1H, d, CONHCH); 7.5 (2H, m, H(Ar)); 7.25 (1H, d, H(Ar)); from 7.15 to 6.9 (3H, m, H(Ar)); 5.4 (1H, s, COH); 4.5 (1H, m, COCHNH); 3 (2H, m, CH$_2$Ar); 2.55 (3H, d, NHCH$_3$); 2.2 (1H, q, COCHCH$_3$); from 1.65 to 0.9 (3H, m, CH$_2$CH(CH$_3$)$_2$); 0.75 (3H, d, COCHCH$_3$); 0.6 and 0.4 (6H, 2d, CH(CH$_3$)$_2$).

EXAMPLE 27

N-2(S)[1(S) hydroxycarbamoyl-1 ethyl]-2(S) hydroxy-4-methylpentanoyl L-4-chlorophenylalanine N-(2-cyano-1-ethyl) amide IR: ν CN 2254 cm$^{-1}$
RMN (DMSO): δ10.75 (1H, s, HONHCO); 9.08 (1H, broad s, HONHCO); 8.5 (1H, q, CONHCH$_3$); 7.65 (1H, d, CONHCH); 7.25 (4H, dd, H(Ar)); 5.4 (1H, s, COH); 4.6 (1H, m, COCHNH); 3.2 (2H, m, CONHCH$_2$CH$_2$); 2.95 (2H, m, CH$_2$Ar); 2.6 (2H, t, CH$_2$CN); 2.25 (1H, q, COCHCH$_3$); 1.55 (1H, m, CH$_2$CH(CH$_3$)$_2$); 1.25 (2H, m, CH$_2$CH(CH$_3$)$_2$); 0.95 (3H, d, COCHCH$_3$); 0.65 and 0.5 (6H, 2d, CH(CH$_3$)$_2$).

EXAMPLE 28

N-2(S)[1(S) hydroxycarbamoyl-1 ethyl]-2(S) hydroxy-4-methylpentanoyl L-4-chlorophenylalanine N-oximino-2-amino-2-ethylamide This compound has been prepared from example 27.

Solubilize 130 mg (0.29 mmole) of compound of example 27 in 10 ml of n-butanol, add 1.01 ml of a solution of hydroxylamine base 0.56 M (or 0.57 mmoles) and heat for one night at 80° C. under nitrogen atmosphere; evaporate to dryness. Purify by flash chromatography on 10 g of silica (dry injection on 1 g of SiO$_2$). Elute CH$_2$Cl$_2$ 90:MeOH 10. Recover 74 mg or 53% of foam.

RMN (DMSO): δ10.7 (1H, broad s, HONHCO); 9 (1H, s, HONHCO); 8.8 (1H, s, C=NOH); 8 (1H, m, CONHCH$_2$); 7.62 (1H, m, CONHCH); 7.25 (2H, m, H(Ar)); 7.15 (2H, m, H(Ar)); 5.35 (2H, broad s, H$_2$NC=NOH); 4.6 (1H, q, COCHNH); 4 (1H, s, COH); 3.15 (2H, m, CONHCH$_2$—); 2.85 (2H, m, CH$_2$Ar); from 2.2 to 2.02 (3H, m, COCHCH$_3$ and CH$_2$—C=NOH); from 1.7 to 1 (3H, m, CH$_2$CH(CH$_3$)$_2$); 0.8 (3H, d, COCHCH$_3$); 0.65 and 0.55 (6H, 2d, CH(CH$_3$)$_2$).

EXAMPLE 29

N-2-(S)[(S) hydroxy-(S)hydroxycarbamoylmethyl)-2(S) hydroxy-4-methyl]pentanoyl O-methyl tyrosine N-methylamide Synthesized in the same manner as example 3.
MP: 199° C. (dec.)

RMN (DMSO): δ10.72 (1H, s, HONH); 9 (1H, s, HONH); 8.2 (1H, q, CONHCH$_3$); 7.6 (1H, d, CONH); 7.05 (2H, d, CH(Ar)); 6.8 (2H, d, CHAr); 6.1 (1H, d, OH); 4.85 (1H, s, OH); 4.38 (1H, m, NHCHCO); 3.9 (1H, d, CH—O); 3.7 (3H, s, OCH$_3$); 2.92 (2H, 2dd, CH$_2$Ar); 2.6 (3H, d, NHCH$_3$); 1.55 (1H, dd, CH$_2$CH); 1.45 (1H, m, CH(CH$_3$)$_2$); 1.28 (1H, dd, CH$_2$CH$_2$); 0.8 and 0.65 (2d, CH(CH$_3$)$_2$).

EXAMPLE 30

N-2(S)[1(S) hydroxycarbamoylmethyl]-2(S) hydroxy-4-methylpentanoyl L-3,4-dichlorophenylalanine N-methylamide

MP: 194.1° C.

RMN (DMSO): δ10.7 (1H, broad s, HONHCO); 9.0 (1H, s, HONHCO); 8.25 (1H, q, CONHCH$_3$); 7.7 (1H, d, CONHCH); 7.5 (1H, d, H(Ar)); 7.45 (1H, m, H(Ar)); 7.2 (1H, dd, H(Ar)); 6.05 (1H, d, COCHOH); 4.9 (1H, s, COH); 4.5 (1H, m, COCHNH); 3.9 (1H, d, COCHOH); from 3.15 to 2.2 (2H, m, CH$_2$Ar); 2.6 (3H, d, CONHCH$_3$); from 1.5 to 1.25 (3H, m, CH$_2$CH(CH$_3$)$_2$); 0.8 and 0.6 (6H, 2d, CH(CH$_3$)$_2$).

EXAMPLE 31

N-2(S)[(S) hydroxycarbamoyl(S) methoxy]methyl 2(S) hydroxy-4 methyl pentanoyl O-methyl tyrosine N-methylamide Synthesized in the same manner as example 2 from intermediary 6.

RMN (DMSO): δ10.9 (1H, broad s, OHNHCO); 9.2 (1H, broad s, HONHCO); 8.05 (1H, q, CONHCH$_3$); 7.55 (1H, d, CONH); 7.05 (2H, d, CH(Ar)); 6.8 (2H, d, CH(Ar)); 5.05 (1H, broad s, OH); 4.4 (1H, m, NHCHCO); 3.7 (3H, s, OCH$_3$); 3.6 (1H, s, CHOCH$_3$); 3.2 (3H, s, CHOCH$_3$); 2.9 (2H, m, CH$_2$Ar); 2.6 (3H, d, NHCH$_3$); 1.55 (3H, m, CH$_2$CH); 0.8 and 0.65 (6H, 2d, CH(CH$_3$)$_2$).

EXAMPLE 32

N-2-(S)[1(S)(hydroxycarbamoyl)ethyl]2(S) hydroxy 5-phenyl pentanoyl L-3-cyclohexylalanine 2 phenylethylamide Synthesized from intermediary 8.

RMN (DMSO): δ10.8 (1H, s, HONHCO); 9.1 (1H, s, HONHCO); 8.05 (1H, t, CONHCH$_2$); 7.5 (1H, d, CONH); from 7.3 to 7 (10H, m, H(Ar)); 5.45 (1H, s, OH); 4.35 (1H, m, NHCHCO); 3.18 (2H, q, NHCH$_2$CH$_2$); 2.6 (2H, t, CH$_2$CH$_2$Ar); 2.5 (3H, m, CHCH$_3$ and CH$_2$Ar); from 1.8 to 0.7 (17H, m: H cyclohex, CH$_2$-cyclohex; C(OH)CH$_2$CH$_2$); 1 (3H, d, CHCH$_3$).

EXAMPLE 33

N-2-(S)[1(S)(hydroxycarbamoyl)ethyl]2(S) hydroxy 5-phenylpentanoyl L-3,4-dichlorophenylalanine N-methylamide Synthesized from intermediary 8.

RMN (DMSO): δ10.7 (1H, s, CONHOH); 9 (1H, s, CONHOH); 7.9 (1H, q, CONHCH$_3$); 7.7 (1H, d, CONH); 7.5 (2H, 1d and 1s, H(Ar)); from 7,2 to 7 (6H, m, H(Ar)); 5.4 (1H, s, OH); 4.5 (1H, m, COCHNH); 2.9 (2H, m, CH$_2$Ar); 2.7 (1H, q, CHCH$_3$); from 2.5 to 2.3 (5H, m, CH$_2$CH$_2$Ar and NHCH$_3$); from 1.6 to 1.2 (4H, m, CH$_2$CH$_2$CH$_2$Ar); 0.5 (3H, d, CHCH$_3$).

EXAMPLE 34

N-2-(S)[(S)-hydroxy-(S)hydroxycarbamoylmethyl)-2(S)-hydroxy-4-methyl]pentanoyl-o-methyl-3-methyl-(S) valine N-methylamide Synthesized in the same manner as example 3.

RMN (DMSO): δ9 (s, 1H, HONH); 8.05 (q, 1H, CONHCH$_3$); 7.5 (d, 1H, CONH); 5.65 (d, 1H, OH); 5.35 (s, 1H, OH); 4.1 (d, 1H, NHCHCO); 3.9 (d, 1H, CHOH); 2.55 (d, 3H, NHCH$_3$); 1.6 (m, 2H, CH$_2$CH); 1.25 (m, 1H, CH$_2$CH); 0.9 and 0.7 (2d, 6H, CH(CH$_3$)$_2$).

EXAMPLE 35a

N-2(S)[1(S)-hydroxycarbamoyl-1 (S) ethyl]-2 (S)-hydroxy-4-methyl pentanoyl L-(3,4)-dichlorophenylalanine N-(2-(4-morpholino)1-ethyl) amide Synthesized in the same manner as example 2.

RMN (DMSO): δ10.7 (s, 1H, HONH); 9.05 (s, 1H, HONH); 8 (m, 1H, CONHCH$_2$); 7.7 (d, 1H, CONH); 7.5 (m, 2H, H(Ar)); 7.2 (dd, 1H, H(Ar)); 5.4 (s, 1H, OH); 4.6 (m, 1H, NHCHCO); 3.5 (m, 4H, (CH$_2$)$_2$—O); 3.2 (m, 2H, CONHCH$_2$); 2.9 (d, 2H, CH$_2$Ar); 2.4–2.2 (m, 7H, N(CH$_2$)$_2$ and CONHCH$_2$CH$_2$ and CHCH$_3$); 1.55 (m, 2H, CH$_2$CH); 1.2 (m, 1H, CH$_2$CH); 0.8 (d, 3H, CHCH$_3$); 0.7 and 0.5 (2d, 6H, CH(CH$_3$)$_2$).

EXAMPLE 35b

Hydrochlorate of example 35a

RMN (DMSO): δ10.8 (m 1H, (CH$_2$)$_3$N$^+$H, Cl$^-$); 10.7 (s, 1H, HONH); 9 (broad s, 1H, HONH); 8.5 (m, 1H, CONHCH$_2$); 7.8 (d, 1H, CONH), 7.5 (m, 2H, H(Ar)); 7.2 (dd, 1H, H(Ar)); 5.4 (broad s, 1H, OH); 4.55 (m, 1H, NHCHCO); 4–3.4 (m, 6H, (CH$_2$)$_2$—O and CONHCH); 3.1–2.9 (m, 8H, (CH$_2$)$_3$N$^+$H, Cl$^-$ and CH$_2$Ar); 2.2 (q, 1H, CHCH$_3$); 1.5 (m, 2H, CH$_2$CH); 1.2 (m, 1H, CH$_2$CH); 0.8 (3H, d, CHCH$_3$); 0.65 and 0.45 (2d, 6H, CH(CH$_3$)$_2$).

EXAMPLE 36

N-2(R)-[(1-thioethyl)] 2(R) hydroxy 4-methyl pentanoyl-o-methyl-L-tyrosine methylamide a) 2(R)-[1(4(methoxy)benzylmercapto)ethyl]2(R) hydroxy 4-methylpentanoyl-o-methyl-L-tyrosine methylamide.

Synthesized in the same manner as compound a) of example 2 from the intermediary 22 and o-methyl-L-tyrosine methylamide.

RMN (CDCl$_3$): δ7.3–7.15 (m, 5H, HAr and CONH); 6.8 (m, 4H, HAr); 6 (m, 1H, CONH); 4.7–4.5 (m, 1H, NHCHCO); 3.8 (2s and dd, 8H, 2OCH$_3$ and CH$_2$S); 3.05 (m, 2H, CH$_2$Ar); 2.9 (q, 1H, CHS); 2.7–2.6 (2d, 3H, CONHCH$_3$); 1.75 (d, 2H, CH$_2$CH); 1.65 (m, 1H, CH$_2$CH); 1–0.75 (m, 9H, CHCH$_3$ and CH(CH$_3$)$_2$).

b) N-2(R)-[(1-thioethyl)] 2(R) hydroxy 4-methyl pentanoyl-o-methyl-L-tyrosine methylamide To 0.2 g (0.39 mmole) of compound a) in 6.3 ml of ammonia at −60° C., add 56 mg (2.4 mmoles) of sodium. Stir for 10 minutes, then add ammonium chloride. Allow the ammonia to evaporate by raising to room temperature. The residue is taken up in H$_2$O and extracted with CH$_2$Cl$_2$. The organic phase is dried on sodium sulfate and evaporated.

The diastereoisomers are separatred by flash chromatography (eluant: CH$_2$Cl$_2$:AcOEt; 80:20). Recover 28 mg of the least polar diastereoisomer (28%).

RMN (CDCl$_3$): δ7.3 (d, 1H, CONH); 7.2 (d, 2H, HAr); 6.8 (d, 2H, HAr); 5.95 (m, 1H, CONHCH$_3$); 4.5 (m, 1H, NHCHCO); 3.8 (s, 3H, OCH$_3$); 3.2 (m, 1H, CHS); 3.05 (m, 2H, CH$_2$Ar); 2.7 (d, 3H, NHCH$_3$); 2.65 (s, 1H, OH); 1.8–1.6 (m, 3H, CH$_2$CH); 1.35 (d, 1H, SH); 1–0.8 (ddd, 9H, CH$_3$CH and CH(CH$_3$)$_2$).

IR (CHCl$_3$): νOH: 3619 cm$^{-1}$; νCO: 1675 cm$^{-1}$.

EXAMPLE 37

N-2 (R)-[1-thioethyl] 2(R) hydroxy 4-methyl pentanoyl-L3,4)-dichlorophenylalanine a) 2(R)-[1(4(methoxy)benzylmercapto)ethyl]2(R)-hydroxy 4-methylpentanoyl-L-(3,4)-dichlorophenylalanine Synthesized as example 34 a).

RMN (CDCl$_3$): δ7.3–6.9 (m, 8H, HAr and CONH); 6.3 (m, 0.7H, CONHCH$_3$); 6.1 (m, 0.3H, CONHCH$_3$); 4.6 (m, 1H, NHCHCO); 3.9 (2s, 3H, OCH$_3$); 3.8 (m, 2H, CH$_2$S); 3.2–2.8 (m, 2H, CH$_2$Ar); 2.75 (2d, 3H, NHCH$_3$); 1.7–1.5 (m, 3H, CH$_2$CH); 1.3 (m, 3H, CH$_3$CH); 1–0.7 (m, 6H, CH(CH$_3$)$_2$).

b) N-2 (R)-[1-thioethyl] 2(R) hydroxy 4-methyl pentanoyl-L-(3,4)-dichlorophenylalanine Synthesized in the same manner as compound 35 b).

RMN (CDCl$_3$): δ7.4 (d, 1H, CONH); 7.3 (m, 3H, HAr); 6.1 (m, 1H, NHCH$_3$); 4.6 (m, 1H, NHCHCO); 3.2–3 (m, 3H,

CHS and CH₂Ar); 2.7 (d, 3H, NHCH₃); 1.8–1.6 (m, 3H, CH₂CH); 1.3 (d, 1H, SH; 1–0.8 (m, 9H, CH₃CH, CH(CH₃)₂).

EXAMPLE 38

N-2(S)-[1(N-hydroxy-N-formyl)ethyl]2(S)-hydroxy4-methylpentanoyl-o-methyl L-tyrosine methylamide a) N-2(S)-[1(o-benzylhydroxylamino)ethyl] 2(S)-hydroxy-4-methylpentanoyl-o-methyl-L-tyrosine methylamide Synthesized in the same manner as compound a) of example 2 except for the purification performed by flash chromatography (eluant: heptane:AcOEt; 20:80 then 30:70).

RMN (DMSO): δ7.9 (m 1H, CONH); 7.6 (d, 1H, CONH); 7.25 (m 5H, HAr); 7.05 (dd, 2H, HAr); 6.75 (dd, 2H, HAr); 6.1 (d, 0.5H, NH); 5.95 (d, 0.5H, NH); 4.9 (s, 0.5H, OH); 4.85 (s, 0.5H, OH); 4.55 (s, 1H, OCH₂Ar); 4.5 (s, 1H, OCH₂Ar); 4.45 (m, 1H, NHCHCO); 3.7 (s, 3H, OCH₃); 3.1 (m, 0.5H, CHNH); 3 (m, 0.5H, CHNH); 2.7 (m, 2H, CHCH₂Ar); 2.55 (dd, 2H, NHCH₃); 1.7–1.3 (m, 3H, CH₂CH); 0.95–0.6 (m, 9H, CHCH₃ and CH(CH₃)₂).

IR (CHCl₃): νOH: 3454 cm⁻¹; νNH: 3401 cm⁻¹; νCO: 1675 cm⁻¹.

b) N-2(S)-[1-(N-formyl (o-benzylhydroxylamino)) ethyl] 2 (S)-hydroxy-4-methylpentanoyl-o-methyl-L-tyrosine methylamide To a solution of formic acid (85 μl; 2.24 mmoles) and acetic anhydride (0.22 ml; 2.24 mmoles) heated to 40° C. for 45 minutes, add 0.264 g (0.56 mmoles) of compound a) dissolved in 11 ml of CH₂Cl₂.

Stir at room temperature for 1 hour 30 minutes. Wash with an 80% NaHCO₃ solution, then with H₂O. Dry over sodium sulfate and evaporate under vacuum.

Recover 0.267 g (95%).

The product is a ≈50-50 mixture of diastereoisomers. Each diastereoisomer exists in the form of two RMN conformers.

RMN (DMSO): δ8–7.6 (m, 3H, CHO and CONH and COCHCH₃); 7.4 (m, 5H, HAr); 7 (m, 2H, HAr); 6.8–6.6 (m, 2H, HAr); 5.6–5.2 (m, 1H, OH); 5–4.5 (m, 3H, OCH₂Ar and NHCHCO); 3.7–3.6 (2s, 3H, OCH₃); 2.8 (m, 2H, CH₂Ar); 2.6 (m, 3H, NHCH₃); 1.6 and 1.4 (m, 3H, CH₂CH); 1.2 and 1 (d, 3H, CHCH₃); 0.8 and 0.65 (m, 6H, CH(CH₃)₂).

IR (CHCl₃); νOH: 3454 cm⁻¹; νNH: 3393 cm⁻¹; νCO: 1661 cm⁻¹.

c) N-2(S)-[1(N-hydroxy-N-formyl)ethyl] 2(S)-hydroxy 4-methylpentanoyl-o-methyl L-tyrosine methylamide To a 10% suspension of Pd/C (0.266 g) in 5 ml of MeOH, add 0.266 g of compound b) (0.53 mmole) in solution in 25 ml of MeOH.

Stir under hydrogen for 1 hour. Filter on celite and evaporate under vacuum.

Purify by flash chromatography (eluant CH₂Cl₂:MeOH; 97:3).

Recover 0.118 g (54%).

The product is a ≈50-50 mixture of diastereoisomers. Each diastereoisomer exists in the form of two RMN conformers.

RMN (DMSO+D₂O): δ8.2 and 8.1 and 7.8 and 7.7 (4s, 1H, CHO); 7 (m, 2H, HAr); 6.7 (m, 2H, HAr); 4.5 (m, 1H, NHCHCO); 4.2 and 3.7 (m, 1H, CHCH₃); 3.8 (s, 3H, OCH₃); 2.8 (m, 2H, CH₂Ar); 2.6 (2d, 3H, NHCH₃); 1.6–1.25 (m, 3H, CH₂CH); 1.2–0.6 (m, 9H, CHCH₃ and CH(CH₃)₂).

IR (CHCl₃): νOH: 3450 cm⁻¹; νNH: 3397⁻¹; νCO: 1664 cm⁻¹.

Biochemistry

Activity on Collagenase

The anti-collagenase activity of the compounds according to this invention is determined on the collagenase of the human monocytic stock U937 in accordance with the operating mode described by Cawston and Barrett (Anal. Biochem. 99, 340–345, 1979).

The collagenase was incubated at 27° C. for 16 hours with radiomarked collagen, and its activity was determined by the release of soluble peptides produced by the enzymatic breakdown of the collagen. The inhibiting concentration C150 for each compound was determined by measurement of the activity of the enzyme in the presence of the inhibitor at a concentration ranging between $10^{-7}$ and $10^{-12}$ M (the inhibitor is dissolved at a concentration of $10^{-2}$ M in DMSO, then diluted successively by tenths in the buffer: Tris, HCl 150 mM, pH 7.5; NaCl 0.15 M; CaCl₂ 10 mM).

Activity on Stromelysine

The anti-stromelysine activity of the compounds according to this invention was determined on stromelysine of human origin, in accordance with the operating mode described by Cawston, T. E., Galloway, W. A., Mercier, E., Murphy, G., Reynolds, J. J. (Biochem. J., 195, 159–165, 1981). The stromelysine was incubated at 37° C. for 16 hours with radiomarked transferrin, and its activity was determined by the release of the soluble peptides produced by the enzymatic breakdown of the transferrin. The inhibiting concentration C150 for each compound was determined by measurement of the activity of the enzyme in the presence of the inhibitor at a concentration ranging between $10^{-7}$ and $10^{-12}$ M (the inhibitor is dissolved in the same manner as for collagenase).

Activity on Gelatinase

The anti-gelatinase activity of the compounds according to the invention was determined on 72 kDa gelatinase of human origin, in accordance with the operating mode described by Knight, C. G., Willenbrock, F., Murphy, G. (FEBS Letters, 296 (3), 263–266, 1992).

The gelatinase was incubated at 37° C. for 10 minutes, and its activity was determined by the increase in fluorescence of the product of Mca-Pro-Leu breakdown of the Mca-Pro-Leu-Gly-Leu-Dpa-Ala-Arg-NH₂ synthetic substrate.

The inhibiting concentration C150 for each compound was determined by measurement of the activity of the enzyme in the presence of the inhibitor at a concentration ranging between $10^{-7}$ and $10^{-12}$ M (the inhibitor is dissolved at a concentration of $10^{-2}$ M in DMSO, then diluted successively by tenths in DMSO to $10^{-4}$ M, then in the buffer: Tris, HCl 50 mM+0.05% Brij 35; CaCl₂ 10 mM; NaCl 0.15 M).

The anti-gelatinase activity of the compounds according to the invention also was determined on 92 kDa or 72 kDa gelatinase of human origin, in accordance with the operating mode described by Harris, E. D., Krane, S. M.; (Biochem. Biophys. Acta, 258, 566–576, 1972).

The gelatinase was incubated at 37° C. for 16 hours with radiomarked gelatin, and its activity was determined by the release of the soluble peptides produced by the enzymatic breakdown of the gelatin. The inhibiting concentration C150 for each compound was determined by measurement of the activity of the enzyme in the presence of the inhibitor at a concentration ranging between $10^{-7}$ and $10^{-12}$ M (the inhibitor is dissolved in the same manner as for collagenase).

Inhibition of the Production of TNF in vitro

The capacity of the compounds according to this invention to inhibit the release of TNF was determined from the peritoneal macrophages of mice stimulated by LPS (Lang, F., Robert, J. M., Boucrot, P., Welin, K, Petit, J. Y., J. Pharmacol. Exp. Ther., 275, 171–176, 1995).

After an adhesion phase of 2 hours, the cells were treated for 1 hour with the compound to be tested at concentrations ranging between $10^{-6}$ to $10^{-9}$ M (the inhibitor is dissolved in DMSO at $10^{-2}$ M, then at $5.10^{-3}$ M in RPMI 1640 with 5% SVF, then diluted successively by tenths in the same medium), then stimulated by the addition of LPS (100 ng/ml in final concentration). Three hours later, the biological activity of the TNF in the supernatants was determined by a cytotoxicity test using the murine stock L929 in accordance with the operating procedure described by Band, G., Lin, C. W., Georgescu, H. I., Evans, C. H. (Bioch. Biophys. Acta, 1134, 309–318, 1982).

The pg/ml concentration of the TNF of the samples was determined from a murine αTNF standard curve, thus making it possible to define the inhibiting concentration C150 of the compounds studied. The results on collagenase, gelatinase, stromelysine and TNF are compiled in table 1.

Inhibition of the Breakdown of Cartilage in vivo

The activities of the compounds of example 1 and example 10 comparatively to the compound BB16 were determined in a model of breakdown of cartilage in accordance with the operating mode described by Bottomley, K. M. K., Griffith, S. R. J., Rising, T. G., Steward, A. (Brit. J. Pharmacol. 21, 287–289, 1988). Femoral head cartilage of the rat, wrapped in sterile cotton, is implanted subcutaneously on the backs of mice. After 21 days, the mice are euthanized, the cartilages recovered and weighed. The animals are treated each day, twice a day, with one 10-mg/kg dose i.p.

The compound of example 10 inhibits weight loss of the cartilage by 65%, while the compound of example 1 inhibits the lattter in the same manner as comparator 1: BB16; that is, 42% (p<0.05).

Inhibition of Septic Shock

Septic shock is induced in female Balb/c mice in accordance with the procedure described by Mohler, K. M. et al. (Nature, 370, 218–220, 1994). Briefly, the shock is induced by i.p. injection of 20 mg of D-galactosamine and i.v. injection of 20 ng of LPS. The survival of the animals is evaluated for the following 48 hours.

The products to be tested are injected i.p. 30 minutes prior to induction of the shock. The compounds according to the invention protect from shock from 10 to 50 mg/kg. For instance, the compound of example 10 protects at 50 mg/kg.

Inhibition of Production of αTNF in vivo

The injection of LPS in mice (100 μg/mouse i.p.) induces the production of αTNF, the plasmatic concentration of which is maximal at 60–90 minutes (Sekut, L., Menius, J. A., Brackeen, M. F., Connolly, K. M., J. Lab. Clin. Med., 124, 6, 613–820, 1994).

αTNF is titrated by its cytotoxicity on L929 cells (Flick, D. A., Gilford, G. E., J. Immunol. Methods, 68, 167–175, 1984).

The products to be tested are administered i.p. or p.o. prior to injection of LPS.

The compounds according to the invention inhibit the production of αTNF between 1 and 50 mg/kg.

Inhibition of Release of αTGF

The compounds of this invention were tested in accordance with the methods of examples 2 and 3 described in patent WO 96/25156 and inhibit the release of αTGF.

Determination of Bioavailablity

The compounds of this invention were administered i.p. or p.o. between 1 and 50 mg/kg to mice: the blood levels then were determined by an ex-vivo bioassay according to Wang X. et al. (Cancer Res., 54, 4726–4728, 1994). The results are presented in Table 2. The introduction of an OH group systematically increases the bioavailability of the products.

TABLE 1

| | | C150 (nM) | | | |
| --- | --- | --- | --- | --- | --- |
| | | | gelatinase | | C150 |
| Structure, JL | collagenase | 92 kDa* | 72 kDa** | stromelysine | (μM) TNF |
| | 5 | 1 | 1 | 15 | 1 |

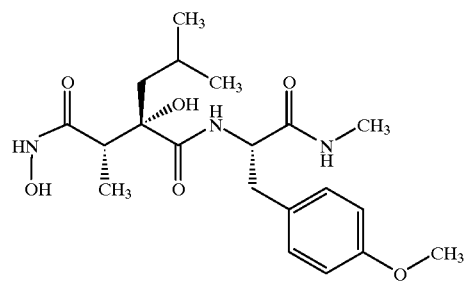

TABLE 1-continued
| Structure, JL | C150 (nM) | | | | C150 (μM) TNF |
|---|---|---|---|---|---|
| | collagen-ase | gelatinase 92 kDa* | 72 kDa** | strome-lysine | |
| 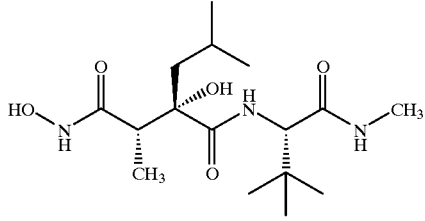 | 18 | 16 | 3.4 | 60 | NT |
| 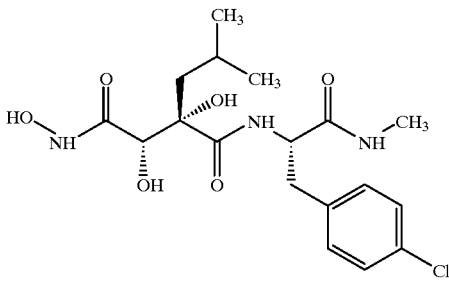 | 50 | 54 | 6.7 | >1000 | 3.2 |
| 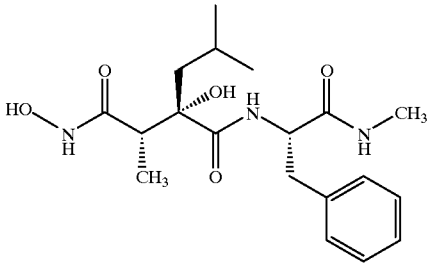 | 36 | 10 | 1.6 | 29 | NT |
| 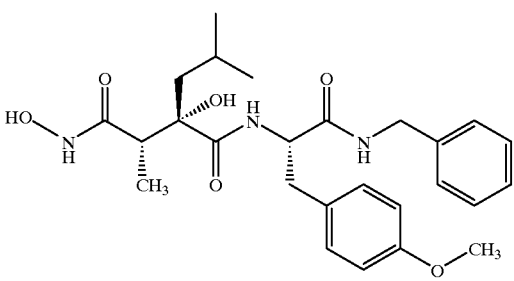 | 12 | 0.5 | 2.4 | 11 | NT |
| 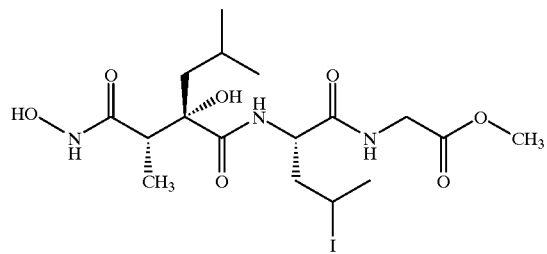 | 24 | 21 | 8.5 | 45 | NT |

TABLE 1-continued

| Structure, JL | collagen-ase | C150 (nM) gelatinase 92 kDa* | 72 kDa** | strome-lysine | C150 (μM) TNF |
|---|---|---|---|---|---|
| (structure) | 30 | 17 | 18 | NT | 2 |
| (structure) | 7 | 1.4 | 1.9 | 28 | ≦0.38 |
| (structure) | 11 | 2 | 1.6 | 50 | 2.2 |
| (structure) | 4 | 2 | 1 | 48 | 0.4 |

TABLE 1-continued

| Structure, JL | C150 (nM) | | | | C150 ($\mu$M) TNF |
|---|---|---|---|---|---|
| | collagen-ase | gelatinase | | strome-lysine | |
| | | 92 kDa* | 72 kDa** | | |
| (structure with 4-Br phenyl) | 10 | 2 | 2 | 37 | 0.61 |
| (structure with 4-Cl phenyl) | 23 | 9 | 10 | 15 | 0.51 |
| (structure with morpholinoethyl amide, 4-Cl phenyl) | 22 | 8 | NT | NT | 1.6 |
| (structure with methylthioethyl amide, 4-Cl phenyl) | 10 | 0.005 | 1.6 | 20 | 0.15 |
| (structure with 4-I phenyl) | 2 | 0.2 | 0.3 | 12 | 0.4 |

TABLE 1-continued
| Structure, JL | C150 (nM) | | | | C150 ($\mu$M) |
| --- | --- | --- | --- | --- | --- |
| | collagen-ase | gelatinase | | strome-lysine | TNF |
| | | 92 kDa* | 72 kDa** | | |
| 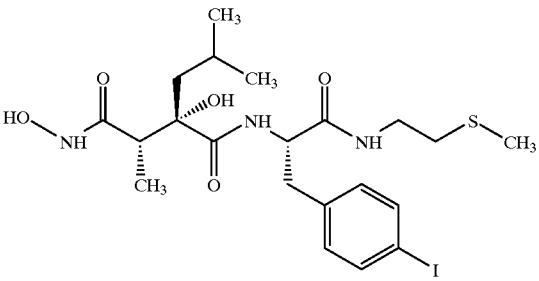 | 32 | 0.001 | 1.3 | 38 | 4.5 |
| 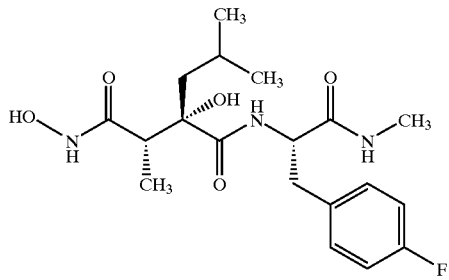 | 14 | 2 | 1.2 | NT | 0.6 |
| 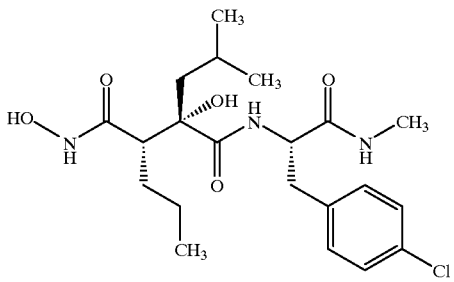 | NT | 1.6 | 1.6 | NT | 0.27 |
| 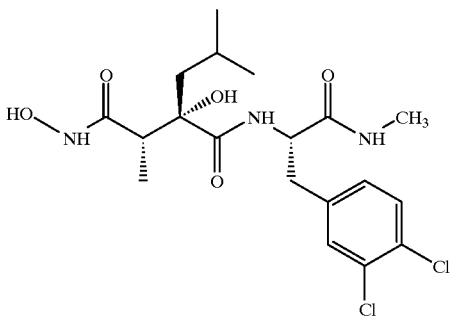 | 2 | 0.002 | 0.4 | 6 | ≤0.14 |

TABLE 1-continued

| Structure, JL | collagenase | C150 (nM) gelatinase 92 kDa* | 72 kDa** | stromelysine | C150 (μM) TNF |
|---|---|---|---|---|---|
| (structure with 3,4-dichlorobenzyl and ethoxyethanol amide) | 7 | 0.001 | 0.7 | NT | 0.5 |
| (structure with 2,4-dichlorobenzyl and N-methyl amide) | 3.7 | 0.2 | 1.6 | NT | 1 |
| (structure with 3,4-dichlorobenzyl and methylthioethyl amide) | 5 | 83% | NT | NT | 0.4 |
| (structure with 3-chlorobenzyl and N-methyl amide) | 2.4 | NT | NT | NT | 0.13 |

TABLE 1-continued

| Structure, JL | collagen-ase | C150 (nM) gelatinase 92 kDa* | 72 kDa** | strome-lysine | C150 (μM) TNF |
|---|---|---|---|---|---|
| (structure) | NT | 60% | 0.14 | NT | 0.37 |
| (structure) | NT | NT | NT | NT | NT |
| (structure) | NT | NT | NT | NT | NT |
| (structure) | NT | 0.6 | NT | NT | 4.4 |

TABLE 1-continued
| Structure, JL | C150 (nM) | | | | C150 ($\mu$M) |
| --- | --- | --- | --- | --- | --- |
| | collagen-ase | gelatinase | | strome-lysine | TNF |
| | | 92 kDa* | 72 kDa** | | |
| 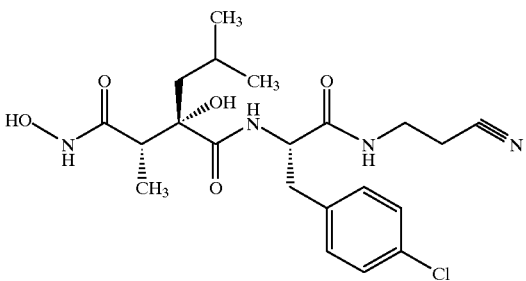 | NT | 1.7 | NT | NT | NT |
| 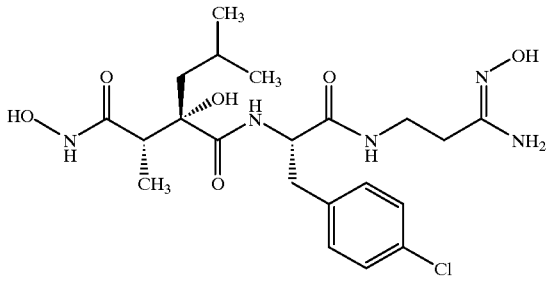 | 26 | 1.6 | NT | NT | NT |
| 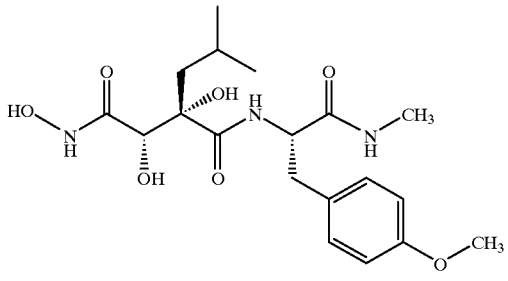 | 26 | 80 | 13 | 30,000 | NT |
| 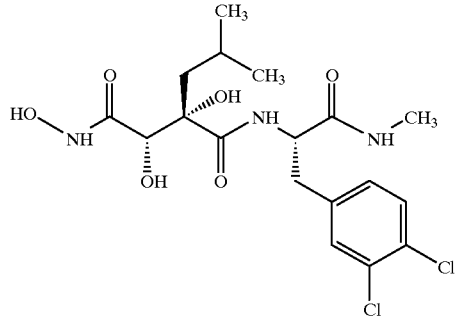 | 11 | 7 | NT | >1,000 | 3.6 |

TABLE 1-continued
| Structure, JL | C150 (nM) | | | | C150 (μM) TNF |
|---|---|---|---|---|---|
| | collagen-ase | gelatinase 92 kDa* | 72 kDa** | strome-lysine | |
| 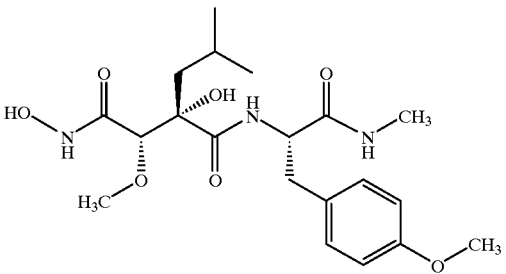 | 120 | 140 | 18 | 90 | NT |
| 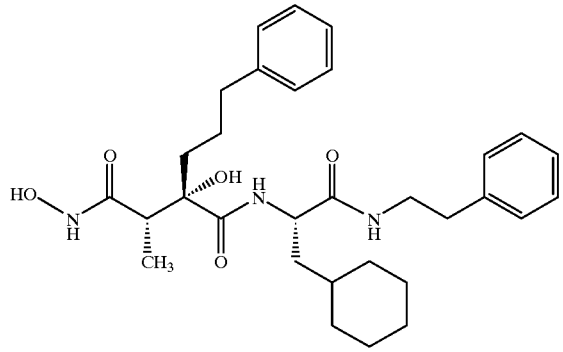 | NT | 1.9 | 0.8 | NT | >1 |
| 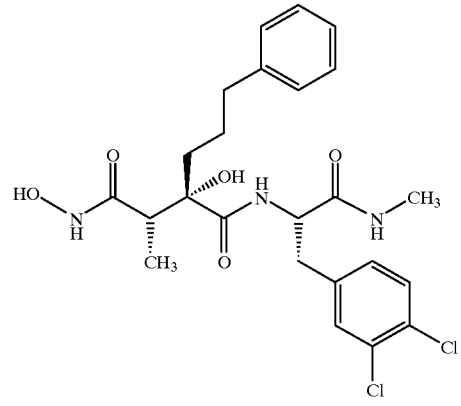 | 225 | 86% | 0.01 | NT | 0.58 |
| 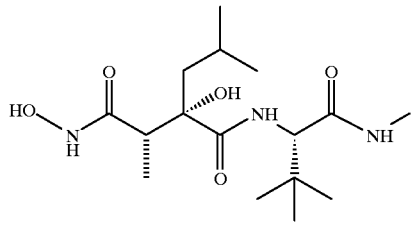 | 34 | NT | NT | NT | NT |

TABLE 1-continued

| Structure, JL | C150 (nM) | | | | C150 (μM) |
| | collagen-ase | gelatinase 92 kDa* | gelatinase 72 kDa** | strome-lysine | TNF |
|---|---|---|---|---|---|
| | 6 | 0.38 | NT | NT | 0.86 |
| | 4 | 1.1 | NT | NT | 0.3 |
| | 500 | 23 | NT | NT | 3 |
| | >1,000 | 70 | NT | NT | 2 |

TABLE 1-continued

| Structure, JL | C150 (nM) | | | | C150 ($\mu$M) |
| --- | --- | --- | --- | --- | --- |
| | collagen-ase | gelatinase | | strome-lysine | TNF |
| | | 92 kDa* | 72 kDa** | | |
| [structure: leucine-containing hydroxamate with N-formyl-N-hydroxy group and methoxyphenyl (tyrosine methyl ether) amide] | 130 | 17 | NT | NT | 3.2 |
| [structure: hydroxamate with leucine side chain, methyl group, and methoxyphenyl amide] | 5 | 7 | 0.6 | 10 | 0.14 |
| [structure: hydroxamate with OH, leucine side chain, and tert-butyl amide] | 4 | 11 | 0.5 | 47 | 0.14 |

*Test performed with radiomarked gelatin
**: performed on synthetic substrate
NT: not tested

TABLE 2

| PRODUCT (50 mg/kg) | I.p. method ($\mu$g/ml) | | | | | P.o. method ($\mu$g/ml) | | | | | | |
| --- | --- | --- | --- | --- | --- | --- | --- | --- | --- | --- | --- | --- |
| | 10' | 20' | 40' | 1 h | 24 h | 5' | 10' | 20' | 30' | 40' | 1 h | 24 h |
| [structure: hydroxamate with leucine side chain, methyl group, and methoxyphenyl amide] | 0.2 | <0.1 | <0.1 | | | | <0.1 | <0.1 | | <0.1 | | |

TABLE 2-continued

| | I.p. method (μg/ml) | | | | | P.o. method (μg/ml) | | | | | | |
|---|---|---|---|---|---|---|---|---|---|---|---|---|
| PRODUCT (50 mg/kg) | 10' | 20' | 40' | 1 h | 24 h | 5' | 10' | 20' | 30' | 40' | 1 h | 24 h |
| [structure 1] | 23 | 8.7 | | 0.77 | <0.5 | | 4.2 | 2.1 | | | 0.58 | <0.5 |
| [structure 2] | 30 | 27 | 18 | | | | 2.3 | 1.2 | | | | 0.9 |
| [structure 3] | 87 | 13 | 1.7 | 0.3 | | | 5.1 | 3.1 | | | 0.4 | <0.3 |
| [structure 4] | | | | | | 0.6 | 0.3 | 0.6 | | | | |
| [structure 5] | 0.7 | 0.5 | 0.1 | | | | 0.1 | 0.1 | | | | |

TABLE 2-continued

| | I.p. method (μg/ml) | | | | | P.o. method (μg/ml) | | | | | | |
|---|---|---|---|---|---|---|---|---|---|---|---|---|
| PRODUCT (50 mg/kg) | 10' | 20' | 40' | 1 h | 24 h | 5' | 10' | 20' | 30' | 40' | 1 h | 24 h |
| (structure) | 6 | 5 | 1.8 | | | | 1.25 | 0.8 | | | 0.45 | LD |
| (structure) | 4.5 | 7.8 | 4.4 | | | | 0.1 | 0.1 | | | | LD |
| (structure) | 20 | 9 | 47 | | | 2.2 | 4.3 | 0.3 | | | 0.5 | 0.17 |
| (structure) | 20 | 0 | 4 | | | | 10 | 9 | | | 9 | 9 |
| (structure) | 56 | 22 | 3.5 | | | NT | NT | NT | NT | NT | NT | NT |

What is claimed is:
1. Compounds of the following general formula (X):

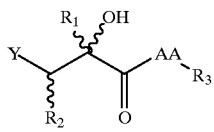

in which:
Y represents:
—CONHOH, or
—SH, or
a group with the formula

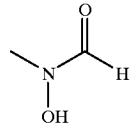

or
a group with the formula

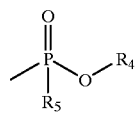

in which:
$R_4$ represents —H, or a $C_1$ to $C_6$ alkyl group, or a phenylalkyl group in which the alkyl group is $C_1$ to $C_6$,
$R_5$ represents a group with the formula

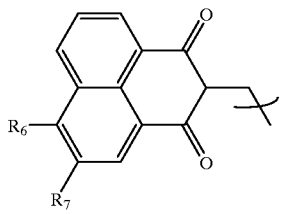

in which:
$R_6$ represents —H, or a $C_1$ to $C_6$ alkoxy group, or a benzyloxy group,
$R_7$ represents —H, or a halogen atom
$R_1$ represents:
a $C_3$ to $C_{16}$ linear or branched, or $C_3$ to $C_6$ cyclized alkyl chain, said chain comprising a heteroatom,
a phenoxyalkyl or phenylalkyl group, substituted or unsubstituted, or a heteroarylalkyl group, the alkyl group being $C_2$ to $C_5$,
$R_2$ represents:
a hydrogen atom, or,
a $C_1$ to $C_5$ alkyl or $C_2$ to $C_5$ alkylidene group, or
a hydroxyl, a $C_1$ to $C_6$ alkoxy or a benzyloxy, provided that Y represents —CONHOH when $R_2$ represents a hydroxyl, or
a hydroxymethyl, or $C_1$ to $C_6$ alkoxymethyl group, or
an arylalkyl group in which the alkyl portion is $C_1$ to $C_6$, an aryloxymethyl group, an arylthiomethyl group, a heteroarylthiomethyl group, in which aryl designates a substituted or unsubstituted phenyl remainder —$OCH_3$, a linear or branched $C_1$ to $C_3$ alkyl group, a halogen, an amine group, or
a phthalimide alkyl group in which the alkyl portion is $C_1$ to $C_6$, or
an alkoxycarbonmethyl group, a benzyloxycarbonylmethyl, an acetylmethyl, provided that Y represents —SH in these three cases,
AA represents an amino acid, or an amino acid chain a group with the formula

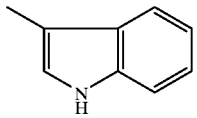

$R_3$ represents a group with the formula —NH—$(R_8)_n$—$R_9$
in which:
n represents 0 or 1,
$R_8$ represents a linear or branched alkyl chain, with 1 to 8 carbon atoms unsubstituted or substituted one or several heteroatoms,
$R_9$ represents a hydrogen atom or a methyl, nitrile, morpholino, phenyl, methoxy, hydroxyl, thiomethyl group, or a group with the formula —CH($NH_2$)=N—OH, or a —N($CH_3$)$_2$ group.

2. The compounds according to claim 1, having the following formula (Xa):

(Xa)

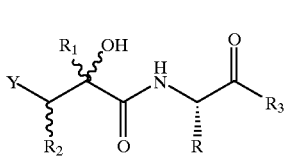

in which:
Y represents:
—CONHOH,
$R_1$ represents:
—CH($CH_3$)$_2$,
—$CH_2$—CH($CH_3$)$_2$, or

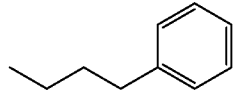

$R_2$ represents:
an alkyl group with 1 to 5 carbon atoms,
a hydroxyl, or
an alkoxy group with 1 to 5 carbon atoms,
R represents:
—C($CH_3$)$_3$,
—$CH_2$—CH($CH_3$)$_2$,

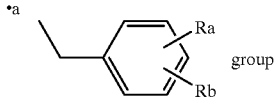

aromatic or nonaromatic, in which $R_a$ and $R_b$, independently of one another, represent —H, —Cl, —Br, —I, —F, —$OCH_3$, —$NO_2$, —$NH_2$, or a group with the formula

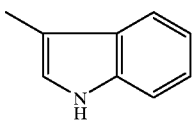

$R_3$ represents a —NH—$(CH_2)_{n1}$—$R_9$ group in which:
  $n_1$ represents 0, 1 or 2,
  $R_9$ represents —$CH_3$, —C≡N, —COOH$CH_3$, —$SCH_3$, —O—$(CH_2)_2$—OH, —O—$(CH_2)_2$—$OCH_3$, —CH($NH_2$)=N—OH,

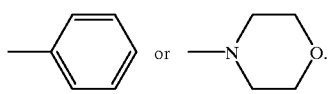

3. The compounds according to claim 2, wherein the $R_1$ and $R_2$ substituents are positioned in anti orientation in relation to the succinic residue in accordance with the following formula (XI.1):

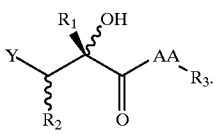

(XI.1)

4. Compounds according to claim 1, wherein R represents a group with the formula

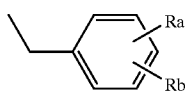

in which $R_a$ and $R_b$ represent a halogen atom.

5. The compounds according to claim 1, wherein $R_3$ represents a group with the formula

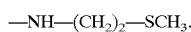

—NH—$(CH_2)_2$—$SCH_3$.

6. A mixture comprising compounds with the following formula (XI.1):

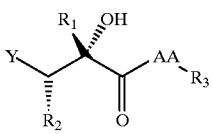

(XI.1)

in which Y, $R_1$ and $R_2$, AA and $R_3$ are such as defined in claim 1, and compounds with the following formula (XI.2):

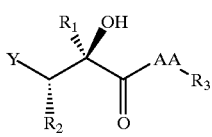

(XI.2)

in which Y, $R_1$, $R_2$, AA and $R_3$ have the meaning indicated hereinabove, the proportion of the compounds (XI.1) and (XI.2) in the mixture being approximately 50% to approximately 99% for the compound of formula (XI.1) and approximately 50% to approximately 1% for the compound of formula (XI.2).

7. The compounds according to claim 1, selected from the group consisting of:

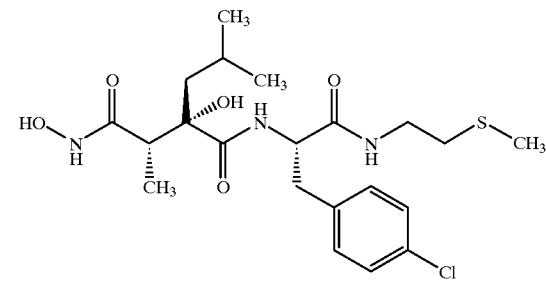

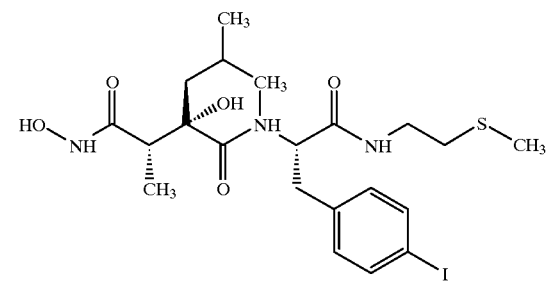

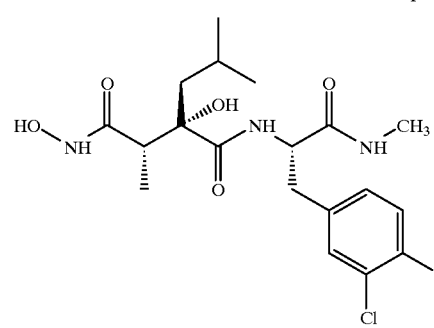

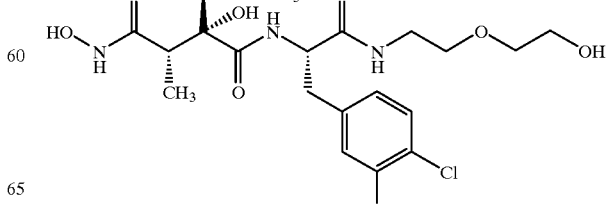

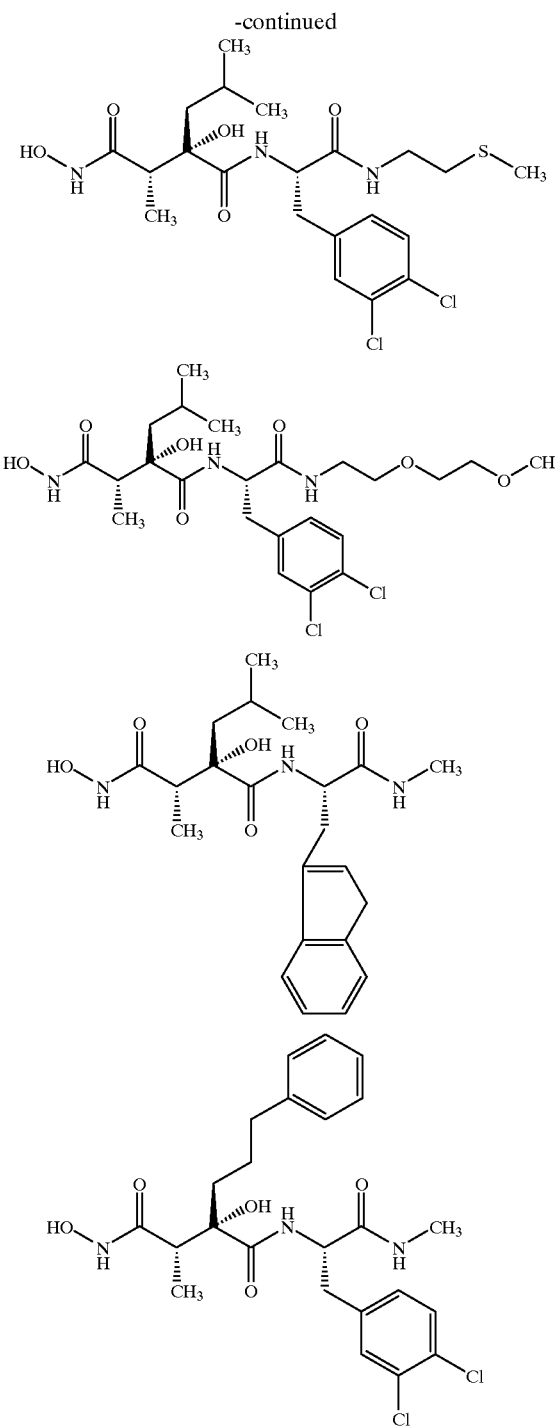

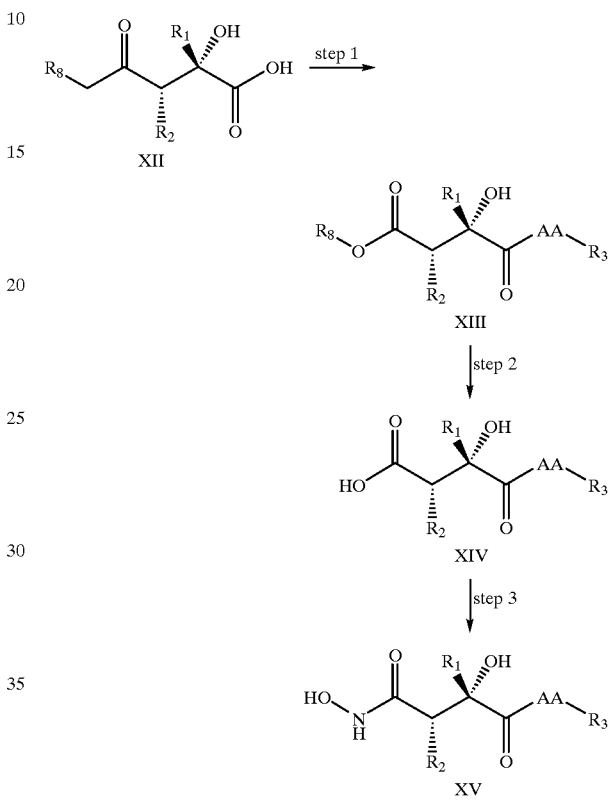

8. A pharmaceutical composition comprising, as an active principle at least one of the compounds of claim 2, in combination with an acceptable pharmaceutical vehicle.

9. The pharmaceutical composition according to claim 8, which is in a form which may be administered orally, parenterally or rectally.

10. The pharmaceutical composition according to claim 8, wherein the dosage of active principle is approximately 0.1 to approximately 500 mg/kg/day.

11. The pharmaceutical composition according to claim 8, which is in a form which may be administered orally, in a unit dosage of 1 mg to 250 mg of active principle per dose, at the rate of 1 to 4 doses per day.

12. The pharmaceutical composition according to claim 8, which is in a form which may be administered parenterally, in a unit dosage of 1 µg to 50 mg of active principle per injection, at the rate of 1 to 2 injections per day.

13. A process for preparation of the compounds of claim 1, wherein Y represents —CONHOH (XV) comprising the following steps:

wherein:

step 1 comprises condensing α-hydroxysuccinic acid XII, wherein $R_8$ is a protective group compatible with the various elements of the molecule with an AA-$R_3$ residue where AA and $R_3$ are such as defined in claim 2, by a method of coupling used in peptide synthesis, step 2 comprises hydrolyzing the ester XIII obtained in the preceding step into carboxylic acid XIV with trifluoroacetic acid, step 3 comprises forming hydroxamic acid XV by reacting hydroxylamine, protected O hydroxylamine or diprotected N,O hydroxylamine, with a coupling reagent DCC/HOBT or WSC/HOBT at room temperature in a solvent THF, $CH_2Cl_2$, or DMF for 1 to 24 hours, wherein if $R_2$=OH, the alcohols are protected prior to said coupling; the (di)protected O or N—O hydroxylamines are deprotected according to the nature of the protective group.

14. The compounds according to claim 1, wherein $R_7$ is Cl or Br.

15. The compounds according to claim 1, wherein $R_1$ is a $C_3$ to $C_{16}$ linear or branched, or $C_3$ to $C_6$ cyclized alkyl chain comprising O, S, and/or N.

16. The compounds according to claim 1, wherein $R_2$ is a phenyl substituted by OH.

17. The compounds according to claim 1, wherein $R_2$ is a Cl or Br.

18. The compounds according to claim 1, wherein $R_2$ is an amine group selected from the group consisting of $NH_2$, $NHCOCH_3$, $CHCOOR_{10}$, wherein $R_{10}$ is a linear or branched $C_1$ to $C_3$ alkyl group.

19. The compounds according to claim 1, wherein $R_2$ is a methoxycarbonmethyl group or a ethoxycarbonmethyl group.

20. The compounds according to claim 1, wherein AA represents an amino acid in an absolute S configuration and which has the formula

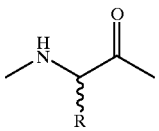

wherein R represents:
a $C_1$ to $C_4$ linear or branched alkyl chain,
a —$CH_2$—Y group in which Y represents a ring of 4 to 6 carbon atoms which may be substituted by one of several heteroatoms, said ring being aromatic or nonaromatic, substituted by one or several —$OCH_3$, —$NO_2$, —$NH_2$ groups, or by one or several halogen atoms.

21. The compounds according to claim 20, wherein Y represents a ring of 4 to 6 carbon atoms which may be substituted by O, S and/or N, said ring being aromatic or nonaromatic and substituted by one or several halogen atoms.

22. The compounds according to claim 20, wherein Y represents a ring of 4 to 6 carbon atoms which may be substituted by one or several heteroatoms, said ring being aromatic or nonaromatic and substituted by Cl, —Br, —F and/or —I.

23. The compounds according to claim 1, wherein $R_8$ is a linear or branched alkyl chain, with 1 to 8 carbon atoms substituted or unsubstituted by O and/or S.

24. The compounds according to claim 2, wherein $R_2$ is a methyl or propyl.

25. The compounds according to claim 2, wherein $R_2$ is a methoxy group.

26. The pharmaceutical composition according to claim 8, wherein the active principle is in a form which may be administered orally and is in a unit dosage of from 10 mg to 250 mg of active principle per dose.

27. The pharmaceutical composition according to claim 8, wherein the dosage of the active principle is from 1 to 300 mg/kg/day orally and rectally.

28. The pharmaceutical composition according to claim 8, wherein the dosage of the active principle is from 0.1 µg/kg/day to 1 mg/kg/day parenterally.

29. A method of preparing a medicine comprising mixing at least one compound according to claim 1 with a pharmaceutically acceptable vehicle.

30. A method of inhibiting the action of a metalloproteinase involved in the breakdown of the extracellular matrix comprising administering at least one compound according to claim 1 to a patient in need thereof in an amount sufficient to inhibit said metalloproteinase.

31. The method according to claim 30, wherein said extracellular matrix is collagenase, gelatinase, or stromelysines.

32. The method according to claim 30, wherein said patient is an animal or human patient.

33. A method of treating a patient suffering from a disease linked to metalloproteinase breakdown of the extracellular matrix comprising administering to said patient an effective amount of at least one compound according to claim 1 in an amount sufficient to inhibit the metalloproteinase breakdown of the extracellular matrix, wherein said disease is at least one selected from the group consisting of rheumatoid arthritis, osteoarthritis, osteoporosis, corneal ulceration, periodontitis, gingivitis, tumorous invasions, metastatic proliferation, atherosclerosis, AIDS, chronic inflammatory diseases of the intestine, and neurodegenerative disease.

34. The method according to claim 33, wherein said neurodegenerative disease is Alzheimer's disease or plaque sclerosis.

35. A method of inhibiting the release of TNFα from its inactive precursor comprising administering at least one compound according to claim 1 to a patient in need thereof in an amount sufficient to inhibit said release.

36. A method of treating a patient suffering from a disease linked to the release of TNFα from its inactive precursor comprising administering to said patient an effective amount of at least one compound according to claim 1 in an amount sufficient to inhibit said release, wherein said disease is at least one selected from the group consisting of rheumatoid arthritis, Crohn's disease, plaque sclerosis, septic shock, cancer, and cachexia associated with an immunodeficiency.

37. A method of treating a patient suffering from a disease linked to the production of TNFα comprising administering to said patient an effective amount of at least one compound according to claim 1 in an amount sufficient to inhibit said production, wherein said disease is at least one selected from the group consisting of cancer, psoriasis, eczema, formation of keloids, diabetic retinopathy, atherosclerosis, and inflammatory diseases.

38. Process for preparation of the compounds of formula X such as defined in claim 1, in which Y represents —CONHOH (also designated hereinafter as compounds of formula XV), with the exception that $R_1$ is not a heteroarylalkyl group and that $R_2$ is not a heteroarylthiomethyl group, characterized in that it comprises:
an aldolization reaction from a keto-ester XXVII and alkene XXVIII (in particular in the presence of a Lewis acid such as $SnCl_4$ at −80° C. in a solvent such as $CH_2Cl_2$ for 5 minutes to 2 hours), or from a keto-acid (in the form of a sodium salt or triethylamine) XXX and an alkene XXXI (in particular at room temperature between 1 and 10 hours in a THF—$H_2O$ mixture) according to the following diagram:

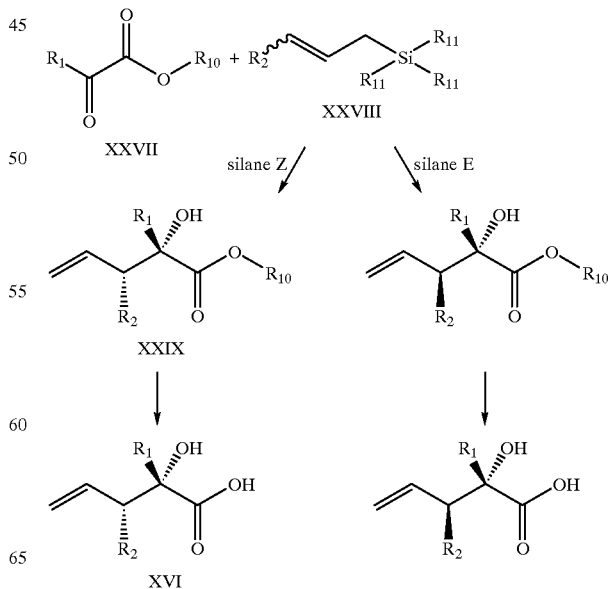

-continued

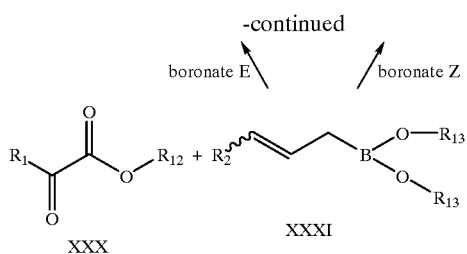

XXX    XXXI in which:

$R_1$ and $R_2$ have the meaning indicated hereinabove, $R_{10}$ is a possibly branched $C_1$–$C_{12}$ alkyl, a benzyl or an optically pure compound such as mandelic acid esterified with a linear or branched $C_1$–$C_3$ alkyl, or a benzyl, $R_{11}$ is a linear or branched $C_1$–$C_3$ alkyl, or a chlorine, $R_{12}$ is sodium or triethylamine, $R_{13}$ is hydrogen, a linear or branched $C_1$–$C_3$ alkyl; $R_{13}$ also may represent a chain forming a ring with the boron atom such as, for example, di-isopropyltartrate, the reactions are diastereoselective and lead to stereochemistry derivatives XVI if the double bond is of Z geometry for the compounds XXVIII and E geometry for the compounds XXXI, the obtaining of the aforementioned compounds of formula XV then being accomplished according to the following reaction diagram:

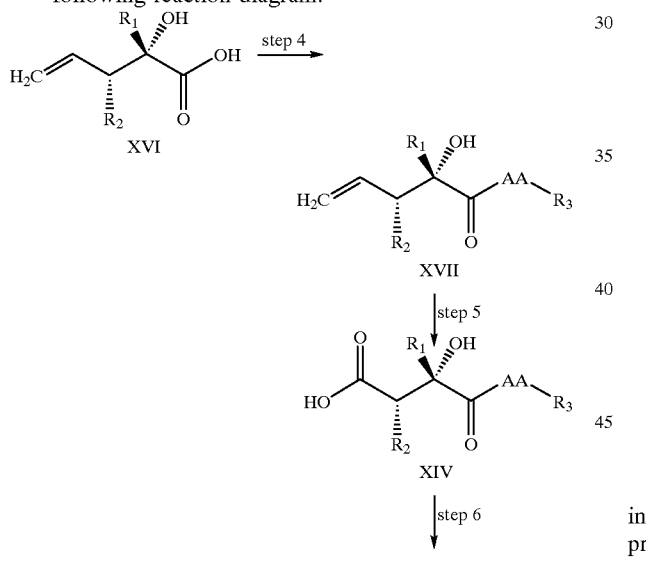

-continued

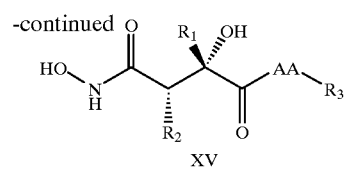

XV in which:

steps 4 and 6 are performed as in steps 1 and 3 of the reaction diagram of claim 17 respectively, and starting from compounds XVI and XIV, which leads to the compounds of formula XVII and XV respectively, step 5 consists in oxidizing the double ethylene bond of the compound of formula XVII into acid, in particular by ozonolysis (for example at −60° C. in $CH_2Cl_2$ until obtaining a steady blue color), then oxidation (in particular at room temperature with $NaClO_2$ and $NaH_2PO_4$ in tBuOH—$H_2O$ for 15 hours) or directly by $KMnO_4$/$NaIO_4$ (in particular at room temperature in a tBuOH—$H_2O$ mixture for 1 to 10 hours), which leads to the compound of formula XIV.

39. Process for preparation of the compounds of formula X such as defined in claim 1, in which Y represents:

—SH, or a group with the formula

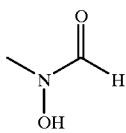

or a group with the formula

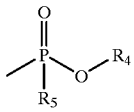

in which $R_4$ and $R_5$ are such as defined in claim 1, said process being performed according to the following diagram:

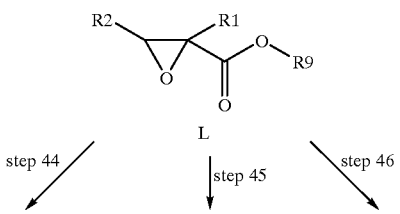

-continued

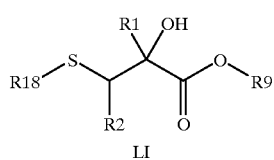
LI

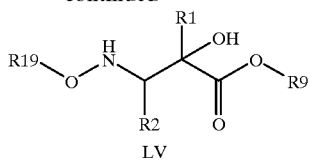
LV

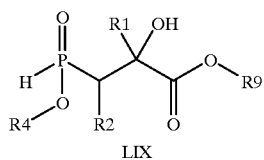
LIX step 47 ↓ step 50 ↓ step 54 ↓

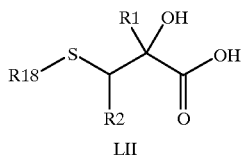
LII

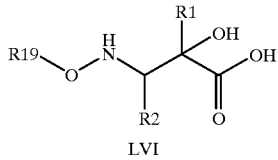
LVI

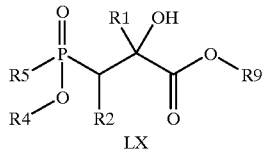
LX step 48 ↓ step 51 ↓ step 55 ↓

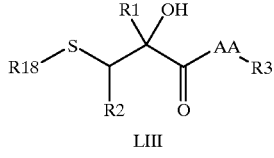
LIII

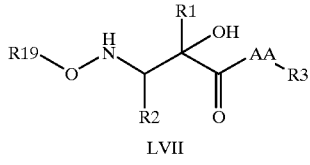
LVII

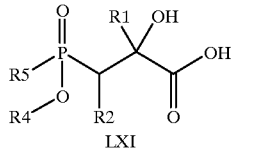
LXI step 49 ↓ step 52 ↓ step 56 ↓

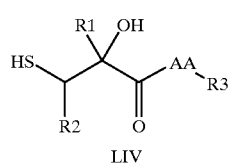
LIV

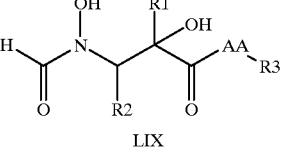
LVIII

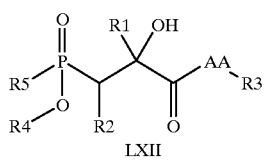
LXII step 53 ↓ step 57 ↓

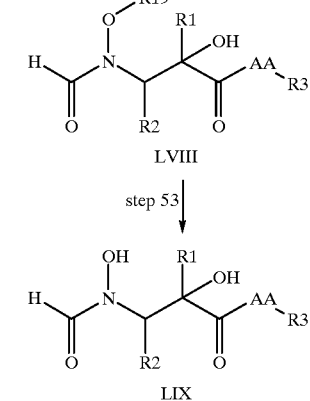
LIX

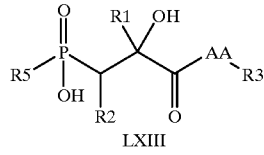
LXIII in which:

step 44 consists in opening an epoxide of formula L in which $R_1$ and $R_2$ are such as defined in claim 1, and $R_9$ is a carboxylic acid protective group, in particular a benzyl remainder sensitive to catalytic hydrogenolysis, this opening of the epoxide L being accomplished with a nucleophile, for example a thiol protected by an $R_{18}$ group compatible with $R_9$, for example a benzyl in methanol for 1 hour at 60° C., step 47 consists in deprotecting the ester LI, for example with trifluoroacetic acid as before, step 48 is identical to step 1 of the reaction diagram of claim 17, and performed starting from compound LII obtained in the preceding step, step 49 consists in deprotecting the sulfur, for example with sodium in liquid ammonia, in particular at −60° C. for 5 to 15 minutes, step 45 consists in opening the epoxide L with protected hydroxylamine such as defined in step 3 of the process according to claim 17 (with, for example, $R_{19}$=benzyl or THP), step 50 consists in deprotecting the ester LV by a method compatible with $R_{19}$, step 51 is identical to step 48, and performed starting from the compound LVI obtained in the preceding step, step 52 consists in reacting the hydroxylamine LVII with formic acid and acetic anhydride, in particular at a temperature of at least 100° C. for 1 to 15 hours, step 53 consists in cleaving $R_{19}$ on the compound LVIII with, for example, $H_2$ Pd/C or HCl 1N depending on the structure of $R_{19}$ as before, step 46 consists in opening an epoxide L with hypophosphorous acid with the formula $H_3PO_2$, then esterification with a coupling agent such as DCC and an $R_4OH$ group in which $R_4$ is such as defined in claim 1, in the presence, for example, of trimethylorthoformate and tetramethylguanidine at room temperature for 5 hours, step 54 consists in treating the compound LIX with a compound with the formula

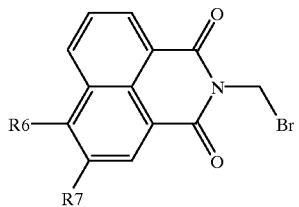

(prepared according to the methods described in the literature) in which $R_6$ and $R_7$ are such as defined hereinabove, in particular in $CH_2Cl_2$ in the presence of bis trimethylsilyl acetamide at room temperature for 5 hours, which leads to the obtaining of the compound of formula LX in which $R_5$ represents:

step 55 consists in cleaving the $R_9$ ester by a method compatible with $R_4$ as previously, step 56 is identical to step 48, and performed starting from the compound LXI obtained in the preceding step, step 57 consists in cleaving the $R_4$ group of the compound LXII obtained in the preceding step, for example with the aid of NaI in acetone under reflux for 15 hours.

* * * * *